United States Patent
Ling et al.

(10) Patent No.: US 11,773,168 B2
(45) Date of Patent: Oct. 3, 2023

(54) FCRN ANTIBODIES AND METHODS OF USE THEREOF

(71) Applicant: Momenta Pharmaceuticals, Inc., Cambridge, MA (US)

(72) Inventors: Leona E. Ling, Winchester, MA (US); Darrell Nix, Colebrook, NH (US); Nicholas A. Cilfone, Cambridge, MA (US)

(73) Assignee: MOMENTA PHARMACEUTICALS, INC., Cambridge, MA (US)

( * ) Notice: Subject to any disclaimer, the term of this patent is extended or adjusted under 35 U.S.C. 154(b) by 75 days.

(21) Appl. No.: 16/771,147

(22) PCT Filed: Dec. 13, 2018

(86) PCT No.: PCT/US2018/065568
§ 371 (c)(1),
(2) Date: Jun. 9, 2020

(87) PCT Pub. No.: WO2019/118791
PCT Pub. Date: Jun. 20, 2019

(65) Prior Publication Data
US 2022/0064290 A1    Mar. 3, 2022

Related U.S. Application Data

(60) Provisional application No. 62/701,354, filed on Jul. 20, 2018, provisional application No. 62/598,402, filed on Dec. 13, 2017.

(51) Int. Cl.
*C07K 16/28* (2006.01)
*A61P 37/02* (2006.01)

(52) U.S. Cl.
CPC ........... *C07K 16/283* (2013.01); *A61P 37/02* (2018.01); *C07K 2317/51* (2013.01); *C07K 2317/515* (2013.01)

(58) Field of Classification Search
None
See application file for complete search history.

(56) References Cited

U.S. PATENT DOCUMENTS

| | | | |
|---|---|---|---|
| 7,662,928 B2 | 2/2010 | Balthasar et al. | |
| 10,676,526 B2 | 6/2020 | Kehry et al. | |
| 11,345,751 B2 * | 5/2022 | Ling | A61P 27/02 |
| 2009/0131639 A1 | 5/2009 | Kakuta et al. | |
| 2011/0027262 A1 | 2/2011 | Das et al. | |
| 2011/0059101 A9 | 3/2011 | Kolkman et al. | |
| 2014/0235482 A1 | 8/2014 | Georgiou et al. | |
| 2014/0308206 A1 | 10/2014 | Sexton et al. | |
| 2015/0118240 A1 | 4/2015 | Finney et al. | |
| 2015/0157709 A1 | 6/2015 | Everett et al. | |
| 2015/0329628 A1 | 11/2015 | Antochshuk et al. | |
| 2016/0194397 A1 | 7/2016 | TenHoor et al. | |
| 2018/0016334 A1 | 1/2018 | Kehry et al. | |
| 2020/0003191 A1 | 1/2020 | Kraft et al. | |
| 2020/0299382 A1 | 9/2020 | Kehry et al. | |
| 2021/0299255 A1 | 9/2021 | Zhang et al. | |
| 2021/0340251 A1 | 11/2021 | Zhang et al. | |
| 2022/0144946 A1 | 5/2022 | Ramchandran et al. | |
| 2022/0259308 A1 | 8/2022 | Arroyo et al. | |

FOREIGN PATENT DOCUMENTS

| | | |
|---|---|---|
| CN | 101124245 | 2/2008 |
| CN | 102149729 | 8/2011 |
| CN | 104479017 A | 4/2015 |
| EP | 3010938 A1 | 4/2016 |
| EP | 3250610 A2 | 12/2017 |
| JP | 2011523351 A | 8/2011 |
| JP | 2014523737 A | 9/2014 |
| JP | 6853178 B2 | 3/2021 |
| JP | 7094941 B2 | 7/2022 |
| KR | 20140036267 A | 3/2014 |
| WO | WO 2005/013912 | 2/2005 |
| WO | WO 2009/131702 | 10/2009 |
| WO | WO 2012/167039 | 12/2012 |
| WO | WO 2014/019727 | 2/2014 |
| WO | WO 2014/179601 | 11/2014 |
| WO | WO 2014/204280 | 12/2014 |
| WO | 2015167293 A1 | 11/2015 |

(Continued)

OTHER PUBLICATIONS

Buyon et al. Journal of Internal Medicine 265: 653-662, 2009.*
Roopenian et al. Nature Reviews Immunology 7:715-725, 2007.*
Casipit et al., "Improving the Binding Affinity of an Antibody using Molecular Modeling and Site-Directed Mutagenesis," Protein Science, Aug. 1, 1998, 7:1671-1680.
Chien et al., "Significant structural and functional change of an antigen-binding site by a distant amino acid substitution: Proposal of a structural mechanism," Proc Natl Acad Sci USA., 1989, 86(14):5532-5536.
Christianson et al., "Monoclonal antibodies directed against human FcRn and their applications." MAbs, Mar. 1, 2012, 4(2):208-216.

(Continued)

*Primary Examiner* — Nora M Rooney
(74) *Attorney, Agent, or Firm* — Troutman Pepper Hamilton Sanders LLP

(57) ABSTRACT

The present invention features antibodies that bind to human neonatal Fc receptor (FcRn). These anti-FcRn antibodies are useful, e.g., to promote clearance of autoantibodies in a subject, to suppress antigen presentation in a subject, to block an immune response, e.g., block an immune complex-based activation of the immune response in a subject, and to treat immunological diseases (e.g., autoimmune diseases) in a subject. These anti-FcRn antibodies are also useful, e.g., to decrease pathogenic antibody transport across the placenta of a pregnant subject, to increase pathogenic antibody catabolism in a pregnant subject, and to treat an antibody-mediated enhancement of viral disease in a fetus or a neonate.

13 Claims, 34 Drawing Sheets

Specification includes a Sequence Listing.

(56) References Cited

FOREIGN PATENT DOCUMENTS

| WO | WO 2016/123521 | 8/2016 |
|---|---|---|
| WO | WO 2016/183352 | 11/2016 |
| WO | WO 2018/023136 | 2/2018 |
| WO | WO 2007/087289 | 8/2018 |
| WO | 2019110823 A1 | 6/2019 |
| WO | 2019118791 A1 | 6/2019 |
| WO | 2019160979 A1 | 8/2019 |
| WO | 2020079086 A1 | 4/2020 |

OTHER PUBLICATIONS

Committee on Obstetric Practice American Institute of Ultrasound in Medicine Society for Maternal-Fetal Medicine, "Committee Opinion. Number 700: Methods for Estimating the Due Date," Obstetrics & Gynecology, May 2017, 129(5):e150-e154.

Ellinger et al., "Overexpression of the human neonatal Fc-receptor alpha-chain in trophoblast-derived BeWo cells increases cellular retention of beta2-microglobulin," Placenta., 2005, 26(2-3):171-182.

Hiroyuki et al., "Tryptophan H33 play.s an important role in pyrimidine (6-4) pyrimidone photoproduct binding by a higli-affinity antibody," Protein Engineering, 1999, 12(10):879-884.

Hoftman et al., "Newborn illnesses caused by transplacental antibodies," AdvPediatr., 2008, 55:271-304.

Hutson et al., "The human placental perfusion model: a systematic review and development of a model to predict in vivo transfer of therapeutic drugs," Clin Pharmacol Ther., 2011, 90(1):67-76.

International Search Report and Written Opinion in International Application No. PCT/US2016/15720, dated Jul. 26, 2016, 16 pages.

International Search Report and Written Opinion in International Application No. PCT/US2018/065568, dated Apr. 2, 2019, 14 pages.

International Search Report and Written Opinion in International Application No. PCT/US2017/44765, dated Jan. 9, 2018, 14 pages.

International Preliminary Report on Patentability in International Application No. PCT/US2017/044765, dated Jan. 29, 2019, 9 pages.

International Preliminary Report on Patentability in International Applications No. PCT/US2016/015720, dated Aug. 1, 2017, 11 pages.

Junghans and Anderson, "The protection receptor for IgG catabolism is the ,32-microglobulin-containing neonatal intestinal transport receptor," PNAS, May 1996, 93:5512-5516.

Kobrin et al., "A V Region Mutation in a Phosphocholine-Binding Monoclonal Antibody Results in Loss of Antigen Binding," J of Immunol., Mar. 15, 1991, 146(6):2017-2020.

Li et al., "The Maternal Immune Response to Fetal Platelet GPIbα Causes Frequent Miscarriage in Mice That Can Be Prevented by Intravenous IgG and anti-FcRn Therapies," J Clin Invest., Nov. 2011, 121(11):4537-4547.

Liu et al., "Amelioration of Experimental Autoimmune Myasthenia Gravis in Rats by Neonatal FcR Blockade," J of Immunol., Apr. 15, 2007, 178(8):5390-5398.

Ling et al., "32: M281, an anti-FcRn antibody, inhibits IgG transfer in a human ex-vivo placental perfusion model," Jan. 2019, 220(1):32.

Mahadevan et al., "Placental transfer of anti-tumor necrosis factor agents in pregnant patients with inflammatory bowel disease," Clin Gastroenterol Hepatol., 2013, 11(3):286-292.

Malek, "Ex vivo human placenta models: transport of immunoglobulin G and its subclasses," Vaccine, 2003, 21:3362-3364.

Mathiesen et al., "Quality assessment of a placental perfusion protocol," Reproductive Toxicology, 2010, 30:138-146.

Morck et al., "Placental transport and in vitro effects of Bisphenol A," Reproductive Toxicol., 2010, 30:131-137.

Morgan et al., "The effect of intravenous immunoglobulin on placental transfer of a platelet-specific antibody: Anti-P1A1," Transfusion Medicine, 1991, 1:209-216.

Nanovskaya et al., "Transplacental Transfer and Metabolism of Buprenorphine," J Pharmacol Exp Ther., 2002, 300(1):26-33.

Panka et al., "Defining the Structural Correlates Responsible for Loss of Arsonate Affinity in an IDCR Antibody Isolated From an Autoimmune Mouse," Mol Immunol., Aug. 1, 1993, 30(11):1013-1020.

Porter et al., "Certolizumab pegol does not bind the neonatal Fc receptor (FcRn):Consequences for FcRn-mediated in vitro transcytosis and ex vivo human placental transfer," J Repro Imm., 2016, 116:7-12.

Roopenian et al., "Clinical Ramifications of the MHC Family Fc Receptor FcRn," J Clin Immunol., 2010, 30(6):790-797.

Roopenian et al., "FcRn: the neonatal Fc receptor comes of age," Nature Immunol. 2007; 7:715-25.

Rudikoff et al., "Single Amino Acid Substitution Altering Antigen-Binding Specificity," Proc Natl Acad Sci USA., Mar. 1, 1982, 79:1979-1983.

Schildbach et al., "Modulation of antibody affinity by a non-contact residue," Protein Science, 1993, 2:206-214.

Schneider et al., "Effect of flow rate ratio on the diffusion of antipyrine and 3H2O in the isolated dually in vitro perfused lobe of the human placenta," Contrib Gynecol Obstet., 1985, 13:114-123.

Schneider et al., "Transfer across the perfused human placenta of antipyrine, sodium and leucine," Am J Obstet Gynecol., 1972, 114:822-828.

Singapore Search Report and Written Opinion in Singapore Application No. 11201705475Q, dated Jul. 31, 2018, 10 pages.

Urbaniak et al., "Transfer of anti-D antibodies across the isolated perfused human placental lobule and inhibition by high dose intravenous immunoglobulin: a possible mechanism of action," Br J Hematol., 1997, 96:186-93.

Urbaniak et al., "Variable inhibition of placental IgG transfer in vitro with commercial IVgG preparations," Br J Haematol., 1999, 107:815-817.

Winkler et al., "Changing the Antigen Binding Specificity by Single Point Mutations of an Anti-p24 (HIV-1) Antibody," J of Immunol., Oct. 15, 2000, 165(8):4505-4514.

Zhu et al., "MHC class I-related neonatal Fc receptor for IgG is functionally expressed in monocytes, intestinal macrophages, and dendritic cells," J Immunol., 2001, 166(5):3266-3276.

Nonfinal Office Action dated Jun. 29, 2021 received in U.S. Appl. No. 16/321,801.

Kussie et al., "A Single Engineered Amino Acid Substitution Changes Antibody Fine Specificity", Journal of Immunology (1994) 152(1): pp. 146-152.

Chen et al., "Enhancement and destruction of antibody function by somatic mutation: unequal occurrence is controlled by V gene combinatorial associations", The EMBO Journal (1995) vol. 14 No. 12, pp. 2784-2794.

Ling et al., "M281: A Therapeutic Anti-FcRn Blocking Antibody for Rapid Clearance of IgG and IgG Autoantibodies in Immune Cytopenias and Other Auto/Allm-Immune Disease", Blood (2015) 126, 23: 3472.

International Preliminary Report on Patentability in International Application No. PCT/US2018/065568, dated Jun. 16, 2020, 10 pages.

Christensen, D et al., Trehalose preserves DDA/TDB liposomes and their adjuvant effect during freeze-drying, Biochimica et Biophysica Acta., Sep. 2007, Epub May 13, 2007, vol. 1768, No. 9, pp. 2120-2129.

International Search Report and Written Opinion in International Application No. PCT/US2019/042597, dated Nov. 26, 2019.

International Search Report and Written Opinion in International Application No. PCT/US2019/042615, dated Nov. 15, 2019.

International Search Report and Written Opinion in International Application No. PCT/US2020/044731, dated Dec. 22, 2020.

Montes, T et al., Genetic Modification of the Penicillin G Acylase Surface to Improve its Reversible Immobilization on Ionic Exchangers, Applied and Encironmental Microbiology, Jan. 2007, Epub Nov. 10, 2006, vol. 73, No. 1, pp. 312-319.

Whittamker, MM et al., Burst Kinetics and Redoc Transformations of the Active Site Manganesse Ion in Oxalate Oxidase: Implications for the Catalytic Mechanism, The Journal of Biological Chemistry, Mar. 9, 2007, Epub Jan. 8, 2007, vol. 282, No. 10, pp. 7011-7023.

(56) References Cited

OTHER PUBLICATIONS

Singapore Search Report and Written Opinion in Application No. 10202007232W, dated Feb. 17, 2022.
Extended European Search Report Application No. EP19840429, dated Mar. 18, 2022.
Wang, et al., "Antibody Structure, Instability, and Formulation", Journal of Pharmaceutical Sciences, (2007) vol. 96, No 1.
Warne et al., "Development of high concentration protein biopharmaceuticals: The use of platform approaches in formulation development", European Journal of Pharmaceutics and Biopharmaceutics (2011) 78: pp. 208-212.
Daugherty et al., "Formulation and Delivery Issues for Monoclonal Antibody Therapeutics", Current Trends in Monoclonal Antibody Development and Manufacturing (2010) pp. 103-129.
Sharma et al., "The Formulation and Delivery of Monoclonal Antibodies", Therapeutic Monoclonal Antibodies: From Bench to Clinic (2009) pp. 1-37.
International Search Report and Wrtten Opinion in International Application No. PCT/US2022/024354, dated Sep. 12, 2022.
Notice of Allowance dated Nov. 22, 2022 received in U.S. Appl. No. 16/825,066.
Kortt et al., "Dimaric and trimeric antibodies: high avidity scFvs for cancer targeting", Biomolecular Engineering (2001) 18; 95-108.
Nonfinal Office Action dated Oct. 17, 2022 received in U.S. Appl. No. 17/519,811.
Ling, et al., "M281, and Anti-FcRn Antibody:Pharmacodynamics, Pharmacokinetics, and Safety Across the Full Range of IgG Reduction in a First-in-Human Study", Clinical Pharmacology & Therapeutics (2019) vol. 105 No. 4, pp. 1031-1039.
Lazaridis, et al., "Autoantibody Specificities in Myasthenia Gravis; Implications for Improved Diagnostics and Therapeutics", Front. Immunol. (2020) 14; 11:212.
Roopenian, et al., "Albumin-deficient mouse models for studying metabolism of of human albumin and pharmacokinetics of albumin-based drugs", mABS (2015) vol. 7, Issue 2, pp. 344-351.
Hui-Juan et al., "Prokaryotic expression of porcine FcRn-CT and prepartion of polyclonal antibody", Chinese Journal of Vetenary Science (2012) vol. 32, No. 2, pp. 262-271.
Tannemaat et al., "Emerging therapies for autoimmune myasthenia gravis: Towards treatment without corticosteroids". Neuromuscular Disorders (2020 30: pp. 111-119.
Yu et al., "Estimation of Hemolytic Disease of the Newborn in the United States from 1996-2010", (2021).
Notice of Allowance dated Jan. 28, 2022 received in U.S. Appl. No. 16/321,801.
International Search Report and Written Opinion in International Application No. PCT/US2021/058188, dated Apr. 5, 2022.

* cited by examiner

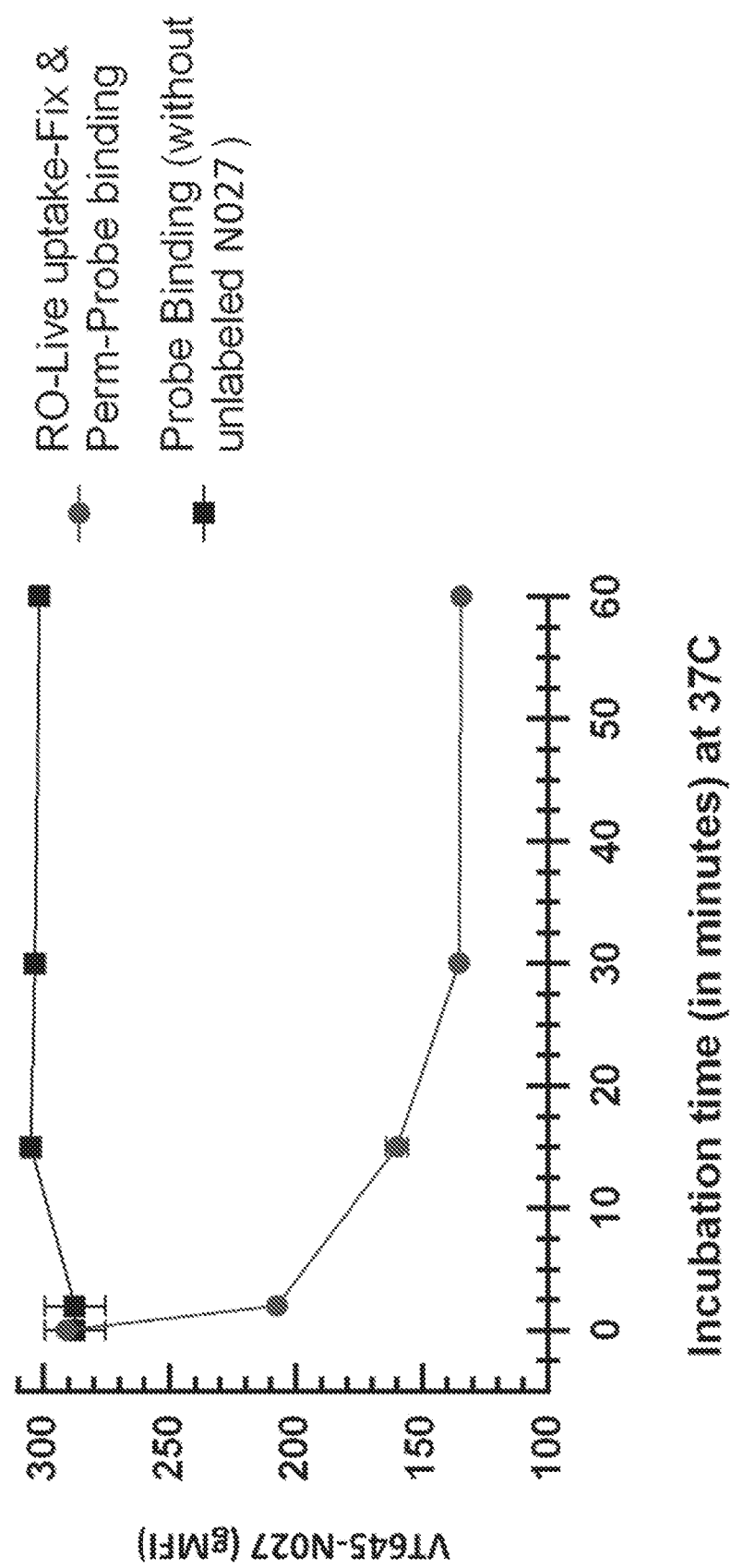

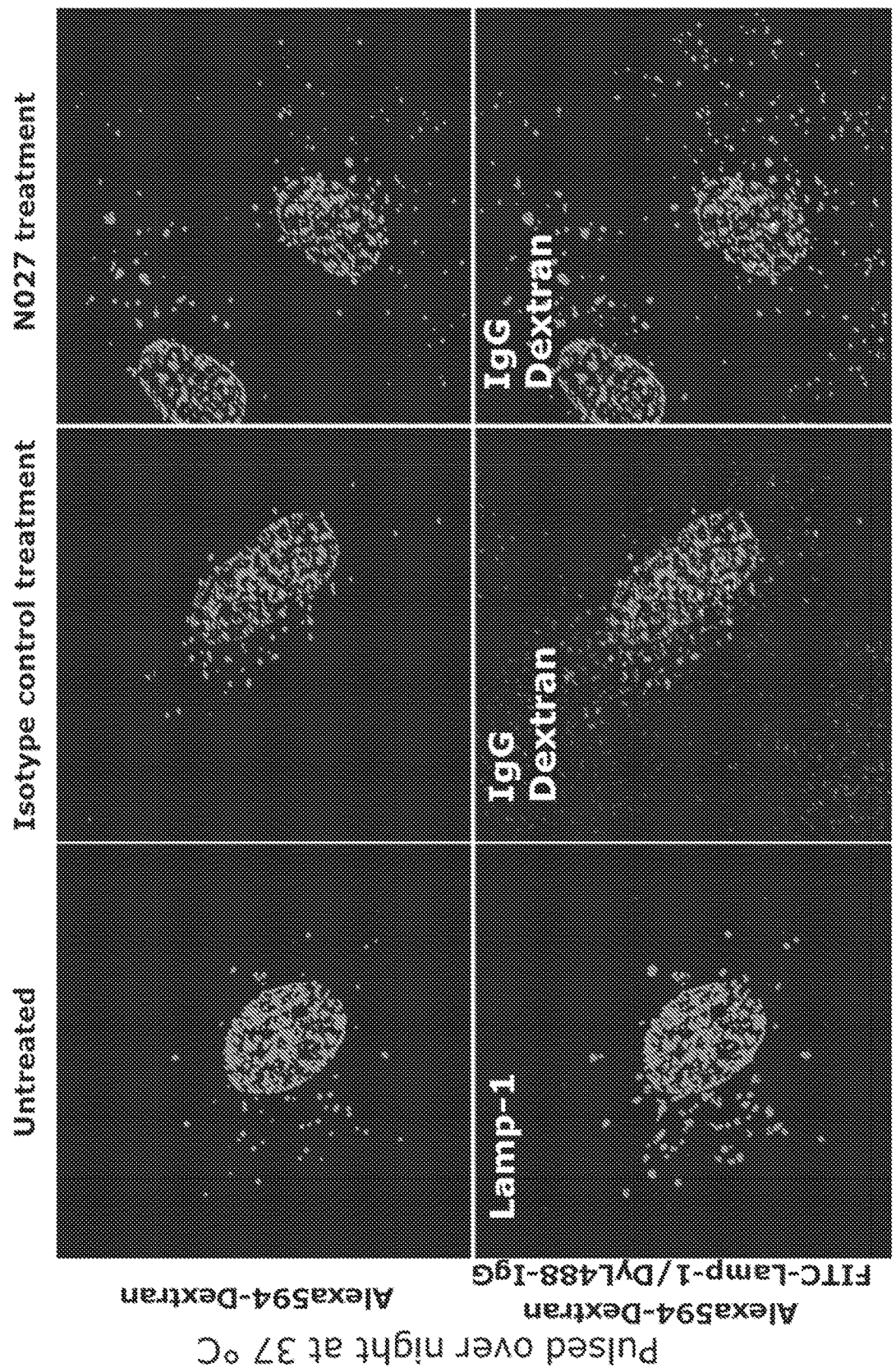

Abbreviations: FcRn = neonatal Fc receptor; SD = standard deviation.

Abbreviations: IgG = immunoglobulin G; SD = standard deviation.

A)  30 mg/kg
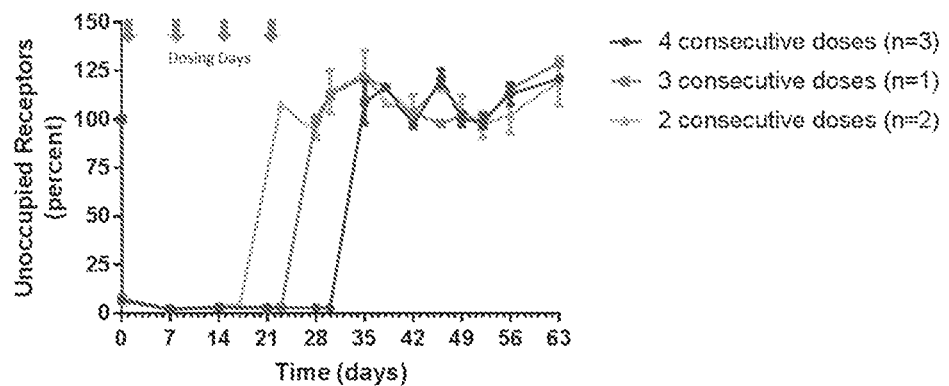
B)  15 mg/kg
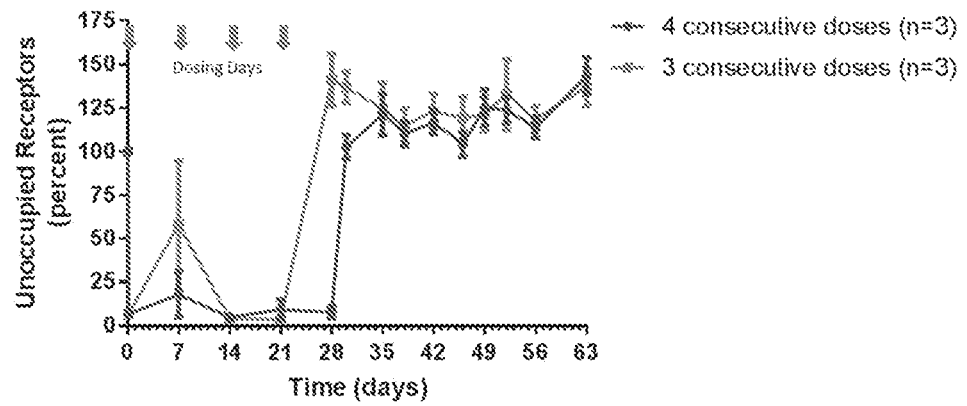
Abbreviations: FcRn = neonatal Fc receptor; MAD = multiple ascending dose; SD = standard deviation.
FIG. 20

A) 30 mg/kg
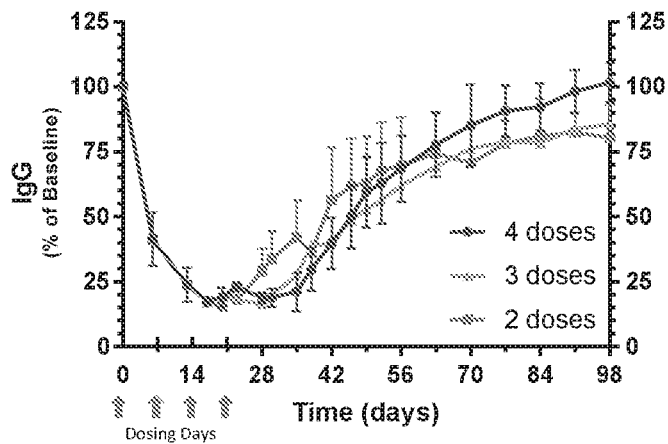
B) 15 mg/kg
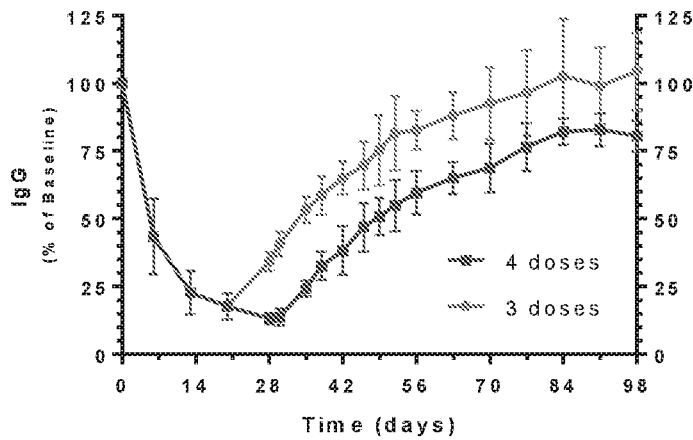
Abbreviations: IgG = immunoglobulin G; MAD = multiple ascending dose; SD = standard deviation
FIG. 21

| MPA1 Dose | Gestation Day | | | | | |
|---|---|---|---|---|---|---|
| | EFD | | | | ePPND | |
| | 38 | 66 | 100/115 | 142 | 44-46 | 135-137 |
| 0 mg/kg | 3.9 ± 0.3 | 3.1 ± 0.4 | 2.8 ± 0.3 | 2.5 ± 0.4 | 3.5 ± 0.3 | 2.7 ± 0.3 |
| 100 mg/kg | 3.7 ± 0.1 | 2.4 ± 0.2 | 2.5 ± 0.2 | 2.3 ± 0.3 | 3.4 ± 0.3 | 2.3 ± 0.2 |
| 300 mg/kg | 3.5 ± 0.3 | 2.0 ± 0.3 | 1.9 ± 0.2 | 1.9 ± 0.3 | 3.4 ± 0.3 | 2.0 ± 0.2 |

FIG. 32

SEQUENCE LISTING

```
<160> NUMBER OF SEQ ID NOS: 24

<210> SEQ ID NO 1
<211> LENGTH: 14
<212> TYPE: PRT
<213> ORGANISM: Artificial Sequence
<220> FEATURE:
<223> OTHER INFORMATION: complementarity-determining region

<400> SEQUENCE: 1

Thr Gly Thr Gly Ser Asp Val Gly Ser Tyr Asn Leu Val Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: complementarity-determining region

<400> SEQUENCE: 2

Gly Asp Ser Glu Arg Pro Ser
1               5
```

```
<210> SEQ ID NO 3
<211> LENGTH: 10
<212> TYPE: PRT
<213> ORGANISM: Artificial Sequence
<220> FEATURE:
<223> OTHER INFORMATION: complementarity-determining region

<400> SEQUENCE: 3

Ser Ser Tyr Ala Gly Ser Gly Ile Tyr Val
1               5                   10

<210> SEQ ID NO 4
<211> LENGTH: 5
<212> TYPE: PRT
<213> ORGANISM: Artificial Sequence
<220> FEATURE:
<223> OTHER INFORMATION: complementarity-determining region

<400> SEQUENCE: 4

Thr Tyr Ala Met Gly
1               5

<210> SEQ ID NO 5
<211> LENGTH: 5
<212> TYPE: PRT
<213> ORGANISM: Artificial Sequence
<220> FEATURE:
<223> OTHER INFORMATION: complementarity-determining region

<400> SEQUENCE: 5

Asp Tyr Ala Met Gly
1               5

<210> SEQ ID NO 6
<211> LENGTH: 5
<212> TYPE: PRT
<213> ORGANISM: Artificial Sequence
<220> FEATURE:
<223> OTHER INFORMATION: complementarity-determining region

<400> SEQUENCE: 6

Asn Tyr Ala Met Gly
1               5

<210> SEQ ID NO 7
<211> LENGTH: 14
<212> TYPE: PRT
<213> ORGANISM: Artificial Sequence
<220> FEATURE:
<223> OTHER INFORMATION: complementarity-determining region

<400> SEQUENCE: 7

Ser Ile Gly Ser Ser Gly Ala Gln Thr Arg Tyr Ala Asp Ser
1               5                   10

<210> SEQ ID NO 8
<211> LENGTH: 14
<212> TYPE: PRT
<213> ORGANISM: Artificial Sequence
<220> FEATURE:
<223> OTHER INFORMATION: complementarity-determining region

<400> SEQUENCE: 8

Ser Ile Gly Ala Ser Gly Ser Gln Thr Arg Tyr Ala Asp Ser
1               5                   10
```

```
<210> SEQ ID NO 9
<211> LENGTH: 14
<212> TYPE: PRT
<213> ORGANISM: Artificial Sequence
<220> FEATURE:
<223> OTHER INFORMATION: complementarity-determining region

<400> SEQUENCE: 9

Ser Ile Gly Ala Ser Gly Ala Gln Thr Arg Tyr Ala Asp Ser
1               5                   10

<210> SEQ ID NO 10
<211> LENGTH: 14
<212> TYPE: PRT
<213> ORGANISM: Artificial Sequence
<220> FEATURE:
<223> OTHER INFORMATION: complementarity-determining region

<400> SEQUENCE: 10

Ser Ile Gly Ala Ser Gly Gly Gln Thr Arg Tyr Ala Asp Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: complementarity-determining region

<400> SEQUENCE: 11

Leu Ala Ile Gly Asp Ser Tyr
1               5

<210> SEQ ID NO 12
<211> LENGTH: 14
<212> TYPE: PRT
<213> ORGANISM: Artificial Sequence
<220> FEATURE:
<223> OTHER INFORMATION: complementarity-determining region
<220> FEATURE:
<221> NAME/KEY: MISC_FEATURE
<222> LOCATION: (1)..(1)
<223> OTHER INFORMATION: X = Thr, Ala, Ser, or Ile
<220> FEATURE:
<221> NAME/KEY: MISC_FEATURE
<222> LOCATION: (12)..(12)
<223> OTHER INFORMATION: X = Leu or Ile

<400> SEQUENCE: 12

Xaa Gly Thr Gly Ser Asp Val Gly Ser Tyr Asn Xaa Val Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: complementarity-determining region
<220> FEATURE:
<221> NAME/KEY: MISC_FEATURE
<222> LOCATION: (3)..(3)
<223> OTHER INFORMATION: X = Ser, Asn, or Thr
<220> FEATURE:
<221> NAME/KEY: MISC_FEATURE
<222> LOCATION: (4)..(4)
<223> OTHER INFORMATION: X = Gln, Glu, or Asn
<220> FEATURE:
<221> NAME/KEY: MISC_FEATURE
<222> LOCATION: (4)..(4)
<223> OTHER INFORMATION: X = Gln, Glu, or Asn
```

```
<400> SEQUENCE: 13

Gly Asp Xaa Xaa Arg Pro Ser
1               5

<210> SEQ ID NO 14
<211> LENGTH: 10
<212> TYPE: PRT
<213> ORGANISM: Artificial Sequence
<220> FEATURE:
<223> OTHER INFORMATION: complementarity-determining region
<220> FEATURE:
<221> NAME/KEY: MISC_FEATURE
<222> LOCATION: (1)..(1)
<223> OTHER INFORMATION: X = Cys, Ser, Ile, or Tyr
<220> FEATURE:
<221> NAME/KEY: MISC_FEATURE
<222> LOCATION: (4)..(4)
<223> OTHER INFORMATION: X = Ala or Val

<400> SEQUENCE: 14

Xaa Ser Tyr Xaa Gly Ser Gly Ile Tyr Val
1               5                   10

<210> SEQ ID NO 15
<211> LENGTH: 5
<212> TYPE: PRT
<213> ORGANISM: Artificial Sequence
<220> FEATURE:
<223> OTHER INFORMATION: complementarity-determining region
<220> FEATURE:
<221> NAME/KEY: MISC_FEATURE
<222> LOCATION: (1)..(1)
<223> OTHER INFORMATION: X = Glu, Thr, Asp, or Asn

<400> SEQUENCE: 15

Xaa Tyr Ala Met Gly
1               5

<210> SEQ ID NO 16
<211> LENGTH: 14
<212> TYPE: PRT
<213> ORGANISM: Artificial Sequence
<220> FEATURE:
<223> OTHER INFORMATION: complementarity-determining region
<220> FEATURE:
<221> NAME/KEY: MISC_FEATURE
<222> LOCATION: (4)..(4)
<223> OTHER INFORMATION: X = Ser or Ala
<220> FEATURE:
<221> NAME/KEY: MISC_FEATURE
<222> LOCATION: (7)..(7)
<223> OTHER INFORMATION: X = Gly, Ser, or Ala
<220> FEATURE:
<221> NAME/KEY: MISC_FEATURE
<222> LOCATION: (10)..(10)
<223> OTHER INFORMATION: X = Lys or Arg

<400> SEQUENCE: 16

Ser Ile Gly Xaa Ser Gly Xaa Gln Thr Xaa Tyr Ala Asp Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: complementarity-determining region
<220> FEATURE:
<221> NAME/KEY: MISC_FEATURE
<222> LOCATION: (3)..(3)
<223> OTHER INFORMATION: X = Ile, Leu, or His
```

```
<220> FEATURE:
<221> NAME/KEY: MISC_FEATURE
<222> LOCATION: (4)..(4)
<223> OTHER INFORMATION: X = Gly, Ser, Asp, Gln, or His

<400> SEQUENCE: 17

Leu Ala Xaa Xaa Asp Ser Tyr
1               5

<210> SEQ ID NO 18
<211> LENGTH: 14
<212> TYPE: PRT
<213> ORGANISM: Artificial Sequence
<220> FEATURE:
<223> OTHER INFORMATION: complementarity-determining region
<220> FEATURE:
<221> NAME/KEY: MISC_FEATURE
<222> LOCATION: (4)..(4)
<223> OTHER INFORMATION: X = Ser or Ala
<220> FEATURE:
<221> NAME/KEY: MISC_FEATURE
<222> LOCATION: (7)..(7)
<223> OTHER INFORMATION: X = Gly, Ser or Ala

<400> SEQUENCE: 18

Ser Ile Gly Xaa Ser Gly Xaa Gln Thr Arg Tyr Ala Asp Ser
1               5                   10

<210> SEQ ID NO 19
<211> LENGTH: 216
<212> TYPE: PRT
<213> ORGANISM: Artificial Sequence
<220> FEATURE:
<223> OTHER INFORMATION: antibody light chain

<400> SEQUENCE: 19

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Gly Asp Ser Glu Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Gly Ile Tyr Val Phe Gly Thr Gly Thr Lys Val Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205
```

```
Thr Val Ala Pro Thr Glu Cys Ser
    210             215

<210> SEQ ID NO 20
<211> LENGTH: 445
<212> TYPE: PRT
<213> ORGANISM: Artificial Sequence
<220> FEATURE:
<223> OTHER INFORMATION: antibody heavy chain

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ser Ser Gly Ala Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350
```

```
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly
            435                 440                 445

<210> SEQ ID NO 21
<211> LENGTH: 445
<212> TYPE: PRT
<213> ORGANISM: Artificial Sequence
<220> FEATURE:
<223> OTHER INFORMATION: antibody heavy chain

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Ser Gln Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
                275                 280                 285

Lys Pro Arg Glu Glu Gln Tyr Ala Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 22
<211> LENGTH: 445
<212> TYPE: PRT
<213> ORGANISM: Artificial Sequence
<220> FEATURE:
<223> OTHER INFORMATION: antibody heavy chain

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ala Met Gly Trp Val Arg Gln Ala Pro Gly Lys Gly Leu Glu Trp Val
            35                  40                  45

Ser Ser Ile Gly Ala Ser Gly Ala Gln Thr Arg Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Ala Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 23
<211> LENGTH: 445
<212> TYPE: PRT
<213> ORGANISM: Artificial Sequence
<220> FEATURE:
<223> OTHER INFORMATION: antibody heavy chain

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Gly Trp Val Arg Gln Ala Pro Gly Lys Gly Leu Glu Trp Val
        35                  40                  45

Ser Ser Ile Gly Ala Ser Gly Gly Gln Thr Arg Tyr Ala Asp Ser Val
    50                  55                  60

Lys Gly Arg Phe Thr Ile Ser Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Ala Ile Gly Asp Ser Tyr Trp Gly Gln Gly Thr Met Val
            100                 105                 110

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Ala Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
            435                 440                 445

<210> SEQ ID NO 24
<211> LENGTH: 445
<212> TYPE: PRT
<213> ORGANISM: Artificial Sequence
<220> FEATURE:
<223> OTHER INFORMATION: antibody heavy chain

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30
```

```
Ala Met Gly Trp Val Arg Gln Ala Pro Gly Lys Gly Leu Glu Trp Val
        35                  40                  45
Ser Ser Ile Gly Ala Ser Gly Ser Gln Thr Arg Tyr Ala Asp Ser Val
        50                  55                  60
Lys Gly Arg Phe Thr Ile Ser Arg Asp Asn Ser Lys Asn Thr Leu Tyr
65                      70                  75                  80
Leu Gln Met Asn Ser Leu Arg Ala Glu Asp Thr Ala Val Tyr Tyr Cys
                85                  90                  95
Ala Arg Leu Ala Ile Gly Asp Ser Tyr Trp Gly Gln Gly Thr Met Val
                100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
        130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Lys Val Glu Pro Lys Ser Cys Asp Lys Thr His Thr
        210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
        275                 280                 285
Lys Pro Arg Glu Glu Gln Tyr Ala Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Glu Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly
        435                 440                 445
```

FCRN ANTIBODIES AND METHODS OF USE THEREOF

CROSS REFERENCE TO RELATED APPLICATIONS

This application is a national phase application under 35 U.S.C. § 371 of PCT International Application number PCT/US2018/065568, filed Dec. 13, 2018, which claims the benefit of U.S. Patent Application No. 62/598,402, filed Dec. 13, 2017, and U.S. Application No. 62/701,354 filed on Jul. 20, 2018. The disclosure of each of these applications are incorporated herein in their entirety.

BACKGROUND OF THE INVENTION

Therapeutic proteins, e.g., therapeutic antibodies, have rapidly become a clinically important drug class for patients with immunological diseases. Numerous autoimmune and alloimmune diseases are mediated by pathogenic antibodies. There exists a need for novel methods of treating immunological diseases.

SUMMARY OF THE INVENTION

The present invention features novel antibodies to human neonatal Fc receptor (FcRn). These anti-FcRn antibodies are useful, e.g., to promote clearance of autoantibodies in a subject, to suppress antigen presentation in a subject, to block an immune response, e.g., block an immune complex-based activation of the immune response in a subject, or to treat immunological diseases (e.g., autoimmune diseases) in a subject.

In one aspect, the invention features an isolated antibody that binds to human FcRn. The isolated antibody contains: (1) a light chain variable region that includes a CDR L1, a CDR L2, and a CDR L3 and (2) a heavy chain variable region that includes a CDR H1, a CDR H2, and a CDR H3, wherein the CDR L1 comprises a sequence having no more than two amino acid substitutions relative to the sequence of TGTGSDVGSYNLVS (SEQ ID NO: 1), the CDR L2 comprises a sequence having no more than one amino acid substitutions relative to the sequence of GDSERPS (SEQ ID NO: 2), the CDR L3 comprises a sequence having no more than one amino acid substitutions relative to the sequence of SSYAGSGIYV (SEQ ID NO: 3), the CDR H1 comprises a sequence having no more than one amino acid substitutions relative to the sequence of TYAMG (SEQ ID NO: 4), DYAMG (SEQ ID NO: 5), or NYAMG (SEQ ID NO: 6), the CDR H2 comprises a sequence having no more than two amino acid substitutions relative to the sequence of SIGSSGAQTRYADS (SEQ ID NO: 7), SIGASGSQTRYADS (SEQ ID NO: 8), SIGASGAQTRYADS (SEQ ID NO: 9), or SIGASGGQTRYADS (SEQ ID NO: 10), and the CDR H3 comprises a sequence having no more than one amino acid substitutions relative to the sequence of LAIGDSY (SEQ ID NO: 11).

In some embodiments, the antibody binds human FcRn with a $K_D$ of less than 200, 150, 100, 50, or 40 pM.

In some embodiments, the antibody binds human FcRn with a $K_D$ that is less than or equal to that of an antibody having the light chain variable region and heavy chain variable region of N022, N023, N024, N026, or N027, and further having the same Fc region as that of the antibody to which it is being compared. In another aspect, the invention features an isolated antibody containing: (1) a light chain variable region that includes a CDR L1, a CDR L2, and a CDR L3 and (2) a heavy chain variable region that includes a CDR H1, a CDR H2, and a CDR H3, wherein the CDR L1 comprises the sequence of $X_1$GTGSDVGSYN$X_2$VS (SEQ ID NO: 12), the CDR L2 comprises the sequence of GD$X_3X_4$RPS (SEQ ID NO: 13), the CDR L3 comprises the sequence of $X_5$SY$X_6$GSGIYV (SEQ ID NO: 14), the CDR H1 comprises the sequence of $Z_1$YAMG (SEQ ID NO: 15), the CDR H2 comprises the sequence of SIG$Z_2$SG$Z_3$QT$Z_4$YADS (SEQ ID NO: 16), and the CDR H3 comprises the sequence of LA$Z_5Z_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, and $Z_6$ is G, S, D, Q, or H, and wherein the antibody binds human FcRn with a $K_D$ that is less than or equal to that of antibody having the light chain variable region and heavy chain variable region of N026 and further having the same Fc region as the antibody being compared. In some embodiments, $X_1$ is T, A, S, or I. In other embodiments, $X_2$ is L or I. In some embodiments, $X_3$ is S, N, or T. In still other embodiments, $X_4$ is Q, E, or N, $X_5$ is C, S, I, or Y. In some embodiments, $X_6$ is A or V, $Z_1$ is E, T, D, or N. In further embodiments, $Z_2$ is S or A. In some embodiments, $Z_4$ is K or R. In yet other embodiments, $Z_5$ is I, L, or H.

In another aspect, the invention features an isolated antibody containing a light chain variable region that includes a CDR L1 having the sequence of TGTGSDVGSYNLVS (SEQ ID NO: 1), a CDR L2 having the sequence of GDSERPS (SEQ ID NO: 2), and a CDR L3 having the sequence of SSYAGSGIYV (SEQ ID NO: 3), and a heavy chain variable region that includes a CDR H1 having the sequence of $Z_1$YAMG (SEQ ID NO: 15), a CDR H2 having the sequence of SIG$Z_2$SG$Z_3$QTRYADS (SEQ ID NO: 18), and a CDR H3 having the sequence of LAIGDSY (SEQ ID NO: 11), wherein $Z_1$ is T, D, or N, $Z_2$ is S or A, and $Z_3$ is G, S or A.

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGASGAQTRYADS (SEQ ID NO: 7), and a CDR H3 having the sequence of LAIGDSY (SEQ ID NO: 11).

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of DYAMG (SEQ ID NO: 5), a CDR H2 having the sequence of SIGASGSQTRYADS (SEQ ID NO: 8), and a CDR H3 having the sequence of LAIGDSY (SEQ ID NO: 11).

In some embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of NYAMG (SEQ ID NO: 6), a CDR H2 having the sequence of SIGASGAQTRYADS (SEQ ID NO: 9), and a CDR H3 having the sequence of LAIGDSY (SEQ ID NO: 11).

In other embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGASGGQTRYADS (SEQ ID NO: 10), and a CDR H3 having the sequence of LAIGDSY (SEQ ID NO: 11).

In yet other embodiments, the isolated antibody contains a CDR L1 having the sequence of TGTGSDVGSYNLVS (SEQ ID NO: 1), a CDR L2 having the sequence of GDSERPS (SEQ ID NO: 2), a CDR L3 having the sequence of SSYAGSGIYV (SEQ ID NO: 3), a CDR H1 having the sequence of TYAMG (SEQ ID NO: 4), a CDR H2 having the sequence of SIGASGSQTRYADS (SEQ ID NO: 8), and a CDR H3 having the sequence of LAIGDSY (SEQ ID NO: 11).

In some embodiments, the light chain of the isolated antibody of the invention comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS.

In some embodiments, the heavy chain of the isolated antibody of the invention comprises a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In other embodiments, the heavy chain of the isolated antibody of the invention comprises a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In other embodiments, the heavy chain of the isolated antibody of the invention comprises a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments, the heavy chain of the isolated antibody of the invention comprises a sequence having at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In other embodiments, the heavy chain of the isolated antibody of the invention comprises a sequence having at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

-continued

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain and a heavy chain, wherein the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain comprises a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain and a heavy chain, wherein the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain comprises a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

-continued

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain and a heavy chain, wherein the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain comprises a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain and a heavy chain, wherein the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain comprises a sequence having at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

-continued

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In yet another aspect, the invention features an isolated antibody containing a light chain and a heavy chain, wherein the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;

and the heavy chain comprises a sequence having at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments, the heavy chain of the isolated antibody of the invention comprises a sequence having at least 95%, 97%, 99%, or 100% identity to the sequence of any one of SEQ ID NOs: 20-24. In other embodiments, the light chain of the isolated antibody of the invention comprises a sequence having at least 95%, 97%, 99%, or 100% identity to the sequence of SEQ ID NO: 19.

In some embodiments, the isolated antibody of the invention further includes amino acid substitution N297A, relative to the sequence of any one of SEQ ID NOs: 20-24.

In other embodiments, the isolated antibody further includes amino acid substitutions D355E and L357M, relative to the sequence of any one of SEQ ID NOs: 20-24.

In other embodiments, the isolated antibody of the invention further includes any one or more of the following amino acid substitutions: A23V, S30R, L80V, A84T, E85D, A93V, relative to the sequence of any one of SEQ ID NOs: 20-24 and Q38H, V58I, and G99D, relative to the sequence of SEQ ID NO: 19.

In yet other embodiment, the isolated antibody of the invention does not contain a C-terminal lysine at residue 446, relative to the sequence of any one of SEQ ID NOs: 20-24.

In some embodiments, the antibody of any of the above aspects binds human FcRn with a $K_D$ that is less than or equal to that of an antibody having the light chain variable region and heavy chain variable region of N022, N023, N024, N026, or N027 and also having the same Fc region as that of the antibody being compared. For example, in a particular $K_D$ assay, the $K_D$ of the antibody is less than 200, 150, 100, 50, or 40 pM.

The amino acid positions assigned to complementary determining regions (CDRs) and framework regions (FRs) of any isolated antibody described herein are defined according to EU index of Kabat (Sequences of Proteins of Immunological Interest, 5th Ed. Public Health Service, National Institutes of Health, Bethesda, Md. (1991)).

In another aspect, the invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

-continued
VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In yet another aspect, the invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments of any of the above aspects, the isolated antibody of the invention is a monoclonal antibody. In some embodiments, the isolated antibody is IgG1. In some embodiments, the isolated antibody includes a λ light chain. In some embodiments, the isolated antibody includes a kappa light chain.

In some embodiments of any of the above aspects, the isolated antibody of the invention is a humanized or fully human antibody.

In some embodiments, the isolated antibody binds to human FcRn with a $K_D$ of 1-100, 5-150, 5-100, 5-75, 5-50, 10-50, or 10-40 pM.

In some embodiments, the isolated antibody of the invention binds rodent, e.g., mouse or rat FcRn. In some embodiments, the isolated antibody of the invention binds rodent, e.g., mouse or rat, FcRn with a $K_D$ of less than 200, 150, 100, 50, or 40 pM.

In another aspect, the invention features a nucleic acid molecule encoding any isolated antibody described herein.

In yet another aspect, the invention features a vector containing a nucleic acid molecule encoding any antibody described herein.

In another aspect, the invention features a host cell that expresses any isolated antibody described herein. The host cell includes a nucleic acid molecule encoding any isolated antibody described herein or a vector containing a nucleic acid molecule encoding any isolated antibody described herein, wherein the nucleic acid molecule or vector is expressed by the host cell.

In some embodiments, the host cell is a Chinese hamster ovary (CHO) cell. In some embodiment, the host cell is an Sp2 cell or NS0 cell.

In another aspect, the invention features a method of preparing any isolated antibody described herein. The method includes: a) providing a host cell that includes a nucleic acid molecule encoding any isolated antibody described herein or a vector containing a nucleic acid molecule encoding any isolated antibody described herein, and b) expressing the nucleic acid molecule or vector in the host cell under conditions that allow for the formation of the antibody.

In some embodiments, the method includes the step of recovering the antibody from the host cell, e.g., at a concentration of about 1-100, 1-50, 1-25, 2-50, 5-50, or 2-20 mg/ml.

In other embodiments, the host cell used in the method is a CHO cell.

In another aspect, the invention features a pharmaceutical composition including any isolated antibody described herein and one or more pharmaceutically acceptable carriers or excipients.

In some embodiments, the pharmaceutical composition includes the antibody in a therapeutically effective dose amount.

In another aspect, the invention features a method of increasing IgG catabolism in a subject. In another aspect, the invention features a method of reducing autoantibodies in a subject. In yet another aspect, the invention features a method of treating or reducing an immune complex-based activation of an immune response in a subject. The methods include administering to the subject any isolated antibody described herein or a pharmaceutical composition including any isolated antibody described herein.

In some embodiments, the immune response in the subject is an acute or chronic immune response.

In some embodiments, the subject has or the acute immune response is activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura (ITP), autoimmune haemolytic anaemia (AIHA), immune neutropenia, dilated cardiomyopathy, and serum sickness.

In some embodiments, the subject has or the chronic immune response is activated by a medical condition selected from the group consisting of chronic inflammatory demyelinating polyneuropathy (CIDP), systemic lupus, a chronic form of a disorder indicated for acute treatment, reactive arthropathies, primary biliary cirrhosis, ulcerative colitis, and antineutrophil cytoplasmic antibody (ANCA)-associated vasculitis.

In some embodiments, the subject has or the immune response is activated by an autoimmune disease. In particular, the autoimmune disease is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence having no more than two amino acid substitutions relative to the sequence of TGTGSDVGSYNLVS (SEQ ID NO: 1), the CDR L2 comprises, consists of, or consists essentially of a sequence having no more than one amino acid substitutions relative to the sequence of GDSERPS (SEQ ID NO: 2), the CDR L3 comprises, consists of, or consists essentially of a sequence having no more than one amino acid substitutions relative to the sequence of SSYAGSGIYV (SEQ ID NO: 3), the CDR H1 comprises, consists of, or consists essentially of a sequence having no more than one amino acid substitutions relative to the sequence of TYAMG (SEQ ID NO: 4), DYAMG (SEQ ID NO: 5), or NYAMG (SEQ ID NO: 6), the CDR H2 comprises, consists of, or consists essentially of a sequence having no more than two amino acid substitutions relative to the sequence of SIGSSGAQTRYADS (SEQ ID NO: 7), SIGASGSQTRYADS (SEQ ID NO: 8), SIGASGAQTRYADS (SEQ ID NO: 9), or SIGASGGQTRYADS (SEQ ID NO: 10), and the CDR H3 comprises, consists of, or consists essentially of a sequence having no more than one amino acid substitutions relative to the sequence of LAIGDSY (SEQ ID NO: 11).

In some embodiments of all aspects, the antibody binds human FcRn with a KD of less than or equal to that of antibody N026.

In some embodiments of all aspects, the CDR L1 comprises, consists of, or consists essentially of the sequence TGTGSDVGSYNLVS (SEQ ID NO: 1), the CDR L2 comprises, consists of, or consists essentially of the sequence GDSERPS (SEQ ID NO: 2), the CDR L3 comprises, consists of, or consists essentially of the sequence SSYAGSGIYV (SEQ ID NO: 3), the CDR H1 comprises, consists of, or consists essentially of the sequence TYAMG (SEQ ID NO: 4), the CDR H2 comprises, consists of, or consists essentially of the sequence SIGSSGAQTRYADS (SEQ ID NO: 7), and the CDR H3 comprises, consists of, or consists essentially of the sequence LAIGDSY (SEQ ID NO: 11).

In some embodiments of all aspects, the CDR L1 comprises, consists of, or consists essentially of the sequence TGTGSDVGSYNLVS (SEQ ID NO: 1), the CDR L2 comprises, consists of, or consists essentially of the sequence GDSERPS (SEQ ID NO: 2), the CDR L3 comprises, consists of, or consists essentially of the sequence SSYAGSGIYV (SEQ ID NO: 3), the CDR H1 comprises, consists of, or consists essentially of the sequence DYAMG (SEQ ID NO: 5), the CDR H2 comprises, consists of, or consists essentially of the sequence SIGASGSQTRYADS (SEQ ID NO: 8), and the CDR H3 comprises, consists of, or consists essentially of the sequence LAIGDSY (SEQ ID NO: 11).

In some embodiments of all aspects, the CDR L1 comprises, consists of, or consists essentially of the sequence TGTGSDVGSYNLVS (SEQ ID NO: 1), the CDR L2 comprises, consists of, or consists essentially of the sequence GDSERPS (SEQ ID NO: 2), the CDR L3 comprises, consists of, or consists essentially of the sequence SSYAGSGIYV (SEQ ID NO: 3), the CDR H1 comprises, consists of, or consists essentially of the sequence NYAMG (SEQ ID NO: 6), the CDR H2 comprises, consists of, or consists essentially of the sequence SIGASGAQTRYADS (SEQ ID NO: 9), and the CDR H3 comprises, consists of, or consists essentially of the sequence LAIGDSY (SEQ ID NO: 11).

In some embodiments of all aspects, the CDR L1 comprises, consists of, or consists essentially of the sequence TGTGSDVGSYNLVS (SEQ ID NO: 1), the CDR L2 comprises, consists of, or consists essentially of the sequence GDSERPS (SEQ ID NO: 2), the CDR L3 comprises, consists of, or consists essentially of the sequence SSYAGSGIYV (SEQ ID NO: 3), the CDR H1 comprises, consists of, or consists essentially of the sequence TYAMG (SEQ ID NO: 4), the CDR H2 comprises, consists of, or consists essentially of the sequence SIGASGGQTRYADS (SEQ ID NO: 10), and the CDR H3 comprises, consists of, or consists essentially of the sequence LAIGDSY (SEQ ID NO: 11).

In some embodiments of all aspects, the CDR L1 comprises, consists of, or consists essentially of the sequence TGTGSDVGSYNLVS (SEQ ID NO: 1), the CDR L2 comprises, consists of, or consists essentially of the sequence GDSERPS (SEQ ID NO: 2), the CDR L3 comprises, consists of, or consists essentially of the sequence SSYAGSGIYV (SEQ ID NO: 3), the CDR H1 comprises, consists of, or consists essentially of the sequence TYAMG (SEQ ID NO: 4), the CDR H2 comprises, consists of, or consists essentially of the sequence SIGASGSQTRYADS (SEQ ID NO: 8), and the CDR H3 comprises, consists of, or consists essentially of the sequence LAIGDSY (SEQ ID NO: 11).

In some embodiments of all aspects, the subject has a history of having had a previous fetal and neonatal alloimmune and/or autoimmune disorder. For example, in some embodiments the pregnant subject has previously had a pregnancy wherein the fetus or neonate has had a fetal and neonatal alloimmune and/or autoimmune disorder. In some embodiments of all aspects, the subject is at risk of having a fetal and neonatal alloimmune and/or autoimmune disorder.

In some embodiments of all aspects, the fetal and neonatal alloimmune and/or autoimmune disorder is selected from the group consisting of fetal and neonatal alloimmune thrombocytopenia, hemolytic disease of the fetus and newborn, alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma, Behcet's disease, neonatal Graves' disease, neonatal Kawasaki disease, neonatal autoimmune thyroid disease, and neonatal type I diabetes mellitus. In some embodiments of all aspects, the fetal and neonatal autoimmune and/or autoimmune disorder is hemolytic disease of the fetus and newborn. In some embodiments of all aspects, the fetal and neonatal autoimmune and/or autoimmune disorder is fetal and neonatal alloimmune thrombocytopenia. In some embodiments of all aspects, the fetal and neonatal autoimmune and/or autoimmune disorder is congenital heart block.

In some embodiments of all aspects, treatment reduces the risk of a miscarriage.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence $X_1$GTGSDVGSYN$X_2$VS (SEQ ID NO: 12), the CDR L2 comprises, consists of, or consists essentially of a sequence GD$X_3X_4$RPS (SEQ ID NO: 13), the CDR L3 comprises, consists of, or consists essentially of a sequence $X_5$SY$X_6$GSGIYV (SEQ ID NO: 14), the CDR H1 comprises, consists of, or consists essentially of a sequence $Z_1$YAMG (SEQ ID NO: 15), the CDR H2 comprises, consists of, or consists essentially of a sequence SIG$Z_2$SG$Z_3$QT$Z_4$YADS (SEQ ID NO: 16), the CDR H3 comprises, consists of, or consists essentially of a sequence LA$Z_5Z_6$DSY (SEQ ID NO: 17), wherein $X_1$ is a polar or hydrophobic amino acid, $X_2$ is a hydrophobic amino acid, $X_3$ is a polar amino acid, $X_4$ is a polar or acidic amino acid, $X_5$ is a polar or hydrophobic amino acid, $X_6$ is a hydrophobic amino acid, $Z_1$ is a polar or acidic amino acid, $Z_2$ is a polar or hydrophobic amino acid, $Z_3$ is G, S, or A, $Z_4$ is a basic amino acid, $Z_5$ is a hydrophobic or basic amino acid, and $Z_6$ is G, S, D, Q, or H, and wherein the antibody binds human FcRn with a KD of less than 200, 150, 100, 50, or 40 pM.

In some embodiments of all aspects, the CDR L1 comprises, consists of, or consists essentially of a sequence $X_1$GTGSDVGSYN$X_2$VS (SEQ ID NO: 12), the CDR L2 comprises, consists of, or consists essentially of a sequence GD$X_3X_4$RPS (SEQ ID NO: 13), the CDR L3 comprises, consists of, or consists essentially of a sequence $X_5$SY$X_6$GSGIYV (SEQ ID NO: 14), the CDR H1 comprises, consists of, or consists essentially of a sequence $Z_1$YAMG (SEQ ID NO: 15), the CDR H2 comprises, consists of, or consists essentially of a sequence SIG$Z_2$SG$Z_3$QT$Z_4$YADS (SEQ ID NO: 16), the CDR H3 comprises, consists of, or consists essentially of a sequence LA$Z_5Z_6$DSY (SEQ ID NO: 17), wherein $X_1$ is T, A, S, or I; $X_2$ is L or I; $X_3$ is S, N, or T; $X_4$ is Q, E, or N; $X_5$ is C, S, I, or Y; $X_6$ is A or V; $Z_1$ is E, T, D, or N; $Z_2$ is S or A; $Z_3$ is G, S, or A; $Z_4$ is K or R; $Z_5$ is I, L, or H; and $Z_6$ is G, S, D, Q, or H.

In some embodiments of all aspects, the CDR L1 comprises, consists of, or consists essentially of a sequence having no more than two amino acid substitutions relative to the sequence of TGTGSDVGSYNLVS (SEQ ID NO: 1), the CDR L2 comprises, consists of, or consists essentially of a sequence having no more than one amino acid substitutions relative to the sequence of GDSERPS (SEQ ID NO: 2), the CDR L3 comprises, consists of, or consists essentially of a sequence having no more than one amino acid substitutions relative to the sequence of SSYAGSGIYV (SEQ ID NO: 3), the CDR H1 comprises, consists of, or consists essentially of a sequence having no more than one amino acid substitutions relative to the sequence of TYAMG (SEQ ID NO: 4), DYAMG (SEQ ID NO: 5), or NYAMG (SEQ ID NO: 6), the CDR H2 comprises, consists of, or consists essentially of a sequence having no more than two amino acid substitutions relative to the sequence of SIGSSGAQTRYADS (SEQ ID NO: 7), SIGASGSQTRYADS (SEQ ID NO: 8), SIGASGAQTRYADS (SEQ ID NO: 9), or SIGASGGQTRYADS (SEQ ID NO: 10), and the CDR H3 comprises, consists of, or consists essentially of a sequence having no more than one amino acid substitutions relative to the sequence of LAIGDSY (SEQ ID NO: 11).

In some embodiments of all aspects, the subject has a history of having had a previous fetal and neonatal alloimmune and/or autoimmune disorder. For example, in some embodiments, the pregnant subject has had a previous pregnancy wherein the fetus or neonate had a fetal and neonatal alloimmune and/or autoimmune disorder. In some embodiments of all aspects, the subject is at risk of having a fetal and neonatal alloimmune and/or autoimmune disorder.

In some embodiments of all aspects, the fetal and neonatal alloimmune and/or autoimmune disorder is selected from the group consisting of fetal and neonatal alloimmune thrombocytopenia, hemolytic disease of the fetus and newborn, alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma, Behcet's disease, neonatal Graves' disease, neonatal Kawasaki disease, neonatal autoimmune thyroid disease, and neonatal type I diabetes mellitus. In some embodiments of all aspects, the fetal and neonatal autoimmune and/or autoimmune disorder is hemolytic disease of the fetus and newborn. In some embodiments of all aspects, the fetal and neonatal autoimmune and/or autoimmune disorder is fetal and neonatal alloimmune thrombocytopenia. In some embodiments of all aspects, the fetal and neonatal autoimmune and/or autoimmune disorder is congenital heart block. In some embodiments of all aspects, treatment reduces the risk of a miscarriage.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain variable region comprising, consisting of, or consisting essentially of a CDR L1 having the sequence TGTGSDVGSYNLVS (SEQ ID NO: 1), a CDR L2 having the sequence GDSERPS (SEQ ID NO: 2), and a CDR L3 having the sequence SSYAGSGIYV (SEQ ID NO: 3), and a heavy chain variable region comprising, consisting of, or consisting essentially of a CDR H1, a CDR H2, and a CDR H3, wherein the CDR H1 comprises, consists of, or consists essentially of a sequence Z1YAMG (SEQ ID NO: 15), the CDR H2 comprises, consists of, or consists essentially of a sequence SIGZ2SGZ3QTRYADS (SEQ ID NO: 18), and the CDR H3 comprises, consists of, or consists essentially of the sequence LAIGDSY (SEQ ID NO: 11), and wherein Z1 is T, D, or N; Z2 is S or A; and Z3 is G, S or A.

In some embodiments of all aspects, the light chain comprises, consists of, or consists essentially of a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS.

In some embodiments of all aspects, the heavy chain comprises, consists of, or consists essentially of a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments of all aspects, the heavy chain comprises, consists of, or consists essentially of a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments of all aspects, the heavy chain comprises, consists of, or consists essentially of a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

In some embodiments of all aspects, the heavy chain comprises, consists of, or consists essentially of a sequence having at least 90% identity to the sequence of (SEQ ID NO: 23)
EVQLLESGGGLVQPGGSLRLSCAASGFTFSTYAMGWVRQAPGKGLEWVSS
IGASGGQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

In some embodiments of all aspects, the heavy chain comprises, consists of, or consists essentially of a sequence having at least 90% identity to the sequence of (SEQ ID NO: 24)
EVQLLESGGGLVQPGGSLRLSCAASGFTFSTYAMGWVRQAPGKGLEWVSS
IGASGSQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSREEMTKNQVSLTCLVKGFYPSDIAVEWESNGQPENNYKTTPPVLDSD
GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of a sequence having at least 90% identity to the sequence of (SEQ ID NO: 19)
QSALTQPASVSGSPGQSITISCTGTGSDVGSYNLVSWYQQHPGKAPKLMI
YGDSERPSGVSNRFSGSKSGNTASLTISGLQAEDEADYYCSSYAGSGIYV
FGTGTKVTVLGQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS;
and the heavy chain comprises, consists of,
or consists essentially of a sequence having
at least 90% identity to the sequence of (SEQ ID NO: 20)
EVQLLESGGGLVQPGGSLRLSCAASGFTFSTYAMGWVRQAPGKGLEWVSS
IGSSGAQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of a sequence having at least 90% identity to the sequence of (SEQ ID NO: 19)
QSALTQPASVSGSPGQSITISCTGTGSDVGSYNLVSWYQQHPGKAPKLMI
YGDSERPSGVSNRFSGSKSGNTASLTISGLQAEDEADYYCSSYAGSGIYV
FGTGTKVTVLGQPKAAPSVTLFPPSSEELQANKATLVCLISDFYPGAVTV
AWKADSSPVKAGVETTTPSKQSNNKYAASSYLSLTPEQWKSHKSYSCQVT
HEGSTVEKTVAPTECS;
and the heavy chain comprises, consists of, or
consists essentially of a sequence having
at least 90% identity to the sequence of (SEQ ID NO: 21)
EVQLLESGGGLVQPGGSLRLSCAASGFTFSDYAMGWVRQAPGKGLEWVSS
IGASGSQTRYADSVKGRFTISRDNSKNTLYLQMNSLRAEDTAVYYCARLA
IGDSYWGQGTMVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYASTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or
consists essentially of a sequence having
at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or
consists essentially of a sequence having
at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or
consists essentially of a sequence having
at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments of all aspects, the heavy chain comprises, consists of, or consists essentially of a sequence having at least 95%, 97%, 99%, or 100% identity to the sequence of any one of SEQ ID NOs: 20-24. In some embodiments of all aspects, the light chain comprises, consists of, or consists essentially of a sequence having at least 95%, 97%, 99%, or 100% identity to the sequence of SEQ ID NO: 19.

In some embodiments of all aspects, the antibody further comprises, consists of, or consists essentially of amino acid substitution N297A, relative to the sequence of any one of SEQ ID NOs: 20-24. In some embodiments of all aspects, the antibody further comprises, consists of, or consists essentially of amino acid substitutions D355E and L357M, relative to the sequence of any one of SEQ ID NOs: 20-24. In some embodiments of all aspects, the antibody further comprises, consists of, or consists essentially of any one or more of the following amino acid substitutions: A23V, S30R, L80V, A84T, E85D, A93V, relative to the sequence of any one of SEQ ID NOs: 20-24 and Q38H, V58I, and G99D, relative to the sequence of SEQ ID NO: 19.

In some embodiments of all aspects, the antibody does not contain a C-terminal lysine at residue 446, relative to the sequence of any one of SEQ ID NOs: 20-24.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or consists essentially of the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or consists essentially of the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or consists essentially of the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or consists essentially of the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In another aspect, the invention features a method of treating a fetal and neonatal alloimmune and/or autoimmune disorder comprising, consisting of, or consisting essentially of administering an antibody to a pregnant subject, wherein the antibody comprises, consists of, or consists essentially of a light chain and a heavy chain, wherein the light chain comprises, consists of, or consists essentially of the sequence of

```
                                        (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises, consists of, or
consists essentially of the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.
```

In another aspect, the invention features a method of treating fetal anemia associated with hemolytic disease of the fetus and newborn, comprising, consisting of, or consisting essentially of administering an antibody to a pregnant subject, wherein the antibody comprises, consists of, or consists essentially of: (1) a light chain comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15), the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17); wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of treating fetal anemia associated with hemolytic disease of the fetus and newborn, comprising, consisting of, or consisting essentially of administering an antibody to a pregnant subject, wherein the antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of treating fetal anemia associated with hemolytic disease of the fetus and newborn, comprising, consisting of, or consisting essentially of administering an antibody to a pregnant subject, wherein the antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In some embodiments of all aspects, the method treats the pregnant subject, a fetus of the pregnant subject, and/or a combination thereof.

In another aspect, the invention features a method of treating an autoimmune disorder, comprising, consisting of, or consisting essentially of administering an antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15); the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17); wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of treating an autoimmune disorder, comprising, consisting of, or consisting essentially of administering an antibody to a pregnant subject, wherein the antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of treating an autoimmune disorder, comprising, consisting of, or consisting essentially of administering an antibody to a pregnant subject, wherein the antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In some embodiments of all aspects, the autoimmune disorder is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

In some embodiments of all aspects, the treatment reduces the risk of miscarriage/loss of fetus.

In another aspect, the invention features a method of reducing the risk of or reducing the risk of developing an autoimmune or alloimmune disorder, comprising, consisting of, or consisting essentially of administering an FcRn antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15); the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17); wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of reducing the risk of or reducing the risk of developing an autoimmune or alloimmune disorder, comprising, consisting of, or consisting essentially of administering an FcRn antibody to a pregnant subject, wherein the antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of reducing the risk of or reducing the risk of developing an autoimmune or alloimmune disorder, comprising, consisting of, or consisting essentially of administering an FcRn antibody to a pregnant subject, wherein the antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In some embodiments of all aspects, the autoimmune disorder is selected from the group consisting of alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

In some embodiments of all aspects, the treatment reduces the risk of miscarriage/loss of fetus.

In another aspect, the invention features a method of increasing antibody catabolism in a subject, the method comprising, consisting of, or consisting essentially of administering an antibody to a pregnant subject, wherein the administered antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15); the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17); wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of increasing antibody catabolism in a subject, the method comprising, consisting of, or consisting essentially of administering an antibody to a pregnant subject, wherein the administered antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of increasing antibody catabolism in a subject, the method comprising, consisting of, or consisting essentially of administering an antibody to a pregnant subject, wherein the administered antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In some embodiments of all aspects, increasing antibody catabolism comprises increasing pathogenic antibody catabolism. In some embodiments of all aspects, the pathogenic antibody is pathogenic to the mother, the fetus, or both the mother and the fetus. In some embodiments of all aspects, the pathogenic antibody is an IgG antibody. In some embodiments of all aspects, the antibody causes a fetal and neonatal alloimmune and/or autoimmune disorder in a fetus in the pregnant subject.

In some embodiments of all aspects, the fetal and neonatal alloimmune and/or autoimmune disorder is selected from the group consisting of fetal and neonatal alloimmune thrombocytopenia hemolytic disease of the fetus and newborn, alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma, Behcet's disease, neonatal Graves' disease, neonatal Kawasaki disease, neonatal autoimmune thyroid disease, and neonatal type I diabetes mellitus.

In another aspect, the invention features a method of reducing autoantibodies in a subject, the method comprising, consisting of, or consisting essentially of administering an antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15); the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17), wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of reducing autoantibodies in a subject, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of reducing autoantibodies in a subject, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In another aspect, the invention features a method of reducing an immune complex-based activation of an immune response in a subject, the method comprising, consisting of, or consisting essentially of administering an antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15); the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17); wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of reducing an immune complex-based activation of an immune response in a subject, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of reducing an immune complex-based activation of an immune response in a subject, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In some embodiments of all aspects, the immune response is an acute or chronic immune response in the subject.

In some embodiments of all aspects, the acute immune response is activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dilated cardiomyopathy, and serum sickness. For example, in some embodiments, the acute immune response is activated by a medical condition in the pregnant subject. For example, in some embodiments, the acute immune response is activated in the fetus or neonate by a medical condition in the pregnant subject. In some embodiments of all aspects, the acute immune response is activated by a medical condition in the pregnant subject. In some embodiments of all aspects, the acute immune response is activated in the fetus or neonate by a medical condition in the pregnant subject. In some embodiments of all aspects, the acute immune response is activated by idiopathic thrombocytopenia purpura. In some embodiments of all aspects, the acute immune response is activated by pemphigus vulgaris. In some embodiments of all aspects, the acute immune response is activated by catastrophic anti-phospholipid antibody syndrome. In some embodiments of all aspects, the acute immune response is activated by neuromyelitis optica. In some embodiments of all aspects, the acute immune response is activated by antibody-mediated rejection. In some embodiments of all aspects, the acute immune response is activated by myasthenia gravis.

Also described herein is a method of treating a fetal and neonatal alloimmune and/or autoimmune disorder comprising, consisting of, or consisting essentially of administering M281 (e.g., at a dose of 15 mg/kg or 30 mg/kg, e.g., a weekly dose) to a pregnant subject and ceasing administration if the subject exhibits hypoalbuminemia (e.g., a serum albumin level below 30 g/l, 25 g/l, 20 g/l). Also described is method comprising, consisting of, or consisting essentially of treating a fetal and neonatal alloimmune and/or autoimmune disorder comprising administering M281 to a pregnant subject (e.g., at a dose of 15 mg/kg or 30 mg/kg, e.g., a weekly dose) and administering albumin if the subject exhibits hypoalbuminemia (e.g., a serum albumin level below 30 g/l, 25 g/l, 20 g/l). Also described is method comprising, consisting of, or consisting essentially of treating a fetal and neonatal alloimmune and/or autoimmune disorder comprising administering M281 to a pregnant subject (e.g., at a dose of 15 mg/kg or 30 mg/kg, e.g., a weekly dose) and administering a hyperosmolar solution (e.g., mannitol or other solution known in the art) if the subject exhibits hypoalbuminemia (e.g., a serum albumin level below 30 g/l, 25 g/l, 20 g/1). Also described is a method comprising, consisting of, or consisting essentially of treating a fetal and neonatal alloimmune and/or autoimmune disorder comprising administering M281 (e.g., at a dose of 15 mg/kg or 30 mg/kg, e.g., a weekly dose) to a pregnant subject and testing the serum albumin level of the subject at least once prior to or subsequent to administration of M281. In some cases of this method, administration of M281 can be continued or not.

In some embodiments of all aspects, the chronic immune response is activated by a medical condition selected from the group consisting of chronic inflammatory demyelinating polyneuropathy (CIDP), systemic lupus, reactive arthropathies, primary biliary cirrhosis, ulcerative colitis, and anti-neutrophil cytoplasmic antibody-associated vasculitis. In some embodiments of all aspects, the chronic immune response is activated by chronic inflammatory demyelinating polyneuropathy.

In some embodiments of all aspects, the subject has an autoimmune disease. In some embodiments of all aspects, the autoimmune disease is selected from the group consisting of alopecia areata, ankylosing spondylitis, antiphospholipid syndrome, Addison's disease, hemolytic anemia, warm autoimmune hemolytic anemia, anti-factor antibodies, heparin induced thrombocytopenia (sensitized transplant, autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis. In some embodiments of all aspects, the autoimmune disease is warm autoimmune hemolytic anemia. In some embodiments of all aspects, the autoimmune disease is anti-factor antibodies. In some embodiments of all aspects, the autoimmune disease heparin induced thrombocytopenia. In some embodiments of all aspects, the autoimmune disease is sensitized transplant.

In another aspect, the invention features a method of decreasing antibody transport across the placenta of a pregnant subject, the method comprising, consisting of, or consisting essentially of administering an antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15), the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17); wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of decreasing antibody transport across the placenta of a pregnant subject, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of decreasing antibody transport across the placenta of a pregnant subject, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In another aspect, the invention features a method of treating an antibody-mediated enhancement of viral disease in a fetus or a neonate, the method comprising, consisting of, or consisting essentially of administering an antibody to a pregnant subject, wherein the antibody comprises, consists of, or consists essentially of: (1) a light chain variable region comprising, consisting of, or consisting essentially of a CDR L1, a CDR L2, and a CDR L3 and (2) a heavy chain variable region comprising, consisting of, or consisting essentially of a CDR H1, a CDR H2, and a CDR H3, wherein the CDR L1 comprises, consists of, or consists essentially of a sequence X1GTGSDVGSYNX2VS (SEQ ID NO: 12); the CDR L2 comprises, consists of, or consists essentially of a sequence GDX3X4RPS (SEQ ID NO: 13); the CDR L3 comprises, consists of, or consists essentially of a sequence X5SYX6GSGIYV (SEQ ID NO: 14); the CDR H1 comprises, consists of, or consists essentially of a sequence Z1YAMG (SEQ ID NO: 15); the CDR H2 comprises, consists of, or consists essentially of a sequence SIGZ2SGZ3QTZ4YADS (SEQ ID NO: 16); the CDR H3 comprises, consists of, or consists essentially of a sequence LAZ5Z6DSY (SEQ ID NO: 17); wherein X1 is T, A, S, or I; X2 is L or I; X3 is S, N, or T; X4 is Q, E, or N; X5 is C, S, I, or Y; X6 is A or V; Z1 is E, T, D, or N; Z2 is S or A; Z3 is G, S, or A; Z4 is K or R; Z5 is I, L, or H; and Z6 is G, S, D, Q, or H.

In another aspect, the invention features a method of treating an antibody-mediated enhancement of viral disease in a fetus or a neonate, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of a sequence having at least 90% identity to the sequence of SEQ ID NO: 19; and the heavy chain comprises, consists of, or consists essentially of a sequence having at least 90% identity to the sequence selected from the group consisting of SEQ ID NO: 20, SEQ ID NO: 21, SEQ ID NO: 22, SEQ ID NO: 23, and SEQ ID NO: 24.

In another aspect, the invention features a method of treating an antibody-mediated enhancement of viral disease in a fetus or a neonate, the method comprising, consisting of, or consisting essentially of administering an antibody to a pregnant subject, wherein the antibody comprises, consists of, or consists essentially of: a light chain and a heavy chain, wherein the light chain comprises, consists of, or consists essentially of the sequence of SEQ ID NO: 19; and the heavy chain comprises, consists of, or consists essentially of the sequence selected from the group consisting of SEQ ID NO: 20, SEQ ID NO: 21, SEQ ID NO: 22, SEQ ID NO: 23, and SEQ ID NO: 24.

In some embodiments of all aspects, the viral disease is caused by a virus selected from the group consisting of an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, enterovirus infection, cytomegalovirus infection, pneumovirus infection, morbillivirus infection, and measles virus infection.

In some embodiments of all aspects, the pregnant subject has or is at risk of having a medical condition that activates an immune response in the pregnant subject. In some embodiments of all aspects, the medical condition is pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dialated cardiomyopathy, serum sickness, chronic inflammatory demyelinating polyneuropathy, systemic lupus, reactive arthropathies, primary biliary cirrhosis, ulcerative colitis, antineutrophil cytoplasmic antibody (ANCA)-associated vasculitis, alopecia areata, ankylosing spondylitis, antiphospholipid syndrome, Addison's disease, hemolytic anemia, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In some embodiments of all aspects, the pregnant subject has a history of having had a previous fetus or neonate that had a fetal and neonatal alloimmune and/or autoimmune disorder. For example, in some embodiments, the pregnant subject has had a previous pregnancy, wherein the fetus or neonate had a fetal and neonatal alloimmune and/or autoimmune disorder.

In some embodiments of all aspects, an antibody associated with an immune disease is detected in a biological sample obtained from the pregnant subject. In some embodiments of all aspects, the biological sample is a blood or urine sample. In some embodiments of all aspects, the biological sample is a blood sample.

In some embodiments of all aspects, the administered antibody is a monoclonal antibody. In some embodiments of all aspects, the administered antibody is IgG1. In some embodiments of all aspects, the administered antibody comprises, consists of, or consists essentially of a λ light chain.

In another aspect, the invention features a method for treating or reducing the risk of developing a fetal and neonatal alloimmune and/or autoimmune disorder, the method including: administering to a pregnant woman a composition comprising an antibody comprising a light chain having the amino acid sequence of SEQ ID NO:19 and a heavy chain having the amino acid sequence of SEQ ID NO:24 (M281), wherein the administration of M281 ceases after week 34 gestational age.

In another aspect, the invention features a method for treating or reducing the risk of developing a fetal and neonatal alloimmune and/or autoimmune disorder comprising administering to a pregnant woman a composition comprising an antibody comprising a light chain having the amino acid sequence of SEQ ID NO:19 and a heavy chain having the amino acid sequence of SEQ ID NO:24 (M281), wherein the administration of M281 ceases at least one week prior to birth.

In various aspects of both methods, the method includes: administering IVIG to the pregnant women after cessation of administration of M281 and prior to birth (e.g., 40-100 hrs or 1-15 days prior to birth); administration of M281 ceases after gestational week 35; administration of M281 ceases prior to gestational week 36, 37 or 38; the IVIG is administered at 200 mg/kg-1000 mg/kg based on the weight of the pregnant women; M281 is administered at 30 mg/kg based on the weight of the pregnant women; M281 is administered at 15 mg/kg based on the weight of the pregnant women; the dose is dose per administration and is based on the weight of the pregnant women at first dosing and is not adjusted upward based on weight gain by the pregnant women; the dose is dose per administration and is based on the weight of the pregnant women at first dosing and is adjusted upward based on weight gain by the pregnant woman; the composition is administered at least every other week; the composition is administered every other week;

the composition is administered at least every week; the composition is administered every week; administration is begun during the first trimester of pregnancy; administration is begun during the second trimester of pregnancy; administration is begun during the third trimester of pregnancy; the route of administration is intravenous; the pregnant women has an obstetrical history of severe fetal anemia; the pregnant women has an elevated anti RhD, anti-Rhc or anti Kell immunoglobulin alloantibody titer; the pregnant women has an elevated anti-Rhc or anti-Kell immunoglobulin alloantibody titer; the pregnant women has an elevated immunoglobulin alloantibody titer for one or more antibodies selected from the group consisting of anti-Lua, Lub, Bg, Kna, Yta, E. c. K. Cw, Fya, cE, ce, D, Ce, cE, K, Kpa, Kpb, Fya, M, N, S, Lea, Leb, Fy, Jka. Diego, P and Mia/Mur; the pregnant women has an obstetrical history of severe fetal anemia or stillbirth at 524 weeks gestation and elevated anti-D or anti-Kell IgG alloantibody titers and is pregnant with an antigen-positive fetus; the first dosing is weeks 12 to 16 of pregnancy; the first dosing is during week 14 of pregnancy; and administration is begun during the first trimester of pregnancy.

Definitions

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit FcRn antigen-binding activity.

"Antibody fragments" comprise a portion of an intact antibody, preferably the antigen binding or variable region of the intact antibody. Examples of antibody fragments include Fab, Fab', F(ab')$_2$, and Fv fragments, diabodies, linear antibodies, single-chain antibody molecules, and multispecific antibodies.

As used herein, the term "isolated antibody" refers to an antibody which has been separated and/or recovered from a component of its manufacturing host cell environment. Contaminant components of its manufacturing host cell environment are materials which would interfere with research, diagnostic, or therapeutic uses of the antibody. Contaminant components may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or non-reducing conditions using, for example, Coomassie blue or silver stain. An isolated antibody includes the antibody in situ within recombinant cells. Ordinarily, however, an isolated antibody will be prepared by at least one purification step. A pharmaceutical preparation of an isolated antibody typically has less than 250 ppm (e.g., less than 200 ppm, 150 ppm. 100 ppm) of host cell proteins (HCP) as determined by an ELISA based HCP assay performed as recommended by an FDA "Guidance for Industry" document.

As used herein, the term "monoclonal antibody" refers to an antibody obtained from a population of substantially homogeneous antibodies, i.e., individual antibodies in the population have the same primary sequence except for possible naturally occurring mutations that may be present in minor amounts. Monoclonal antibodies are highly specific and directed against a single antigenic site (i.e., an epitope on human FcRn). In contrast to polyclonal antibody preparations which typically include different antibodies directed against different epitopes, each monoclonal antibody is directed against a single epitope on the antigen. The modifier "monoclonal" indicates the character of the antibody as being obtained from a substantially homogenous population of antibodies, and is not to be construed as requiring production of the antibody by any particular method.

As used herein, the terms "variable region" and "variable domain" refer to the portions of the light and heavy chains of an antibody that include amino acid sequences of complementary determining regions (CDRs, e.g., CDR L1, CDR L2, CDR L3, CDR H1, CDR H2, and CDR H3) and framework regions (FRs). According to the methods used in this invention, the amino acid positions assigned to CDRs and FRs are defined according to Kabat (Sequences of Proteins of Immunological Interest, 5th Ed. Public Health Service, National Institutes of Health, Bethesda, Md. (1991)). Using this numbering system, the actual linear amino acid sequence may contain fewer or additional amino acids corresponding to a shortening of, or insertion into, a CDR (defined further herein) or FR (defined further herein) of the variable region. For example, a heavy chain variable region may include a single inserted residue (i.e., residue 52a according to Kabat) after residue 52 of CDR H2 and inserted residues (i.e., residues 82a, 82b, 82c, etc. according to Kabat) after residue 82 of heavy chain FR. The Kabat numbering of residues may be determined for a given antibody by alignment at regions of homology of the sequence of the antibody with a "standard" Kabat numbered sequence.

As used herein, the terms "complementary determining regions" and "CDRs" refer to the regions of an antibody variable domain which are hypervariable in sequence and/or form structurally defined loops. A CDR is also known as a hypervariable region. The light chain and heavy chain variable regions each has three CDRs. The light chain variable region contains CDR L1, CDR L2, and CDR L3. The heavy chain variable region contains CDR H1, CDR H2, and CDR H3. Each CDR may include amino acid residues from a complementarity determining region as defined by Kabat (i.e. about residues 24-34 (CDR L1), 50-56 (CDR L2) and 89-97 (CDR L3) in the light chain variable region and about residues 31-35 (CDR H1), 50-65 (CDR H2) and 95-102 (CDR H3) in the heavy chain variable region.

As used herein, the term "FcRn" refers a neonatal Fc receptor that binds to the Fc region of an IgG antibody, e.g., an IgG1 antibody. An exemplary FcRn is human FcRn having UniProt ID No. P55899. Human FcRn is believed to be responsible for maintaining the half-life of IgG by binding and trafficking constitutively internalized IgG back to the cell surface for the recycling of IgG.

As used herein, the terms "affinity" and "binding affinity" refer to the strength of the binding interaction between two molecules. Generally, binding affinity refers to the strength of the sum total of non-covalent interactions between a single binding site of a molecule and its binding partner, such as an isolated antibody and its target (e.g., an isolated anti-FcRn antibody of the invention and a human FcRn). Unless indicated otherwise, binding affinity refers to intrinsic binding affinity, which reflects a 1:1 interaction between members of a binding pair. The binding affinity between two molecules is commonly described by the dissociation constant ($K_D$) or the affinity constant ($K_A$). Two molecules that have low binding affinity for each other generally bind slowly, tend to dissociate easily, and exhibit a large K. Two molecules that have high affinity for each other generally bind readily, tend to remain bound longer, and exhibit a small $K_D$. One method for determining the $K_D$ of an antibody to human FcRn is described in Example 2 ("the SPR method"). Using this method the $K_D$ of N022, N023, N024, N026, and N027 was 31, 31.4, 35.5, 36.5, and 19.3 pM, respectively.

As used herein, the term "inhibit IgG binding to FcRn" refers to the ability of an anti-FcRn antibody of the invention to block or inhibit the binding of IgG (e.g., IgG1) to human FcRn. In some embodiments, an anti-FcRn antibody of the invention binds FcRn, for example, at the site on human FcRn to which IgG binds. Thus, the anti-FcRn antibody of the invention is able to inhibit the binding of IgG (e.g., a subject's autoantibodies) to FcRn. In some embodiments, the molecule (e.g., an anti-FcRn antibody of the invention) substantially or completely inhibits binding to IgG. In some embodiments, the binding of IgG is reduced by 10%, 20%, 30%, 50%, 70%, 80%, 90%, 95%, or even 100%.

As used herein, the term "inhibit pathogenic antibody binding to FcRn" refers to the ability of an anti-FcRn antibody to block or inhibit the binding of a pathogenic antibody (e.g., pathogenic IgG antibody) to human FcRn. In some embodiments, an anti-FcRn antibody binds FcRn, for example, at the site on human FcRn to which the pathogenic antibody binds. Thus, the anti-FcRn antibody is able to inhibit the binding of pathogenic antibodies (e.g., pathogenic IgG antibodies) to FcRn. In some embodiments, the molecule (e.g., an anti-FcRn antibody) substantially or completely inhibits binding to pathogenic antibodies. In some embodiments, the binding of pathogenic antibodies to FcRn is reduced by 10%, 20%, 30%, 50%, 70%, 80%, 90%, 95%, or even 100%.

As used herein, the term "hydrophobic amino acid" refers to an amino acid having relatively low-water solubility. Hydrophobic amino acids include, but are not limited to, leucine, isoleucine, alanine, phenylalanine, valine, and proline. Particularly preferred hydrophobic amino acids in the present invention are alanine, leucine, isoleucine, and valine.

As used herein, the term "polar amino acid" refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids include, but are not limited to, serine, threonine, cysteine, methionine, tyrosine, tryptophan, asparagine, and glutamine. Particularly preferred polar amino acids in the present invention are serine, threonine, asparagine, glutamine, cysteine, and tyrosine.

As used herein, the term "acidic amino acid" refers to an amino acid whose side chain contains a carboxylic acid group having a pKa between 3.5 and 4.5. In some embodiments, acidic amino acids are aspartic acid and glutamic acid.

As used herein, the term "basic amino acid" refers to an amino acid whose side chain contains an amino group having a pKa between 9.5 and 13. In some embodiments, basic amino acids are histidine, lysine, and arginine.

As used herein, the term "percent (%) identity" refers to the percentage of amino acid (or nucleic acid) residues of a candidate sequence, e.g., an anti-FcRn antibody of the invention, that are identical to the amino acid (or nucleic acid) residues of a reference sequence, e.g., a wild-type anti-FcRn antibody, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100 \times (\text{fraction of A/B})$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position. A position may be altered by a substitution, deletion, or insertion. A substitution, deletion, or insertion may comprise a certain number of amino acids, (e.g., 1, 2, 3, 4, 5, 6, 7, 8, 9, 10, 11, 12, 13, 14, 15, or more). When describing a substitution, deletion, or insertion of no more than n amino acids, this is meant that the substitution, deletion, or insertion comprises, e.g., 1, 2, 3, 4, 5, 6, 7, 8, 9, 10, 11, 12, 13, 14, 15, . . . or n amino acids. The number or substitutions, deletions, or insertions can comprise a percent of the total sequence (e.g., 1%, 5%, 10%, 15%, 20%, or more) where the number of substitutions, deletions, or insertions alters 5%, 10%, 15%, 20% or more, of the amino acids in the total sequence.

As used herein, the term "fetal and neonatal alloimmune and/or autoimmune disorder" refers to an immune disorder in a fetus and/or neonate that is caused by the transplacental transfer of maternal antibodies (e.g., pathogenic maternal antibodies) directed against fetal and/or neonate antigens. For example, a pregnant subject's antibodies (e.g., pathogenic antibodies) may react against antigens in the fetus (e.g., antigens the fetus inherited from the fetus' father). Examples of fetal and neonatal alloimmune and/or autoimmune disorders are provided herein.

As used herein, the term "pathogenic antibody" refers to an antibody that causes one or more immune diseases or disorders in a subject (e.g., a pregnant subject), a fetus in a pregnant subject, and/or a neonate. In some embodiments, pathogenic antibodies are autoantibodies produced in a subject (e.g., a pregnant subject) against one or more of the subject's own proteins, thus causing autoimmune diseases or disorders in the subject. In some embodiments, pathogenic antibodies in a pregnant subject may transfer through the placenta to the fetus and react against antigens from the fetus (e.g., antigens that the fetus inherited from the fetus' father), thus causing, e.g., fetal and neonatal alloimmune and/or autoimmune disorders.

As used herein, the term "antibody-mediated enhancement of viral disease" refers to a viral disease in which antibodies can facilitate viral entry into host cells, thus leading to increased or enhanced infectivity in the cells. In some embodiments, an antibody may bind to a viral surface protein and the antibody/virus complex may bind to an FcRn receptor on a cell surface through interaction between the antibody and the receptor. Subsequently, the antibody/virus complex may be internalized into the cell.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (e.g., transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express one or more polypeptides encoding anti-FcRn antibodies of the invention.

As used herein, the term "vector" refers to a nucleic acid molecule capable of transporting another nucleic acid molecule to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids.

As used herein, the term "subject" refers to a mammal, e.g., preferably a human. Mammals include, but are not limited to, humans and domestic and farm animals, such as monkeys (e.g., a cynomolgus monkey), mice, dogs, cats, horses, and cows, etc.

As used herein, the term "gestational age" describes how far along the pregnancy is. The gestational age can be described in terms of weeks. Methods of determining gestational age are known in the art (e.g., *Committee on Obstetric Practice American Institute of Ultrasound in Medicine Society for Maternal-Fetal Medicine, Committee Opinion.* Number 700. May 2017; which is incorporated herein in its entirety). In some instances, the gestational age can be determined by ultrasound, weeks since first day of last menstrual period (LMP), or combinations thereof.

As used herein, the term "pharmaceutical composition" refers to a medicinal or pharmaceutical formulation that contains an active ingredient as well as one or more excipients and diluents to enable the active ingredient suitable for the method of administration. The pharmaceutical composition of the present invention includes pharmaceutically acceptable components that are compatible with the anti-FcRn antibody. The pharmaceutical composition may be in aqueous form for intravenous or subcutaneous administration or in tablet or capsule form for oral administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present invention, the pharmaceutically acceptable carrier must provide adequate pharmaceutical stability to the Fc construct. The nature of the carrier differs with the mode of administration. For example, for intravenous administration, an aqueous solution carrier is generally used; for oral administration, a solid carrier is preferred.

As used herein, the term "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

As used herein, the term "no more than" refers to an amount that is less than equal to. This may be an amount in integers. For example, no more than two substitutions can refer to 0, 1, or 2 substitutions.

As used herein, the terms "treatment" or "treating" refer to reducing, decreasing, decreasing the risk of, or decreasing the side effects of a particular disease or condition. Reducing, decreasing, decreasing the risk of, or decreasing the side effects of are relative to a subject who did not receive treatment, e.g, a control, a baseline, or a known control level or measurement.

DESCRIPTION OF THE DRAWINGS

FIG. 10 shows a graph that shows the amount of time it takes to achieve 100% FcRn occupancy by N027.

FIGS. 13C and 13D show images that show N027 increases intracellular IgG and co-localization of IgG with lysosomes (lysosomal markers: Lamp-1 and Dextran).

FIGS. 20A and 20B are graphs showing mean (SD) FcRn receptor occupancy in monocytes in the 30 and 15 mg/kg MAD cohorts by number of doses given.

FIGS. 21A and 21B are graphs showing mean (SD) serum IgG in the 30 and 15 mg/kg MAD cohorts by number of doses given.

FIG. 32 is a table showing impact on serum albumin in pregnant cynomolgus monkeys treated with N027 during gestation in the EFD and ePPND phases.

DETAILED DESCRIPTION OF THE INVENTION

Figure 1:
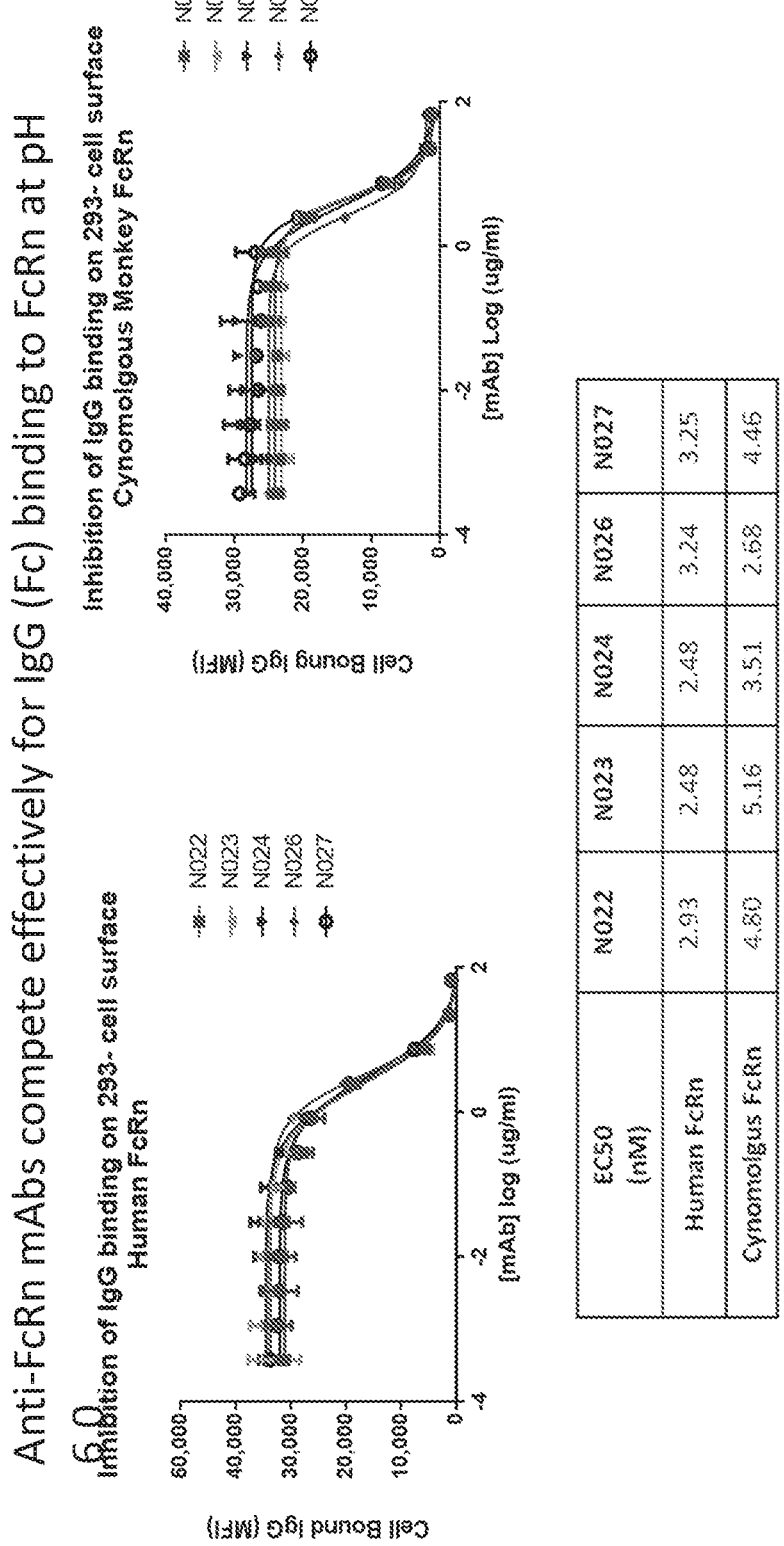
FIG. 1 includes two graphs and a table that show IgG competitive binding of antibodies N022-N024, N026, and N027 to human or cynomolgus monkey FcRn at pH 6.0.

The present invention features isolated antibodies that bind to human neonatal Fc receptor (FcRn) with high affinity. The present invention features anti-FcRn antibodies, methods and compositions for preparing anti-FcRn antibodies, and methods for blocking FcRn activity, reducing immune complex-based activation of an immune response, and treating immunological diseases. The present disclosure features anti-FcRn antibodies, methods and compositions for preparing anti-FcRn antibodies, and methods for blocking FcRn activity, reducing immune complex-based activation of an immune response, and treating immunological diseases. Furthermore, anti-FcRn antibodies can be used to decrease pathogenic antibody transport across the placenta of a pregnant subject, to increase pathogenic antibody catabolism in a pregnant subject, and to treat an antibody-mediated enhancement of viral disease in a fetus or a neonate.

I. Anti-FcRn Antibodies

In general, the invention features isolated antibodies that bind to the human FcRn with high affinity. An anti-FcRn antibody of the invention refers to an antibody that can bind to human FcRn and inhibit IgG (e.g., IgG autoantibodies) binding to FcRn. In some embodiments, the antibody is a monoclonal antibody. In other embodiments, the antibody is a polyclonal antibody. In some embodiments, the antibody is selected from the group consisting of a chimeric antibody, an affinity matured antibody, a humanized antibody, and a human antibody. In certain embodiments, the antibody is an antibody fragment, e.g., a Fab, Fab', Fab'-SH, F(ab')$_2$, or scFv.

In some embodiments, the antibody is a chimeric antibody. For example, an antibody contains antigen binding sequences from a non-human donor grafted to a heterologous non-human, human, or humanized sequence (e.g., framework and/or constant domain sequences). In one embodiment, the non-human donor is a mouse. In another embodiment, an antigen binding sequence is synthetic, e.g., obtained by mutagenesis (e.g., phage display screening, etc.). In a further embodiment, a chimeric antibody has non-human (e.g., mouse) variable regions and human constant regions. In one example, a mouse light chain variable region is fused to a human κ light chain. In another example, a mouse heavy chain variable region is fused to a human IgG1 constant region.

In one aspect, the invention features an isolated antibody capable of binding to human FcRn. The isolated antibody contains: (1) a light chain variable region that includes a CDR L1, a CDR L2, and a CDR L3 and (2) a heavy chain variable region that includes a CDR H1, a CDR H2, and a CDR H3, wherein the CDR L1 comprises a sequence having at least 92% identity to the sequence of TGTGSDVGSYNLVS (SEQ ID NO: 1), the CDR L2 comprises a sequence having at least 85% identity to the sequence of GDSERPS (SEQ ID NO: 2), the CDR L3 comprises a sequence having at least 90% identity to the sequence of SSYAGSGIYV (SEQ ID NO: 3), the CDR H1 comprises a sequence having at least 80% identity to the sequence of TYAMG (SEQ ID NO: 4), DYAMG (SEQ ID NO: 5), or NYAMG (SEQ ID NO: 6), the CDR H2 comprises a sequence having at least 92% identity to the sequence of SIGSSGAQTRYADS (SEQ ID NO: 7), SIGASGSQTRYADS (SEQ ID NO: 8), SIGASGAQTRYADS (SEQ ID NO: 9), or SIGASGGQTRYADS (SEQ ID NO: 10), and the CDR H3 comprises a sequence having at least 85% identity to the sequence of LAIGDSY (SEQ ID NO: 11). In some embodiments, the antibody binds human FcRn with a $K_D$ of less than 200, 150, 100, 50, or 40 pM. In some embodiments, the antibody binds human FcRn with a $K_D$ that is less than or equal to that of an antibody having the light chain variable region and heavy chain variable region of N022, N023, N024, N026, or N027, and further having the same Fc region as the antibody being compared.

In some embodiments, an isolated antibody of the invention comprises a CDR L1 that comprises the sequence of $X_1$GTGSDVGSYN$X_2$VS (SEQ ID NO: 12), a CDR 12 that comprises the sequence of GD$X_3X_4$RPS (SEQ ID NO: 13), a CDR L3 that comprises the sequence of $X_5$SY$X_6$GSGIYV (SEQ ID NO: 14), a CDR H1 that comprises the sequence of $Z_1$YAMG (SEQ ID NO: 15), a CDR H2 that comprises the sequence of SIG$Z_2$SG$Z_3$QT$Z_4$YADS (SEQ ID NO: 16), and a CDR H3 that comprises the sequence of LA$Z_5Z_6$DSY (SEQ ID NO: 17), where $X_1$ is a polar or hydrophobic amino acid (e.g., preferably T, A, S, or I), $X_2$ is a hydrophobic amino acid (e.g., preferably L or I), $X_3$ is a polar amino acid (e.g., preferably S, N, or T), $X_4$ is a polar or acidic amino acid (e.g., preferably Q, E, or N), $X_5$ is a polar or hydrophobic amino acid (e.g., preferably C, S, I, or Y), $X_6$ is a hydrophobic amino acid (e.g., preferably A or V), $Z_1$ is a polar or acidic amino acid (e.g., preferably E, T, D, or N), $Z_2$ is a polar or hydrophobic amino acid (e.g., preferably S or A), $Z_3$ is G, S, or A, $Z_4$ is a basic amino acid (e.g., preferably K or R), $Z_5$ is a hydrophobic or basic amino acid (e.g., preferably I, L, or H), and $Z_6$ is G, S, D, Q, or H, and where the antibody binds human FcRn with a $K_D$ of less than 200, 150, 100, 50, or 40 pM.

In other embodiments, an isolated antibody of the invention comprises a CDR L1 that comprises the sequence of TGTGSDVGSYNLVS (SEQ ID NO: 1), a CDR L2 that comprises the sequence of GDSERPS (SEQ ID NO: 2), a CDR L3 that comprises the sequence of SSYAGSGIYV (SEQ ID NO: 3), a CDR H1 that comprises the sequence of $Z_1$YAMG (SEQ ID NO: 15), a CDR H2 that comprises the sequence of SIG$Z_2$SG$Z_3$QTRYADS (SEQ ID NO: 18), and a CDR H3 that comprises the sequence of LAIGDSY (SEQ ID NO: 11), where $Z_1$ is T, D, or N, $Z_2$ is S or A, and $Z_3$ is G, S or A.

Table 1 shows the amino acid sequences of the light and heavy chain complementary determining regions (CDRs) of some exemplary anti-FcRn antibodies of the invention.

(SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS.

In some embodiments, the heavy chain of an isolated antibody of the invention comprises a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

TABLE 1

| Anti-FcRn antibody | CDR L1 | CDR L2 | CDR L3 | CDR H1 | CDR H2 | CDR H3 |
|---|---|---|---|---|---|---|
| N022 | TGTGSDVGSYNLVS (SEQ ID NO: 1) | GDSERPS (SEQ ID NO: 2) | SSYAGSGIYV (SEQ ID NO: 3) | TYAMG (SEQ ID NO: 4) | SIGSSGAQTRYADS (SEQ ID NO: 7) | LAIGDSY (SEQ ID NO: 11) |
| N023 | TGTGSDVGSYNLVS (SEQ ID NO: 1) | GDSERPS (SEQ ID NO: 2) | SSYAGSGIYV (SEQ ID NO: 3) | DYAMG (SEQ ID NO: 5) | SIGASGSQTRYADS (SEQ ID NO: 8) | LAIGDSY (SEQ ID NO: 11) |
| N024 | TGTGSDVGSYNLVS (SEQ ID NO: 1) | GDSERPS (SEQ ID NO: 2) | SSYAGSGIYV (SEQ ID NO: 3) | NYAMG (SEQ ID NO: 6) | SIGASGAQTRYADS (SEQ ID NO: 9) | LAIGDSY (SEQ ID NO: 11) |
| N026 | TGTGSDVGSYNLVS (SEQ ID NO: 1) | GDSERPS (SEQ ID NO: 2) | SSYAGSGIYV (SEQ ID NO: 3) | TYAMG (SEQ ID NO: 4) | SIGASGGQTRYADS (SEQ ID NO: 10) | LAIGDSY (SEQ ID NO: 11) |
| N027 | TGTGSDVGSYNLVS (SEQ ID NO: 1) | GDSERPS (SEQ ID NO: 2) | SSYAGSGIYV (SEQ ID NO: 3) | TYAMG (SEQ ID NO: 4) | SIGASGSQTRYADS (SEQ ID NO: 8) | LAIGDSY (SEQ ID NO: 11) |

Table 2 shows the SEQ ID NOs of the light and heavy chains of these exemplary anti-FcRn antibodies of the invention.

TABLE 2

| Anti-FcRn antibody | Light Chain | Heavy Chain |
|---|---|---|
| N022 | SEQ ID NO: 19 | SEQ ID NO: 20 |
| N023 | | SEQ ID NO: 21 |
| N024 | | SEQ ID NO: 22 |
| N026 | | SEQ ID NO: 23 |
| N027 | | SEQ ID NO: 24 |

In some embodiments, the light chain of an isolated antibody of the invention comprises a sequence having at least 90% identity to the sequence of -continued
PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments, the heavy chain of an isolated antibody of the invention comprises a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

-continued

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

In some embodiments, the heavy chain of an isolated antibody of the invention comprises a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In other embodiments, the heavy chain of an isolated antibody of the invention comprises a sequence having at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In yet other embodiments, the heavy chain of an isolated antibody of the invention comprises a sequence having at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain and a heavy chain, where the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises a sequence having at least 90% identity to the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain and a heavy chain, where the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises a sequence having at least 90% identity to the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain and a heavy chain, where the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises a sequence having at least 90% identity to the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain and a heavy chain, where the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises a sequence having at least 90% identity to the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody including a light chain and a heavy chain, where the light chain comprises a sequence having at least 90% identity to the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises a sequence having at least 90% identity to the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

Furthermore, in any of the anti-FcRn antibodies described herein, the heavy chain of the antibody comprises a sequence having at least 95%, 97%, 99%, or 100% identity to the sequence of any one of SEQ ID NOs: 20-24. In any of the anti-FcRn antibodies described herein, the light chain comprises a sequence having at least 95%, 97%, 99%, or 100% identity to the sequence of SEQ ID NO: 19.

The antibodies of the invention may further contain amino acid substitutions, additions, and/or deletions outside of the CDRs (i.e., in framework regions (FRs)). In some embodiments, the antibodies of the invention may further include any one or more of the following amino acid substitutions: A23V, S30R, L80V, A84T, E85D, A93V, relative to the sequence of any one of SEQ ID NOs: 20-24, and Q38H, V58I, and G99D, relative to the sequence of SEQ ID NO: 19.

The antibodies may further contain amino acid substitutions, additions, and/or deletions outside of the CDRs (i.e., in framework regions (FRs)). An amino acid substitution, addition, and/or deletion can be a substitution, addition, and/or deletion of one or more amino acids (e.g., 1, 2, 3, 4, 5, 6, 7, 8, or more). An amino acid substitution, addition, and/or deletion can be a substitution, addition, and/or deletion of eight or fewer, seven or fewer, six or fewer, five or fewer, four or fewer, three or fewer, or two or fewer single amino acids. In some embodiments, the antibodies may further include any one or more of the following amino acid substitutions: A23V, S30R, L80V, A84T, E85D, A93V, relative to the sequence of any one of SEQ ID NOs: 20-24, and Q38H, V58I, and G99D, relative to the sequence of SEQ ID NO: 19.

In some embodiments, the antibodies of the invention may include amino acid substitutions, additions, and/or deletions in the constant regions (e.g., Fc region) of the antibody that, e.g., lead to decreased effector function, e.g., decreased complement-dependent cytolysis (CDC), antibody-dependent cell-mediated cytolysis (ADCC), and/or antibody-dependent cell-mediated phagocytosis (ADCP), and/or decreased B-cell killing. The constant regions are not involved directly in binding an antibody to its target, but exhibit various effector functions, such as participation of the antibody in antibody-dependent cellular toxicity. In some embodiments, the antibodies of the invention are characterized by decreased binding (i.e., absence of binding) to human complement factor C1q and/or human Fc receptor on natural killer (NK) cells. In other embodiments, the antibodies of the invention are characterized by decreased binding (i.e., absence of binding) to human FcγRI, FcγRIIA, and/or FcγRIIIA. To alter or reduce an antibody-dependent effector function, such as CDC, ADCC, ADCP, and/or B-cell killing, antibodies of the invention may be of the IgG class and contain one or more amino acid substitutions E233, L234, G236, D265, D270, N297, E318, K320, K322, A327, A330, P331, and/or P329 (numbering according to the EU index of Kabat (Sequences of Proteins of Immunological Interest, 5th Ed. Public Health Service, National Institutes of Health, Bethesda, Md. (1991))). In some embodiments, the antibodies contain the mutations L234A/L235A or D265A/N297A. Preferably, an anti-FcRn antibody of the invention contains amino acidhdfn substitution N297A, relative to the sequence of any one of SEQ ID NOs: 20-24, such that the antibody of the invention is changed to an aglycosylated form. The resulting effectorless antibody shows very little binding to complement or Fc receptors (i.e., complement C1q binding), indicating low CDC potential.

In other embodiments, the antibodies of the invention may include those having specific amino acid changes that improve stability of the antibody.

Moreover, in other embodiments, to minimize potential immunogenicity, some antibodies of the invention, e.g., N024, N026, and N027, may undergo an allotype change from G1m17.1 to G1m17 by substituting amino acids D355 and L357 (relative to the sequence of any one of SEQ ID NOs: 20-24) to glutamic acid and methionine, respectively.

In other embodiments, the antibodies of the invention, e.g., N022-N024, N026, and N027, do not contain a C-terminal lysine at residue 446, relative to the sequence of any one of SEQ ID NOs: 20-24.

The invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 20)
EVQLLESGGGLVQPGGSLRLSCAASGFTFSTYAMGWVRQAPGKGLEWVSS

IGSSGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 21)
EVQLLESGGGLVQPGGSLRLSCAASGFTFSDYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 22)
EVQLLESGGGLVQPGGSLRLSCAASGFTFSNYAMGWVRQAPGKGLEWVSS

IGASGAQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 23)
EVQLLESGGGLVQPGGSLRLSCAASGFTFSTYAMGWVRQAPGKGLEWVSS

IGASGGQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

The invention features an isolated antibody containing a light chain and a heavy chain, wherein the light chain comprises the sequence of (SEQ ID NO: 19)
QSALTQPASVSGSPGQSITISCTGTGSDVGSYNLVSWYQQHPGKAPKLMI

YGDSERPSGVSNRFSGSKSGNTASLTISGLQAEDEADYYCSSYAGSGIYV

FGTGTKVTVLGQPKAAPSVTLFPPSSEELQANKATLVCLISDFYPGAVTV

AWKADSSPVKAGVETTTPSKQSNNKYAASSYLSLTPEQWKSHKSYSCQVT

HEGSTVEKTVAPTECS;
and the heavy chain comprises the sequence of (SEQ ID NO: 24)
EVQLLESGGGLVQPGGSLRLSCAASGFTFSTYAMGWVRQAPGKGLEWVSS

IGASGSQTRYADSVKGRFTISRDNSKNTLYLQMNSLRAEDTAVYYCARLA

IGDSYWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICN

VNHKPSNTKVDKKVEPKSCDKTHTCPPCPAPELLGGPSVFLFPPKPKDTL

MISRTPEVTCVVVDVSHEDPEVKFNWYVDGVEVHNAKTKPREEQYASTYR

VVSVLTVLHQDWLNGKEYKCKVSNKALPAPIEKTISKAKGQPREPQVYTL

PPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPG.

In any of the anti-FcRn antibodies described herein, in some embodiments, the antibody binds mouse or rat FcRn with a $K_D$ of less than 200, 150, 100, 50, or 40 pM.

In any of the anti-FcRn antibodies described herein, in some embodiments, the antibody binds to human FcRn with an affinity of between 1-100, 5-150, 5-100, 5-75, 5-50, 10-50, or 10-40 pM.

The anti-FcRn antibodies of the invention may be of immunoglobulin antibody isotype IgG, IgE, IgM, IgA, or IgD. Preferably, the anti-FcRn antibodies are of immunoglobulin antibody isotype IgG. The anti-FcRn antibodies may also be of any immunoglobulin antibody isotype subclasses. For example, the anti-FcRn antibodies may be of IgG subclass IgG1, IgG2, IgG3, or IgG4. Preferably, the anti-FcRn antibodies are of subclass IgG1. In particular, the anti-FcRn antibodies of the invention contain an IgG G1 m17 or G1m17.1 allotype heavy chain. In some embodiments, the light chain of the anti-FcRn antibodies may be a κ light chain, a λ light chain, or a κ-λ chimeric light chain. In preferred embodiments, the anti-FcRn antibodies of the invention contain a full-length λ light chain.

In some embodiments, the antibodies of the invention are monoclonal. The antibodies of the invention may also be polyclonal, chimeric, humanized or fully human. In some embodiments, the antibody of the invention may be affinity matured. In other embodiments, the antibody of the invention may be an antibody fragment.

Without being bound by theory, it is believed that the anti-FcRn antibodies of the invention compete with and inhibit the binding of IgG to human FcRn. Epitope mapping by hydrogen-deuterium exchange of the antibodies of the invention indicates that the antibodies bind to an epitope on FcRn located in and/or adjacent to the Fc-FcRn interaction interface, which suggests that the antibodies of the invention block IgG binding to FcRn by direction inhibition. Furthermore, the epitope-mapped binding site is distant from the albumin-binding site of FcRn. Accordingly, serum albumin-binding should not be inhibited and serum albumin levels should not be decreased. Indeed, experimental evidence shows mouse albumin levels remained constant after anti-FcRn antibody administration, indicating that albumin recycling is not disturbed by antibody binding to FcRn.

II. FcRn Inhibition

FcRn is a type I transmembrane protein that functions as an IgG- and serum albumin-binding, intracellular vesicular trafficking protein. FcRn is expressed in endothelial cells, luminal epithelial cells, hepatocytes, podocytes, granulocytes, monocytes, macrophages, dendritic cells, and NK cells, but not on B or T cells. FcRn maintains the half-life of IgG by binding and trafficking constitutively internalized IgG back to the cell surface. Binding of both Fc and serum albumin by FcRn occurs in the early endosome at pH 6.0, followed by sorting of the FcRn into vesicles, which traffic the FcRn-bound IgG or albumin back to the cell surface where FcRn rapidly releases the IgG or albumin at pH 7.4. This trafficking cycle maintains the half-life of IgG and albumin by recycling both into the circulation and preventing trafficking to the lysosomes for degradation. FcRn also captures internalized IgG Fc in epithelial cells and transports them bidirectionally to the opposing apical or basolateral membranes. This function allows IgG to traffic to the lumen of organs such as the gastrointestinal tract or the transport of IgG or IgG-antigen complexes from the lumen to the vasculature or lymphoid tissues in the stromal layers.

In order to study the contribution of FcRn to IgG homeostasis, mice have been engineered so that parts of the light and heavy chains of FcRn have been "knocked out" so that these proteins are not expressed (Junghans et al., *Proc Natl Acad Sci USA* 93:5512, 1996). In these mice, the serum half-life and concentrations of IgG were dramatically reduced, suggesting an FcRn-dependent mechanism of IgG homeostasis. Studies in rodent models, such as the one discussed above, suggest that blockage of FcRn can increase IgG catabolism, including that of pathogenic autoantibodies, thereby inhibiting disease (e.g., an autoimmune disease) development. FcRn may also contribute to antigen presentation through trafficking of immune complexes to antigen degradation and MHC loading compartments.

The present invention provides isolated anti-FcRn antibodies that bind to human FcRn with high affinity. The anti-FcRn antibodies of the invention compete with and effectively inhibit the binding of other anti-FcRn antibodies (e.g., IgG, IgG autoantibodies) to FcRn, thereby increasing the catabolism and decreasing the half-life of other anti-FcRn antibodies (e.g., IgG, IgG autoantibodies). The anti-FcRn antibodies of the invention may be used in a method of treating or reducing immune complex-based activation of an immune response in a subject, such as an immune response caused by autoantibodies in an autoimmune disease.

Placental transfer of maternal IgG antibodies to the fetus is an important FcRn-dependent mechanism that provides protection to the neonate while his/her humoral response is inefficient. During fetal life, FcRn in the syncytiotrophoblast layers of the placenta is responsible for the transfer of maternal IgG antibodies to the fetus. Pathogenic maternal antibodies (e.g., pathogenic maternal IgG antibodies) may also cross the placenta by binding to FcRn and cause alloimmune disorders and/or autoimmune disorders in the fetus and neonate. In some embodiments, pathogenic antibodies in the pregnant subject cause a fetal and neonatal alloimmune and/or autoimmune disorder in a fetus in the pregnant subject. The anti-FcRn antibodies described herein (e.g., N022-N024, N026, and N027, preferably N027 and/or N024) may compete with and inhibit the binding of maternal pathogenic antibodies (e.g., maternal pathogenic IgG antibodies) to FcRn, thereby increasing the catabolism and decreasing the half-life of these pathogenic antibodies.

The present disclosure provides isolated anti-FcRn antibodies that bind to human FcRn. The anti-FcRn antibodies may compete with and inhibit the binding of other anti-FcRn antibodies (e.g., IgG, IgG autoantibodies) to FcRn, thereby increasing the catabolism and decreasing the half-life of other anti-FcRn antibodies (e.g., IgG, IgG autoantibodies). The anti-FcRn antibodies may be used in a method of treating or reducing immune complex-based activation of an immune response in a subject, such as an immune response caused by autoantibodies in an autoimmune disease. Reducing an immune response may be described as reducing an immune response relative to a subject who does not receive treatment (e.g., a control subject). The anti-FcRn antibodies may also be used in methods of decreasing pathogenic antibody transport (e.g., pathogenic maternal IgG antibody transport) across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to human FcRn. Decreasing pathogenic antibody transport across the placenta of a pregnant subject, may be described as decreasing pathogenic antibody transport relative to a subject who does not receive treatment (e.g., a control subject).

IV. Vectors, Host Cells, and Antibody Production

The anti-FcRn antibodies of the invention can be produced from a host cell. A host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (e.g., transformation, transfection, electroporation, calcium phosphate precipitation, direct microinjection, infection, etc). The choice of nucleic acid vectors depends in part on the host cells to be used. Generally, preferred host cells are of either prokaryotic (e.g., bacterial) or eukaryotic (e.g., mammalian) origin.

Nucleic Acid Vector Construction and Host Cells

A nucleic acid sequence encoding the amino acid sequence of an anti-FcRn antibody of the invention may be prepared by a variety of methods known in the art. These methods include, but are not limited to, oligonucleotide-mediated (or site-directed) mutagenesis and PCR mutagenesis. A nucleic acid molecule encoding an anti-FcRn antibody of the invention may be obtained using standard techniques, e.g., gene synthesis. Alternatively, a nucleic acid molecule encoding a wild-type anti-FcRn antibody may be mutated to contain specific amino acid substitutions using standard techniques in the art, e.g., QuikChange™ mutagenesis. Nucleic acid molecules can be synthesized using a nucleotide synthesizer or PCR techniques.

Nucleic acid sequences encoding anti-FcRn antibodies of the invention may be inserted into a vector capable of replicating and expressing the nucleic acid molecules in prokaryotic or eukaryotic host cells. Many vectors are available in the art and can be used for the purpose of the invention. Each vector may contain various components that may be adjusted and optimized for compatibility with the particular host cell. For example, the vector components may include, but are not limited to, an origin of replication, a selection marker gene, a promoter, a ribosome binding site, a signal sequence, the nucleic acid sequence encoding protein of interest, and a transcription termination sequence.

In some embodiments, mammalian cells are used as host cells for the invention. Examples of mammalian cell types include, but are not limited to, human embryonic kidney (HEK) (e.g., HEK293, HEK 293F), Chinese hamster ovary (CHO), HeLa, COS, PC3, Vero, MC3T3, NS0, Sp2/0, VERY, BHK, MDCK, W138, BT483, Hs578T, HTB2, BT20, T47D, NS0 (a murine myeloma cell line that does not endogenously produce any immunoglobulin chains), CRL7O3O, and HsS78Bst cells. In other embodiments, E. coli cells are used as host cells for the invention. Examples of E. coli strains include, but are not limited to, E. coli 294 (ATCC® 31,446), E. coli A 1776 (ATCC® 31,537, E. coli BL21 (DE3) (ATCC® BAA-1025), and E. coli RV308 (ATCC® 31,608). Different host cells have characteristic and specific mechanisms for the posttranslational processing and modification of protein products. Appropriate cell lines or host systems may be chosen to ensure the correct modification and processing of the anti-FcRn antibody expressed. The above-described expression vectors may be introduced into appropriate host cells using conventional techniques in the art, e.g., transformation, transfection, electroporation, calcium phosphate precipitation, and direct microinjection. Once the vectors are introduced into host cells for protein production, host cells are cultured in conventional nutrient media modified as appropriate for inducing promoters, selecting transformants, or amplifying the genes encoding the desired sequences. Methods for expression of therapeutic proteins are known in the art, see, for example, Paulina Balbas, Argelia Lorence (eds.) *Recombinant Gene Expression: Reviews and Protocols (Methods in Molecular Biology)*, Humana Press; 2nd ed. 2004 (Jul. 20, 2004) and Vladimir Voynov and Justin A. Caravella (eds.) *Therapeutic Proteins: Methods and Protocols (Methods in Molecular Biology)* Humana Press; 2nd ed. 2012 (Jun. 28, 2012).

Protein Production, Recovery, and Purification

Host cells used to produce the anti-FcRn antibodies of the invention may be grown in media known in the art and suitable for culturing of the selected host cells. Examples of suitable media for mammalian host cells include Minimal Essential Medium (MEM), Dulbecco's Modified Eagle's Medium (DMEM), Expi293™ Expression Medium, DMEM with supplemented fetal bovine serum (FBS), and RPMI-1640. Examples of suitable media for bacterial host cells include Luria broth (LB) plus necessary supplements, such as a selection agent, e.g., ampicillin. Host cells are cultured at suitable temperatures, such as from about 20° C. to about 39° C., e.g., from 25° C. to about 37° C., preferably 37° C., and $CO_2$ levels, such as 5 to 10% (preferably 8%). The pH of the medium is generally from about 6.8 to 7.4, e.g., 7.0, depending mainly on the host organism. If an inducible promoter is used in the expression vector of the invention, protein expression is induced under conditions suitable for the activation of the promoter.

Protein recovery typically involves disrupting the host cell, generally by such means as osmotic shock, sonication, or lysis. Once the cells are disrupted, cell debris may be removed by centrifugation or filtration. The proteins may be further purified. An anti-FcRn antibody of the invention may be purified by any method known in the art of protein purification, for example, by protein A affinity, other chromatography (e.g., ion exchange, affinity, and size-exclusion column chromatography), centrifugation, differential solubility, or by any other standard technique for the purification of proteins. (see Process Scale Purification of Antibodies, Uwe Gottschalk (ed.) John Wiley & Sons, Inc., 2009). In some instances, an anti-FcRn antibody can be conjugated to marker sequences, such as a peptide to facilitate purification. An example of a marker amino acid sequence is a hexa-histidine peptide (His-tag), which binds to nickel-functionalized agarose affinity column with micromolar affinity. Other peptide tags useful for purification include, but are not limited to, the hemagglutinin "HA" tag, which corresponds to an epitope derived from the influenza hemagglutinin protein.

Alternatively, anti-FcRn antibodies of the invention can be produced by the cells of a subject (e.g., a human), e.g., in the context of therapy, by administrating a vector (e.g., a retroviral vector, adenoviral vector, poxviral vector (e.g., vaccinia viral vector, such as Modified Vaccinia Ankara (MVA)), adeno-associated viral vector, and alphaviral vector) containing a nucleic acid molecule encoding the anti-FcRn antibody of the invention. The vector, once inside a cell of the subject (e.g., by transformation, transfection, electroporation, calcium phosphate precipitation, direct microinjection, infection, etc) will promote expression of the anti-FcRn antibody, which is then secreted from the cell. If treatment of a disease or disorder is the desired outcome, no further action may be required. If collection of the protein is desired, blood may be collected from the subject and the protein purified from the blood by methods known in the art.

V. Pharmaceutical Compositions and Preparations

The invention features pharmaceutical compositions that include one or more anti-FcRn antibodies described herein. In some embodiments, pharmaceutical compositions of the invention contain one or more antibodies of the invention, e.g., N022-N024, N026, and N027, as the therapeutic proteins. In other embodiments, pharmaceutical compositions of the invention containing one or more antibodies of the invention, e.g., N022-N024, N026, and N027, may be used in combination with other agents (e.g., therapeutic biologics and/or small molecules) or compositions in a therapy. In addition to a therapeutically effective amount of the antibody, the pharmaceutical compositions may contain one or more pharmaceutically acceptable carriers or excipients, which can be formulated by methods known to those skilled in the art.

Acceptable carriers and excipients in the pharmaceutical compositions are nontoxic to recipients at the dosages and concentrations employed. Acceptable carriers and excipients may include buffers, antioxidants, preservatives, polymers, amino acids, and carbohydrates. Pharmaceutical compositions of the invention can be administered parenterally in the form of an injectable formulation. Pharmaceutical compositions for injection (i.e., intravenous injection) can be formulated using a sterile solution or any pharmaceutically acceptable liquid as a vehicle. Pharmaceutically acceptable vehicles include, but are not limited to, sterile water, physiological saline, and cell culture media (e.g., Dulbecco's Modified Eagle Medium (DMEM), α-Modified Eagles Medium (α-MEM), F-12 medium). Formulation methods are known in the art, see e.g., Banga (ed.) *Therapeutic Peptides and Proteins: Formulation, Processing and Delivery Systems* (2nd ed.) Taylor & Francis Group, CRC Press (2006).

The pharmaceutical composition may be formed in a unit dose form as needed. The amount of active component, e.g., one or more anti-FcRn antibodies of the invention (e.g., N022-N024, N026, and N027, preferably N027 and/or N024), included in the pharmaceutical preparations is such that a suitable dose within the designated range is provided (e.g., a dose within the range of 0.01-500 mg/kg of body weight).

VI. Routes, Dosage, and Administration

Pharmaceutical compositions of the invention that contain one or more anti-FcRn antibodies (e.g., N022-N024, N026, and N027, preferably N027 and/or N024) as the therapeutic proteins may be formulated for intravenous administration, parenteral administration, subcutaneous administration, intramuscular administration, intra-arterial administration, intrathecal administration, or intraperitoneal administration. In particular, intravenous administration is preferred. The pharmaceutical composition may also be formulated for, or administered via, oral, nasal, spray, aerosol, rectal, or vaginal administration. For injectable formulations, various effective pharmaceutical carriers are known in the art.

The dosage of the pharmaceutical compositions of the invention depends on factors including the route of administration, the disease to be treated, and physical characteristics, e.g., age, weight, general health, of the subject. Typically, the amount of an anti-FcRn antibody of the invention (e.g., any one of N022-N024, N026, and N027, preferably N027 or N024) contained within a single dose may be an amount that effectively prevents, delays, or treats the disease without inducing significant toxicity. A pharmaceutical composition of the invention may include a dosage of an anti-FcRn antibody of the invention ranging from 0.01 to 500 mg/kg (e.g., 0.01, 0.1, 0.2, 0.3, 0.4, 0.5, 1, 2, 3, 4, 5, 10, 15, 20, 25, 30, 35, 40, 45, 50, 100, 150, 200, 250, 300, 350, 400, 450, or 500 mg/kg) and, in a more specific embodiment, about 1 to about 100 mg/kg and, in a more specific embodiment, about 1 to about 50 mg/kg. The dosage may be adapted by the physician in accordance with conventional factors such as the extent of the disease and different parameters of the subject. Additionally, the dosage may be adapted by the physician in accordance with factors such as gestational age, preparation for birth, weight gain of woman, and/or length of pregnancy.

In some cases, the compositions and pharmaceutical compositions described herein are administered to a pregnant woman throughout pregnancy. In some cases, the compositions and pharmaceutical compositions described herein are administered to a pregnant woman for around 5-25 weeks during pregnancy (e.g., around 5, 6, 7, 8, 9, 10, 11, 12, 13, 14, 15, 16, 17, 18, 19, 20, 21, 22, 23, 24, or 25 weeks). In some instances, administration of the compositions and pharmaceutical compositions ceases after around gestational age 34 (week 34) (E.g., after week 34, 35, 36, or 37). In some instances, IVIG is administered to the pregnant woman after cessation of administration of the compositions and pharmaceutical compositions. In some instances, IVIG is administered between around 3-15 days (e.g., 3, 4, 5, 6, 7, 8, 9, 10, 11, 12, 13, 14, or 15 days) after cessation of administration of the compositions and pharmaceutical compositions. In some cases, the time of IVIG administration after cessation of administration of the compositions and pharmaceutical compositions is adapted in accordance with factors such as weight gain of woman. In some instances, the compositions and pharmaceutical compositions described herein are first administered after gestational age 12 (e.g. after 12, 13, 14, 15, 16, 17, 18, 19, 20, 21, 22, 23, 24, 25, 26, 27, 28, 29, or 30). In some cases they are administered during the pregnancy between gestational age 14 and 26 (e.g., 14 and 25; 15 and 25; or 15 and 26, etc.). In some cases they are administered during the pregnancy between gestational age 12 and 36 (e.g., 12 and 36; 12 and 35; 12 and 34; 13 and 36; 13 and 35; 13 and 34; 14 and 36; 14 and 35; 14 and 34; 15 and 36; 15 and 35; 15 and 34; 16 and 36; 16 and 35; or 16 and 34; etc.).

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, and oral dosage forms (e.g., ingestible solutions, drug release capsules). Generally, therapeutic proteins are dosed at 1-100 mg/kg, e.g., 1-50 mg/kg. Pharmaceutical compositions of the invention that contain an anti-FcRn antibody (e.g., any one of N022-N024, N026, and N027, preferably N027 or N024) may be administered to a subject in need thereof, for example, one or more times (e.g., 1-10 times or more) daily, weekly, monthly, biannually, annually, or as medically necessary. Dosages may be provided in either a single or multiple dosage regimens. The timing between administrations may decrease as the medical condition improves or increase as the health of the patient declines.

VII. Methods of Treatment and Indications

The blockade of human FcRn by anti-FcRn antibodies of the invention may be of therapeutic benefit in diseases that are driven by IgG autoantibodies. The ability of FcRn blockade to induce overall IgG catabolism and removal of multiple species of autoantibodies without perturbing serum albumin, small circulating metabolites, or lipoproteins offers a method to expand the utility and accessibility of an autoantibody removal strategy to patients with autoantibody-driven autoimmune disease pathology. While the invention is not bound by theory, the dominant mechanism of action of an anti-FcRn antibody of the invention may be to increase the catabolism of pathogenic autoantibodies in circulation and decrease autoantibody and immune complex deposition in affected tissues.

The pharmaceutical compositions and methods of the invention containing one or more anti-FcRn antibodies (e.g., N022-N024, N026, and N027, preferably N027 and/or N024) are useful to promote catabolism and clearance of pathogenic antibodies, e.g., IgG and IgG autoantibodies in a subject, to reduce the immune response, e.g., to block immune complex-based activation of the immune response in a subject, and to treat immunological conditions or diseases in a subject. In particular, the pharmaceutical compositions and methods of the invention are useful to reduce or treat an immune complex-based activation of an acute or chronic immune response. The acute immune response may be activated by a medical condition selected from the group consisting of pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura (ITP), autoimmune haemolytic anaemia (AIHA), immune neutropenia, dialated cardiomyopathy, and serum sickness. The chronic immune response may be activated by a medical condition selected from the group consisting of chronic inflammatory demyelinating polyneuropathy (CIDP), systemic lupus, a chronic form of a disorder indicated for acute treatment, reactive arthropathies, primary biliary cirrhosis, ulcerative colitis, and antineutrophil cytoplasmic antibody (ANCA)-associated vasculitis.

In some embodiments, the pharmaceutical compositions and methods of the invention are useful to reduce or treat an immune response activated by an autoimmune disease. The autoimmune disease may be selected from the group consisting of alopecia areata, ankylosing spondylitis, antiphospholipid syndrome, Addison's disease, hemolytic anemia, autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis.

In particular, the pharmaceutical compositions and methods of the invention are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica.

In some embodiments, the pharmaceutical compositions and methods are useful to decrease the risk of or decrease the risk of developing anemia in the fetus. In some embodiments, the pharmaceutical compositions and methods are useful to decrease or obviate the need for IUT (intrauterine transfusion). In some embodiments, the pharmaceutical compositions and methods are useful to decrease or obviate the need for antenatal PP+IVIg, postnatal transfusion, IVIg, and/or phototherapy.

In some embodiments, the pharmaceutical compositions and methods are useful to reduce or treat an immune response activated by an autoimmune disease. The autoimmune disease may be selected from the group consisting of alopecia areata, ankylosing spondylitis, antiphospholipid syndrome (e.g., antiphospholipid antibody syndrome), Addison's disease, hemolytic anemia (e.g., warm autoimmune hemolytic anemia), autoimmune hepatitis, hepatitis, Behcets disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, epidermolysis bullosa; fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, membranous nephropathy, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, and Wegener's granulomatosis. In some embodiments, the pharmaceutical compositions and methods are useful to reduce or treat an immune response in a fetus or neonate. In some embodiments, the pharmaceutical compositions and methods are useful to reduce or treat an immune response in a fetus or neonate activated by an autoimmune disease in the pregnant mother.

In particular, the pharmaceutical compositions and methods are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica. In some embodiments, the pharmaceutical compositions and methods are useful to reduce or treat an immune response in a fetus or neonate. In some embodiments, the pharmaceutical compositions and methods are useful to reduce or treat an immune response activated by systemic lupus erythematosus, antiphospholipid syndrome, pemphigus vulgaris/bullous pemphigoid, antineutrophil cytoplasmic antibody (ANCA)-associated vasculitis, myasthenia gravis, or neuromyelitis optica in the pregnant mother.

The pharmaceutical compositions and methods are useful in methods of decreasing pathogenic antibody transport (e.g., pathogenic maternal IgG antibody transport) across the placenta of a pregnant subject, increasing pathogenic antibody catabolism in a pregnant subject, and treating an antibody-mediated enhancement of viral disease in a fetus or a neonate by administering to a pregnant subject an isolated antibody that binds to human FcRn. Diseases and disorders that may benefit from FcRn inhibition by the isolated anti-FcRn antibodies described herein (e.g., N022-N024, N026, and N027, preferably N027 and/or N024) include diseases and disorders in a fetus and/or neonate that are caused by the transfer of maternal pathogenic antibodies (e.g., maternal pathogenic IgG antibodies) across the placenta from a pregnant subject to the fetus and/or neonate.

In some embodiments, the diseases and disorders that may benefit from FcRn inhibition by the isolated anti-FcRn antibodies described herein (e.g., N022-N024, N026, and N027, preferably N027 and/or N024) are fetal and neonatal alloimmune and/or autoimmune disorders. Fetal and neonatal alloimmune disorders are disorders in a fetus and/or neonate that is caused by pathogenic antibodies in the pregnant subject. The pathogenic antibodies in the pregnant subject may attack the antigens of the fetus (e.g., antigens the fetus inherited from the fetus' father), causing the fetus or the neonate to have a fetal and neonatal alloimmune and/or autoimmune disorder.

Examples of fetal and neonatal alloimmune and/or autoimmune disorders that may be treated by the methods described herein include, but are not limited to, fetal and neonatal alloimmune thrombocytopenia (FNAIT), hemolytic disease of the fetus and newborn (HDFN), alloimmune pan-thrombocytopenia, congenital heart block, fetal arthrogryposis, neonatal myasthenia gravis, neonatal autoimmune hemolytic anemia, neonatal anti-phospholipid syndrome, neonatal polymyositis, dermatomyositis, neonatal lupus, neonatal scleroderma. Behcet's disease, neonatal Graves' disease, neonatal Kawasaki disease, neonatal autoimmune thyroid disease, and neonatal type I diabetes mellitus.

In some embodiments, the diseases and disorders that may benefit from FcRn inhibition by the isolated anti-FcRn antibodies described herein (e.g., N022-N024, N026, and N027, preferably N027 and/or N024) are viral diseases wherein antibodies facilitate viral entry into host cells, leading to increased or enhanced infectivity in the cells, e.g., antibody-mediated enhancement of viral disease. In some embodiments, an antibody may bind to a viral surface protein and the antibody/virus complex may bind to an FcRn on a cell surface through interaction between the antibody and the receptor. Subsequently, the antibody/virus complex may get internalized into the cell. For example, a virus may gain entry into the cells and/or tissues of a fetus through forming a complex with a maternal IgG antibody. A maternal IgG antibody may bind to a viral surface protein and the IgG/virus complex may bind to an FcRn in the syncytiotrophoblasts of the placenta, which then transfers the complex into the fetus.

In some embodiments, the methods described herein may be used to treat an antibody-mediated enhancement of viral disease. In some embodiments, the viral diseases that are enhanced by pathogenic antibodies (e.g., pathogenic IgG antibodies) include, but are not limited to, viral diseases caused by an alpha virus infection, flavivirus infection, Zika virus infection, Chikungunya virus infection, Ross River virus infection, severe acute respiratory syndrome coronavirus infection, Middle East respiratory syndrome, avian influenza infection, influenza virus infection, human respiratory syncytial virus infection, Ebola virus infection, yellow fever virus infection, dengue virus infection, human immunodeficiency virus infection, respiratory syncytial virus infection, Hantavirus infection, Getah virus infection, Sindbis virus infection, Bunyamwera virus infection, West Nile virus infection, Japanese encephalitis virus B infection, rabbitpox virus infection, lactate dehydrogenase elevating virus infection, reovirus infection, rabies virus infection, foot-and-mouth disease virus infection, porcine reproductive and respiratory syndrome virus infection, simian hemorrhagic fever virus infection, equine infectious anemia virus infection, caprine arthritis virus infection, African swine fever virus infection, lentivirus infection, BK papovavirus infection, Murray Valley encephalitis virus infection, enterovirus infection, cytomegalovirus infection, pneumovirus infection, morbillivirus infection, and measles virus infection.

The blockade of human FcRn by anti-FcRn antibodies may be of therapeutic benefit in diseases that are driven by pathogenic antibodies (e.g., pathogenic IgG antibodies). The ability of FcRn blockade to induce overall pathogenic antibody catabolism and removal of multiple species of pathogenic antibodies, small circulating metabolites, or lipoproteins offers a method to expand the utility and accessibility of a pathogenic antibody removal strategy to patients with pathogenic antibody-driven autoimmune disease pathology. While not bound by theory, the dominant mechanism of action of an anti-FcRn antibody may be to increase the catabolism of pathogenic antibodies in circulation and decrease pathogenic antibody and immune complex deposition in affected tissues.

The anti-FcRn antibodies described herein (e.g., N022-N024, N026, and N027, preferably N027 and/or N024) may be administered to a pregnant subject who has or is at risk of having a medical condition that activates an immune response in the pregnant subject. In some embodiments, the pregnant subject may have had, in the past, a medical condition that activated an immune response in the pregnant subject. In some embodiments, the pregnant subject has a history of having had a previous fetus or neonate that had a fetal and neonatal alloimmune and/or autoimmune disorder. In some embodiments, the anti-FcRn antibodies described herein may be administered to a pregnant subject if a pathogenic antibody associated with an immune disease is detected in a biological sample (e.g., a blood or urine sample) obtained from the pregnant subject. In some embodiments, the pathogenic antibody detected in the biological sample of the pregnant subject is known to bind to an antigen from the fetus in the pregnant subject (e.g., an antigen that the fetus inherited from the fetus' father).

In some embodiments, the anti-FcRn antibodies described herein (e.g., N022-N024, N026, and N027, preferably N027 and/or N024) may be administered to a subject who is planning to become pregnant and who has or is at risk of having a medical condition that activates an immune response in the pregnant subject, and/or who has had, in the past, a medical condition that activated an immune response in the pregnant subject. In some embodiments, a subject is planning to become pregnant and has a history of having had a previous fetus or neonate that had a fetal and neonatal alloimmune and/or autoimmune disorder. In some embodiments, the anti-FcRn antibodies described herein may be administered to a subject who is planning to become pregnant and whose biological sample contains a pathogenic antibody associated with an immune disease.

In some embodiments, the anti-FcRn antibodies described herein may be administered to a subject (e.g., a pregnant subject) to reduce or treat an immune complex-based activation of an acute or chronic immune response in the subject. The acute immune response may be activated by a medical condition (e.g., pemphigus vulgaris, lupus nephritis, myasthenia gravis, Guillain-Barré syndrome, antibody-mediated rejection, catastrophic anti-phospholipid antibody syndrome, immune complex-mediated vasculitis, glomerulitis, a channelopathy, neuromyelitis optica, autoimmune hearing loss, idiopathic thrombocytopenia purpura, autoimmune haemolytic anaemia, immune neutropenia, dialated cardiomyopathy, serum sickness, chronic inflammatory demyelinating polyneuropathy, systemic lupus, reactive arthropathies, primary biliary cirrhosis, ulcerative colitis, or antineutrophil cytoplasmic antibody (ANCA)-associated vasculitis).

In some embodiments, the anti-FcRn antibodies described herein may be administered to a subject (e.g., a pregnant subject) to reduce or treat an immune response activated by an autoimmune disease. The autoimmune disease may be, for example, alopecia areata, ankylosing spondylitis, antiphospholipid syndrome, Addison's disease, hemolytic anemia, warm autoimmune hemolytic anemia (wAIHA), anti-factor antibodies, heparin induced thrombocytopenia (HICT), sensitized transplant, autoimmune hepatitis, hepatitis, Behcet's disease, bullous pemphigoid, cardiomyopathy, celiac sprue-dermatitis, chronic fatigue immune dysfunction syndrome, chronic inflammatory demyelinating polyneuropathy, Churg-Strauss syndrome, cicatricial pemphigoid, limited scleroderma (CREST syndrome), cold agglutinin disease, Crohn's disease, dermatomyositis, discoid lupus, essential mixed cryoglobulinemia, fibromyalgia, fibromyositis, Graves' disease, Hashimoto's thyroiditis, hypothyroidism, inflammatory bowel disease, autoimmune lymphoproliferative syndrome, idiopathic pulmonary fibrosis, IgA nephropathy, insulin dependent diabetes, juvenile arthritis, lichen planus, lupus, Ménière's Disease, mixed connective tissue disease, multiple sclerosis, pernicious anemia, polyarteritis nodosa, polychondritis, polyglandular syndromes, polymyalgia rheumatica, polymyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, stiff-man syndrome, Takayasu arteritis, temporal arteritis, ulcerative colitis, uveitis, vitiligo, or Wegener's granulomatosis.

EXAMPLES

Example 1—Antibody Production

IgG heavy and light chain nucleic acid molecules were cloned in vector pCDNA 3.3 using osteonectin secretion signals. HEK 293F cells were grown in Expi293 media at 37° C. with 8% $CO_2$. Cells were transfected at a density of $3 \times 10^6$/ml with 1 mg total DNA per liter. Enhancers were added on days 2 and 3 following manufacturer's directions and the cells were cultured until day 5 or 6 before cell viability dropped to below 50% to 60%. The cells were then spun out by centrifugation and the spent media was sterile filtered and stored at 4° C. until antibody purification. Antibodies were purified by a two-column procedure: POROS Protein A chromatography followed by POROS HS-50 cation exchange chromatography. The former separated most of the host cell proteins from the expressed antibodies while the latter removed the heavy chain dimers, light chain dimers, and half antibodies, as well as higher molecular weight species. The fractions from the HS-50 cation exchange column were pooled based on an SDS-PAGE gel analysis to maximize purity of the full length antibodies. The collected fractions were put over a Sephadex G50 buffer exchange column equilibrated in PBS at pH 7.2. The peak fractions were pooled and concentrated to greater than 10 mg/ml using 30 kDa spin concentrators and frozen at −30° C. in 2 mg and 5 mg aliquots. The final protein samples were checked for purity by SDS-PAGE.

Example 2—Binding Affinities

Through affinity maturation, we identified more than 100 anti-FcRn antibodies having binding affinities to human FcRn with a $K_D$ in the sub-micromolar range. Five antibodies (N022-N024, N026, and N027) were selected for further characterization. Surface Plasmon Resonance (SPR) was used to determine the on- and off-rates ($k_a$ and $k_d$, respectively) for each of these five antibodies. Briefly, a Bio-Rad GLC sensor chip was inserted into the ProteOn XPR 36 and air initialized. After initialization the running buffer was switched to freshly prepared buffer, either HBSP+ (0.01 M HEPES, 0.15 M NaCl, 0.05% P20, pH 7.4) or Sodium Phosphate Buffer (0.02 M Sodium Phosphate, 0.15 M NaCl, 0.05% P20, pH 6.0) as appropriate, which was used for the remainder of the assay and for all dilutions. The chip was preconditioned using one injection each of 0.5% SDS, 50 mM NaOH and 10 mM HCl at 30 µl/min for 60 seconds (s). A mouse anti-Human Fc mAb from GE Healthcare (BR100839) was diluted to 10 µg/ml in 10 mM acetate buffer pH 5.0 and approximately 5,700 response units (RU) was immobilized using standard amine coupling chemistry in the horizontal orientation onto a GLC sensor chip. The anti-hFcRn mAbs to be tested were captured onto the surface in the vertical orientation, with the goal of immobilizing approximately 200 response units (RU) per interaction spot. The rhFcRn was diluted in a five-point three-fold dilution series starting at 1.25 µg/ml, leaving one lane as buffer-only for a double reference. The analyte was flowed across the sensor surface in the horizontal orientation at 100 µl/min for 240 s with a 3,600 s dissociation time. Regeneration was accomplished by injecting 3M $MgCl_2$ at 100 µl/min for 30 s in both the horizontal and vertical directions. These procedures were repeated for all ligands.

Data analysis was conducted using the ProteOn Manager software. Each interaction step was adjusted for the Y and X direction using the Auto Process tool, followed by interspot channel referencing to remove non-specific interactions and blank lane double referencing to remove assay drift. The data was fit using the Langmuir 1:1 kinetic model with a grouped Rmax. The $k_a$, $k_d$ and $K_D$ values obtained from ProteOn Manager in a single run were averaged and their percent CV was calculated in Microsoft Excel when the N was three or greater.

Table 3 shows that five anti-FcRn antibodies of the invention, N022, N022, N024, N026, and N027, all bind with high affinity to human FcRn at pH 7.4. The equilibrium dissociation constant, $K_D$, of the anti-FcRn antibodies of the invention ranged from 19.4 pM (N027) to 36.5 pM (N026) for binding to human FcRn at pH 7.4. Table 3 also shows the rapid on-rates and slow off-rates of the five anti-FcRn antibodies. At pH 7.4, the on-rates were in the range of 0.93-1.42×10⁶ 1/Ms for binding to human FcRn. The off-rates were in the range of 2.31-4.44×10⁶ 1/s.

TABLE 3

| | $k_a$ (1/Ms) | $k_d$ (1/s) | $K_D$ (M) | $R_{max}$ | Chi2 | $K_D$ (pM) |
|---|---|---|---|---|---|---|
| N022 | 1.42E+06 | 4.42E-05 | 3.10E-11 | 146.93 | 7.65 | 31 |
| N023 | 9.27E+05 | 2.91E-05 | 3.14E-11 | 193.43 | 5.26 | 31.4 |
| N024 | 1.13E+06 | 4.03E-05 | 3.55E-11 | 181.17 | 6.12 | 35.5 |
| N026 | 1.22E+06 | 4.44E-05 | 3.65E-11 | 163.9 | 5.68 | 36.5 |
| N027 | 1.19E+06 | 2.31E-05 | 1.94E-11 | 211.33 | 7.81 | 19.4 |

Example 3—IgG Competition

The ability of anti-FcRn antibodies of the invention to compete with IgG for binding to human or cynomolgus monkey FcRn was evaluated on human embryonic kidney (HEK) 293 cells ectopically expressing cell surface, glyco-phosphatidylinositol (GPI)-linked FcRn. Human and cynomolgus monkey FcRn alpha amino acid sequences exhibit 97.5% sequence identity. Nine amino acid residues of 355 are different between human and cynomolgus monkey FcRn alpha, but none are in the epitope-mapped binding region. The level of cell-bound IgG was determined using 66 nM of fluorescent probe-labeled, non-specific IgG. The binding of IgG to cell surface FcRn was done at pH 6.0, which allows the Fc portion of IgG to interact with FcRn. As shown in FIG. 1, the amount of cell-bound IgG significantly decreased as the concentration of the anti-FcRn antibody (N022-N024, N026, or N027) increased. The binding of IgG was inhibited in a concentration- and saturation-dependent manner by each of the five exemplary anti-FcRn antibodies of the invention, demonstrating the ability of the anti-FcRn antibodies, N022-N024, N026, and N027, to effectively compete with and inhibit binding of IgG to FcRn at pH 6.0. The EC50 values of the antibodies ranged between 2 and 6 nM.

Example 4—Effect of Anti-FcRn Antibodies on IgG Catabolism in Mice

Figure 2:
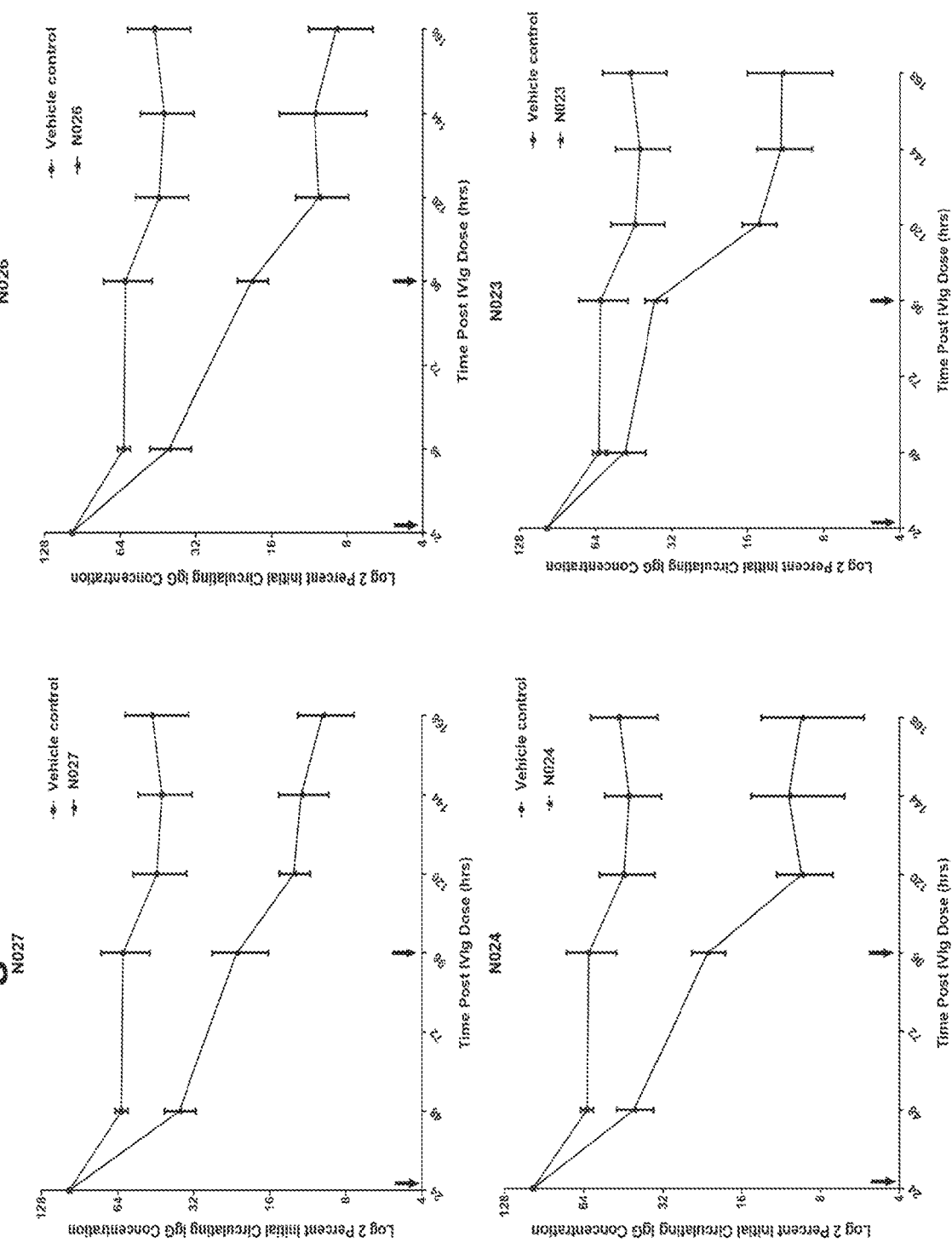
FIG. 2 includes graphs that show the effects of antibodies N023, N024, N026, and N027 on IgG catabolism in mice.

To measure the effect of the anti-FcRn antibodies of the invention on IgG catabolism in vivo, human FcRn transgenic mouse strain FcRn−/−hFcRn (32) Tg mice, which lacks mouse FcRn but expresses human FcRn in a tissue distribution similar to the endogenous mouse and human FcRn, was used. FcRn−/−hFcRn (32) Tg mice injected with 500 mg/kg human IgG on day 0 were administered a single dose of an anti-FcRn antibody at 10 mg/kg on days 1 and 4. As shown in FIG. 2, the catabolism of IgG was increased by the administration of anti-FcRn antibodies as seen by lower levels of IgG measured over time in anti-FcRn antibody-treated mice. The activities of N024 ($K_D$=35.5 pM), N026 ($K_D$=36.5 pM), and N027 ($K_D$=19.4 pM) appeared to be to be similar at 10 mg/kg.

Example 5—In Vitro and In Vivo Functional Characterizations of Anti-FcRn Antibodies In Vitro Cellular binding affinities of the antibodies of the invention were measured on human embryonic kidney (HEK) 293 cells ectopically expressing cell surface, glycophosphatidylinositol (GPO-linked human or cynomolgus monkey FcRn. FcRn is a type I transmembrane protein with the IgG and albumin binding domains oriented to the luminal side of endosomal membranes or to the cell surface when transported to the plasma membrane. The binding of anti-FcRn antibodies to cell surface, membrane-associated FcRn on HEK293 cells at pH 7.4 mimics binding in a physiologically-relevant environment and at the pH where only the Fab domain and not the Fc domain of the antibodies interact with FcRn. The FcRn extracellular domain was displayed on the cell surface at high density through a C-terminal engineered GPI linkage. The anti-FcRn antibodies of the invention were labeled with a fluorescent probe. The antibodies were allowed to bind for 30 minutes on ice. Cells were then washed at 4° C. and bound antibodies were detected using a fluorophore-labeled secondary antibody, e.g., a goat anti-human IgG F(ab)₂. The binding to human FcRn was concentration dependent and antibodies of the invention displayed EC50 values ranging from 4 to 7 nM.

Cellular binding affinities of the antibodies of the invention were also measured on endogenously expressed human FcRn. Monocytes express the highest levels of FcRn and show the highest percent positivity for FcRn expression in mouse and human blood. Monocytic cell line THP-1 was used to evaluate binding of anti-FcRn antibodies to endogenous human FcRn at pH 7.4. Since endogenous FcRn is primarily in intracellular endosomal vesicles in THP-1 cells, the cells were first permeablized with a mild detergent and fixed prior to incubation for 30 minutes at 4° C. with anti-FcRn antibodies in the presence of bovine serum to block non-specific Fc receptor binding. This assay was able to distinguish antibodies with better binding to endogenous human FcRn. The binding of anti-FcRn antibodies to THP-1 cells is concentration dependent. All antibodies of the invention, e.g., N022-N024, N026, and N027, showed better binding affinities than IgG1. Antibody N027 displayed the highest binding affinity with an EC50 value of 3.0 nM.

The ability of anti-FcRn antibodies of the invention to compete with IgG for binding to human or cynomolgus monkey FcRn was evaluated on human embryonic kidney (HEK) 293 cells ectopically expressing cell surface, GPI-linked FcRn. The level of cell-bound IgG was determined using fluorescent probe-labeled, non-specific IgG. The binding of IgG to cell surface FcRn was done at pH 6.0, which allows the Fc portion of IgG to interact with FcRn. As shown in Example 3 and FIG. 1, the amount of cell-bound IgG significantly decreased as the concentration of the anti-FcRn antibody increased. The binding of IgG was inhibited in a concentration- and saturation-dependent manner by each of the five exemplary anti-FcRn antibodies of the invention, e.g., N022-N024, N026, and N027, demonstrating the ability of the anti-FcRn antibodies to effectively compete with and inhibit binding of IgG to FcRn at pH 6.0. The EC50 values of the antibodies ranged from 2 to 6 nM.

Epitope mapping by hydrogen-deuterium exchange of the antibodies of the invention indicated that the antibodies bind to an epitope on human FcRn located in and/or adjacent to the Fc-FcRn interaction interface, which suggests that the antibodies of the invention block IgG binding to FcRn by direction inhibition. Furthermore, the epitope-mapped binding site is distant from the albumin-binding site of FcRn. An enzyme-linked immunosorbent assay (ELISA) was used to confirm that the antibodies of the invention do not inhibit serum albumin binding to FcRn. Soluble His-tagged extracellular domain of human FcRn was bound to the plate surface and pre-incubated with increasing concentrations of anti-FcRn antibody at pH 6.0. Horseradish peroxidase (HRP)-conjugated human serum albumin was allowed to bind to the soluble, His-tagged FcRn. None of the antibodies inhibited albumin binding to FcRn. Furthermore, in vivo experimental evidence also showed that mouse albumin levels remained constant after anti-FcRn antibody administration, indicating that albumin recycling was not disturbed by antibody binding to FcRn.

In Vivo

To test the in vivo effect of anti-FcRn antibodies of the invention on IgG catabolism, human FcRn transgenic mouse strain FcRn−/−hFcRn (32) Tg mice, which lack mouse FcRn but express human FcRn in a tissue distribution similar to that of the endogenous mouse and human FcRn, were used. FcRn−/−hFcRn (32) Tg mice injected with human IgG on day 0 were administered a single dose of an anti-FcRn antibody at 10 mg/kg on days 1 and 4. As shown in Example 3 and FIG. 2, the catabolism of IgG was increased by the administration of anti-FcRn antibodies as seen by lower levels of IgG measured over time in anti-FcRn antibody-treated mice. The activities of N024 ($K_D$=35.5 pM), N026 ($K_D$=36.5 pM), and N027 ($K_D$=19.4 pM) appeared to be to be similar at 10 mg/kg.

Figure 3:
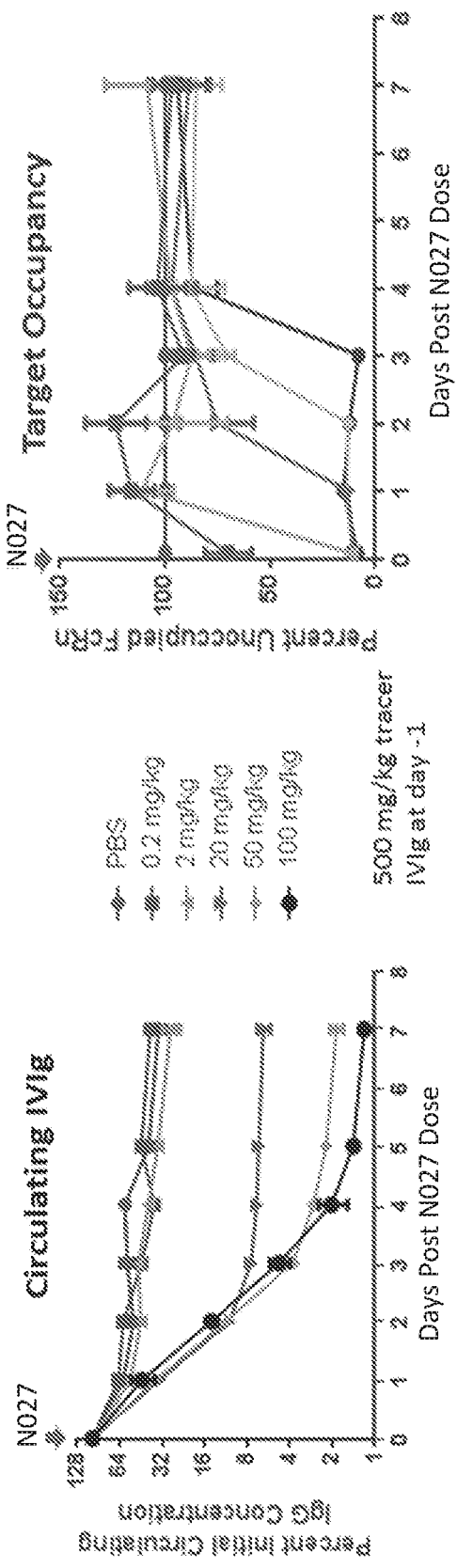
FIG. 3 includes graphs that show the dose-dependent effects of antibody N027 on IgG levels and target occupancy in mice.

Example 6—Effect of Anti-FcRn Antibodies on IgG Levels and Target Occupancy in Mice N027 was dosed intravenously (i.v.) 24 hrs after administration of 500 mg/kg IVIg (tracer) to Tg32 human FcRn (hFCGRT) transgenic, mouse FcRn (mFCGRT) knockout mice. Circulating human IgG was detected by ELISA on each day. Target occupancy was measured on each day in monocytes from lysed whole blood by fluorescence-activated cell sorting (FACS), after incubation of cells with immunophenotyping cell surface markers followed by fixation and permeabilization. Unoccupied FcRn was measured by staining with Dy650-labeled N027 (n=4 males per group). As shown in FIG. 3, IgG level and the percentage of unoccupied FcRn were decreased by the administration of N027 in a dose-dependent manner.

Figures 4A, 4B, 4C:
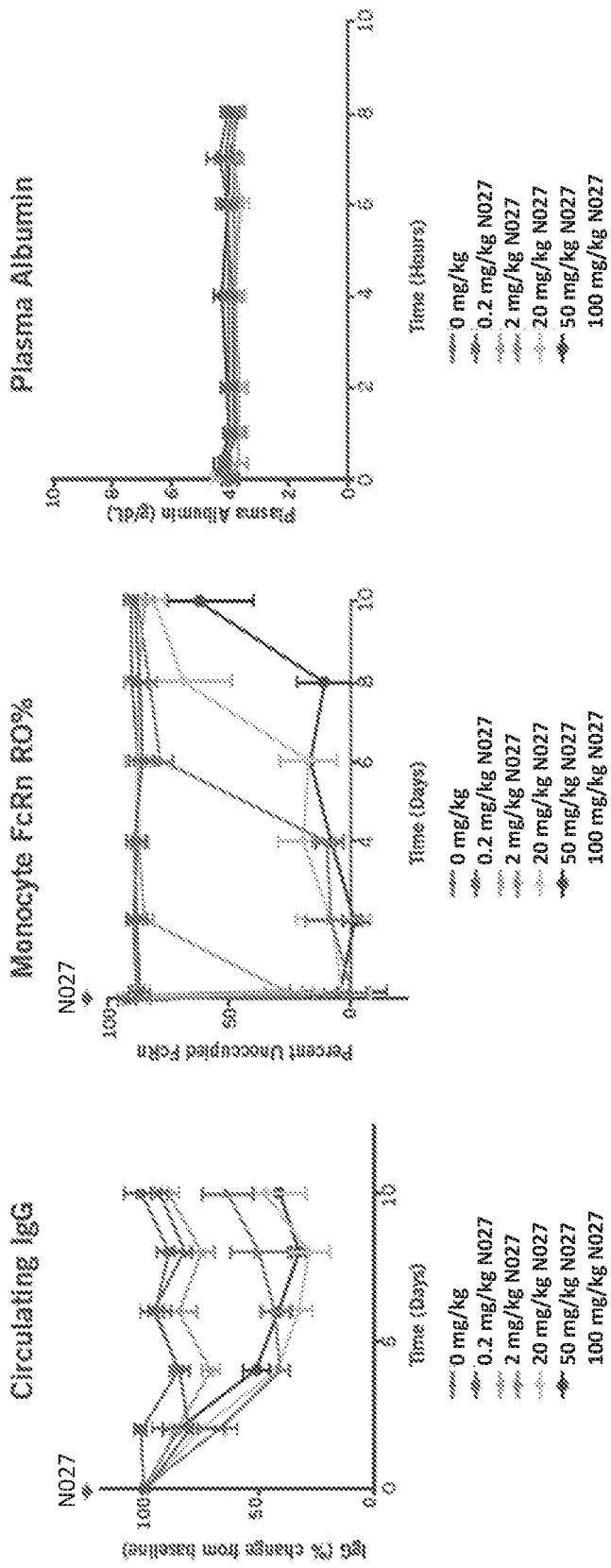
FIGS. 4A-4C includes graphs that show the selective induction of IgG catabolism and target occupancy in cynomolgus monkeys following administration of different doses of antibody N027.

Example 7—Selective Induction of IgG Catabolism and Target Occupancy in Cynomolgus Monkeys N027 was dosed i.v. at t=0 in cynomolgus monkeys. Circulating endogenous IgG and albumin was detected by ELISA. Target occupancy was measured in monocytes from lysed whole blood by FACS, after incubation of cells with immunophenotyping cell surface markers followed by fixation and permeabilization. Unoccupied FcRn was measured by staining with Dy650-labeled N027. (n=3 males per group). As shown in FIG. 4, IgG level and the percentage of unoccupied FcRn were decreased by the administration of N027 in a dose-dependent manner, while plasma albumin level stayed unchanged.

Example 8—Biodistribution of N027 in Mice

Figure 5:
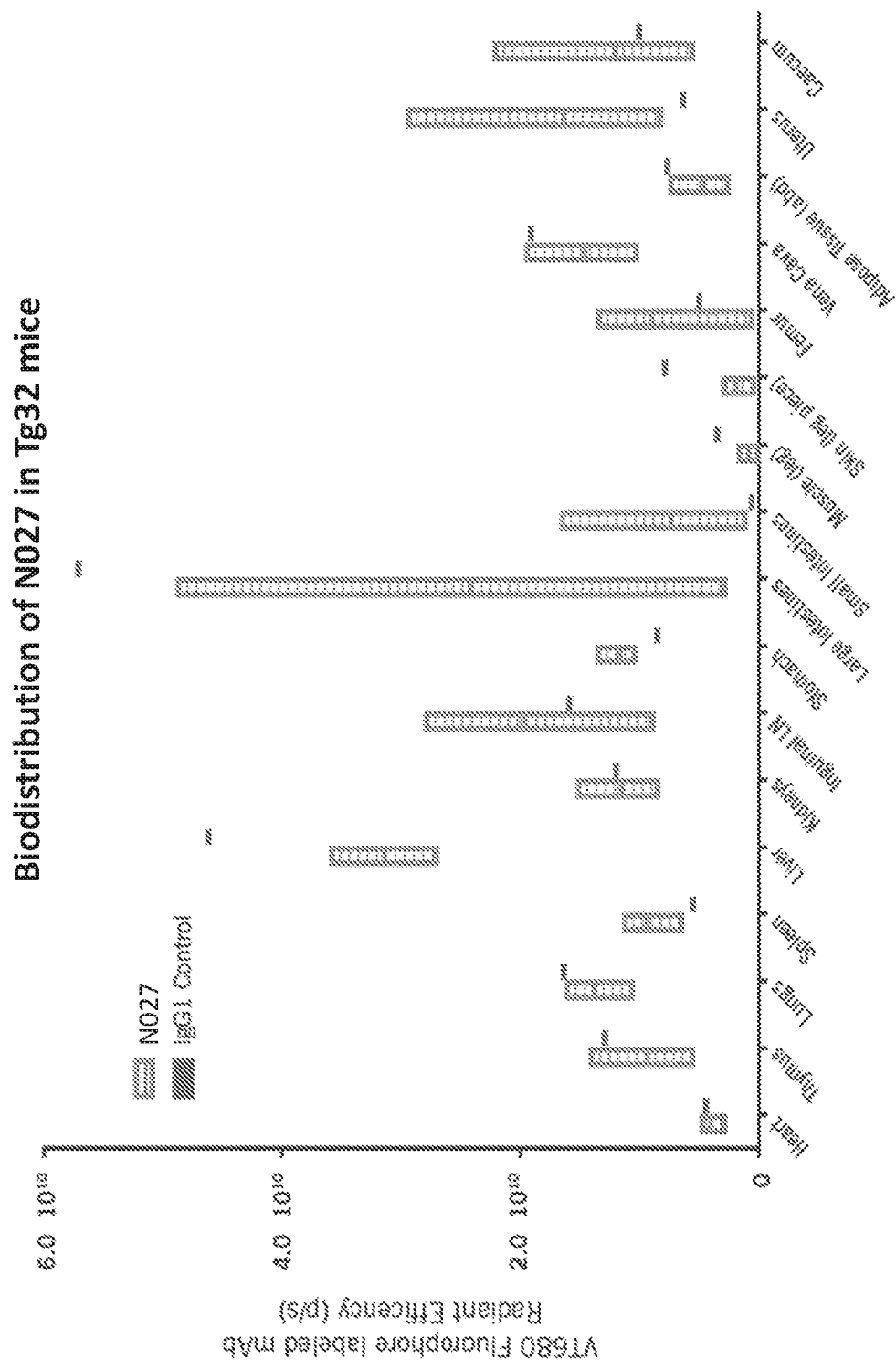
FIG. 5 includes a graph that shows the biodistribution of N027 in mice.

N027 or isotype human IgG1 control antibody labeled with fluorophore (VT680) was administered i.v. to Tg32 human FcRn transgenic, mouse FcRn knockout mice at 30 mg/kg. Levels of labeled antibody were measured in individual organs by quantitative ex vivo optical imaging. FIG. 5 shows the biodistribution of N027 in various organs in mice.

Example 9—Efficacy of N027 in Mouse Collagen Antibody-Induced Arthritis

Figure 6:
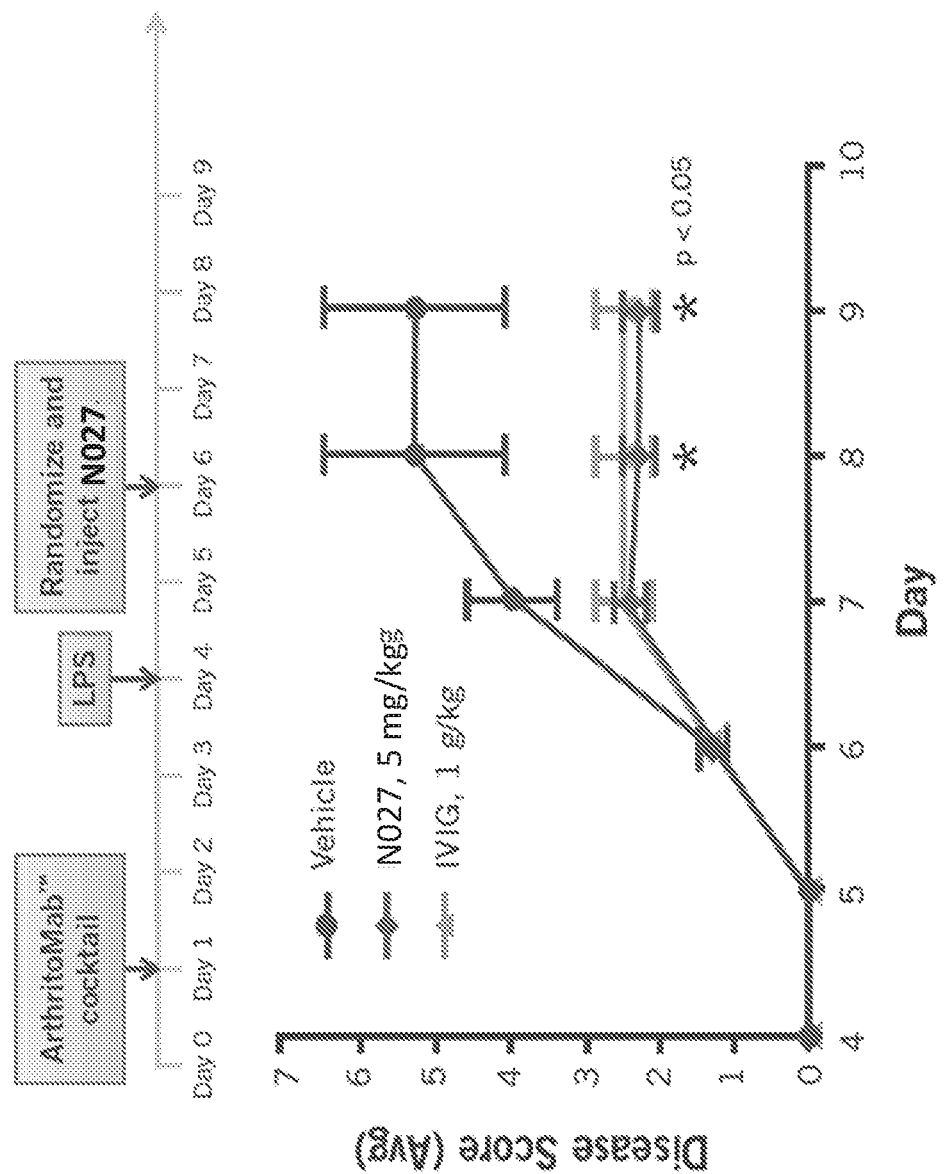
FIG. 6 includes an experimental timeline and a graph that shows the efficacy of N027 in a mouse collagen antibody-induced arthritis model.

Collagen antibody-induced arthritis was induced in Tg32 human FcRn transgenic, mouse FcRn knockout mice by intraperitoneal (i.p.) injection of ArthritoMar cocktail (MD Biosciences) on day 1 and inflammatory disease activity induced with 100 µg LPS i.p. on day 4. N027 was dosed therapeutically i.v. at 5 mg/kg (arrow), on day 6 post disease induction and randomization. IVIG at 1 g/kg (positive control group) or vehicle-PBS (negative control) were dosed on day 6 after randomization (n=5 per group). As shown in FIG. 6, N027 potently inhibits collagen antibody-induced arthritis in human transgenic FcRn mice when dosed therapeutically.

Example 10—Efficacy of N027 in Mouse Chronic Idiopathic Thrombocytopenia Purpura (ITP)

Figure 7:
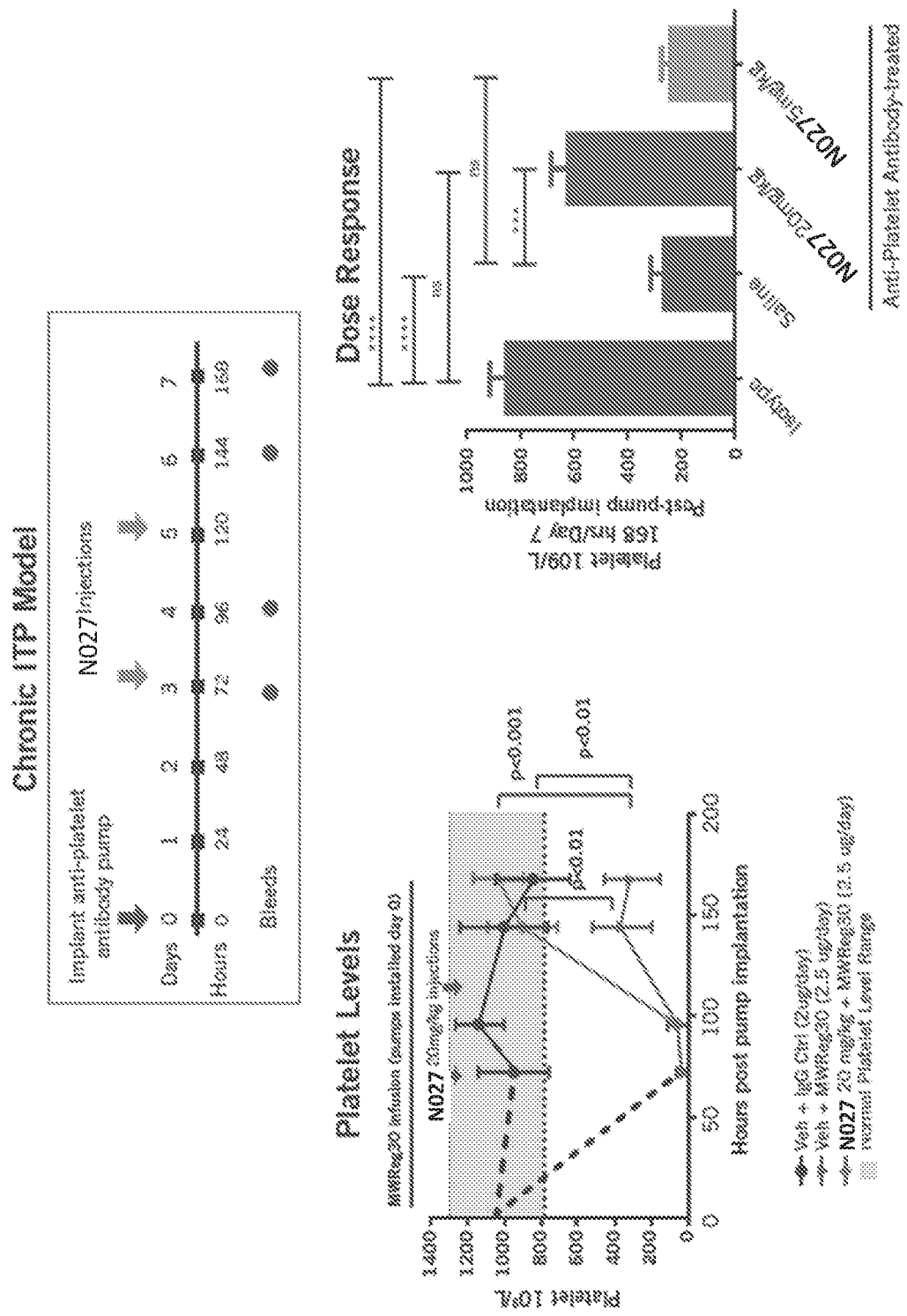
FIG. 7 includes an experimental timeline and two graphs that show the efficacy of N027 in a mouse chronic idiopathic thrombocytopenia purpura (ITP) model.

Thrombocytopenia was induced in Tg32 human FcRn (hFCGRT) transgenic, mouse FcRn (mFCGRT) knockout mice by continuous infusion of anti-platelet antibody (anti-CD41, MWReg30) subcutaneous (s.c.) miniosmotic pump. Circulating platelet levels were decreased to 300×109/L or less by 72 hrs (Day 3) after pump implantation. N027 was dosed therapeutically i.v. 72 hrs (day 3) and 120 hrs (Day 5) post-pump implantation (A, n=4 per group; B, n=7 per group). FIG. 7 shows the effects of N027 on platelet levels in mice having thrombocytopenia.

Figures 8A, 8B, 8C:
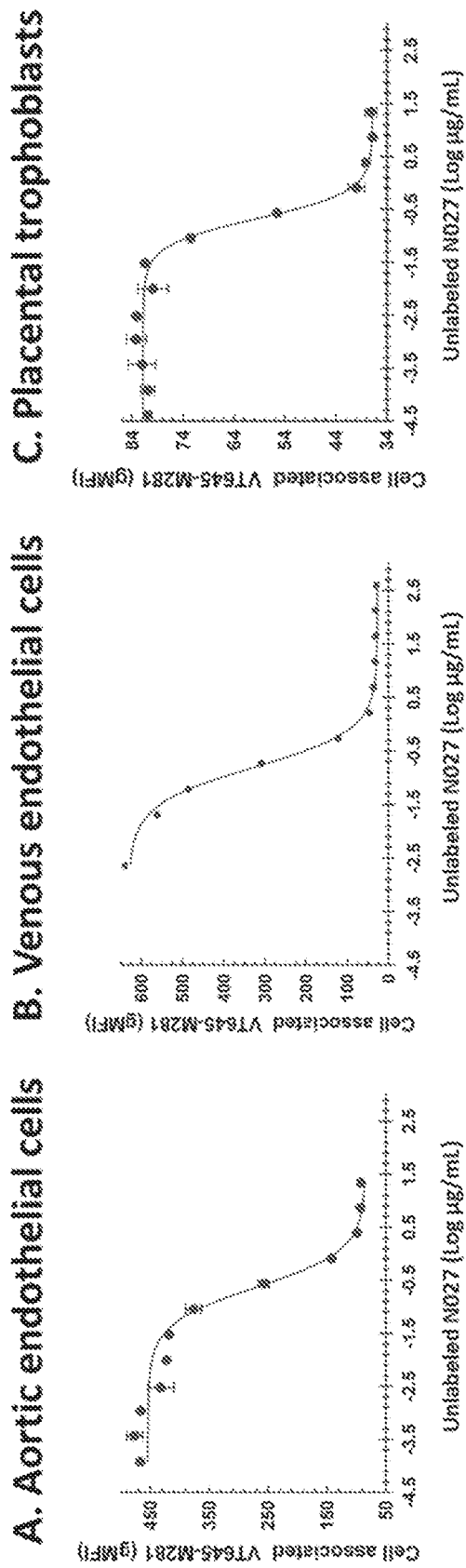
FIGS. 8A-8C show graphs that show the dose-dependent FcRn occupancy achieved with N027 in aortic endothelial cells, venous endothelial cells, and placental trophoblast, respectively.

Example 11—Concentration Dependent FcRn Occupancy was Achieved with N027 in Target Cell Types The receptor occupancy by N027 was compared across different cell types such as primary human aortic endothelial cells (HAECs), human umbilical vein endothelial cells (HUVECs) cells and placental trophoblasts (HVTs). Cells were grown to confluency in complete EBM-2 media (Lonza, Waterville) or in trophoblast media (ScienCell). Cell monolayers were incubated in 1 ml of media with different concentrations of unlabeled N027 for 1 hour at 37° C. After washing, cells were harvested with cold HyQTase, fixed and permeabilized before incubation with VivoTag645-labeled N027 (10 µg/ml), for 30 minutes at 4° C. in the dark. Following incubation, cells were washed with permeabilization buffer before resuspending in FACS buffer. Cell-associated VivoTag645-N027 was measured by flow cytometry. The values represent geometric mean fluorescence intensity (gMFI)±SD (n=2). FIGS. 8A, 8B, and 8C show the FcRn occupancy across N027 concentrations for the HAECs, HUVECs and HVTs, respectively. The results as summarized in Table 4 show that human ECs (HAECs, HUVECs) as well as placental HVTs exhibit similar concentration dependence receptor occupancy by N027.

TABLE 4

| Human Primary Cells | $IC_{50}$ | 100% FcRn occupancy dose |
| --- | --- | --- |
| Aortic endothelial cells (HAECs) | 0.23 µg/mL | 2.43 µg/mL |
| Venous endothelial cells (HUVECs) | 0.15 µg/mL | 4.99 µg/mL |
| Placental trophoblast cells (HVTs) | 0.15 µg/mL | 2.43 µg/mL |

Example 12—N027 Concentrations Achieving 100% Receptor Occupancy Result in Increased Intracellular IgG Accumulation The relation between levels of receptor occupancy and alterations in IgG intracellular trafficking by N027 was compared across different cell types. Human endothelial cells (HAECs and HUVECs) were cultured in endothelial cell culture (EBM-2, Lonza) while human placental trophoblasts (HVTs) were cultured in trophoblast media (ScienCell). Cell monolayers were then pulsed for 4-5 hours at 37° C. in 1 mL media containing either:

1. varying concentrations of N027+VivoTag645-IgG (50 µg/mL); or
2. varying concentrations of Isotype control IgG+VivoTag645-IgG (50 µg/mL)

Figure 9A:
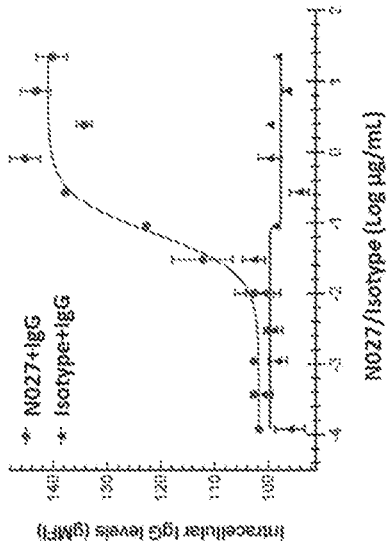
FIGS. 9A-9C show graphs that show 100% FcRn occupancy by N027 results in increased intracellular IgG accumulation in aortic endothelial cells, venous endothelial cells, and placental trophoblast, respectively.
Figure 9B:
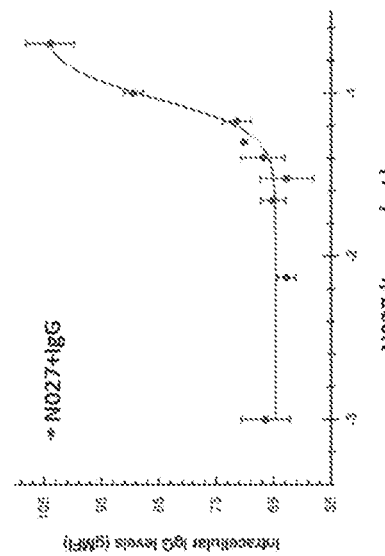
Figure 9C:
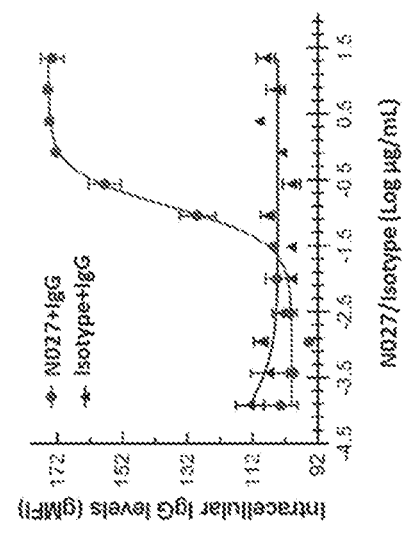

Cell monolayers were then washed in cold media followed by cell detachment by HyQtase treatment. Cell associated VivoTag645-N027 was measured by flow cytometry. Values represent geometric mean fluorescence intensity (gMFI)±SD (n=2). FIGS. 9A, 9B, and 9C show the intracellular IgG levels for the HAECs, HUVECs and HVTs, respectively, corresponding to various doses of N027. N027 doses corresponding to >100% FcRn occupancy resulted in significantly higher IgG accumulation compared to isotype controls. The results demonstrate that the effective N027 concentrations needed to achieve saturating levels of IgG accumulation is similar in these target cell types and ranges from 4.99 to 2.43 µg/mL as summarized in Table 5

TABLE 5

| Human Primary Cells | $\sim IC_{50}$ | 100% FcRn occupancy dose |
| --- | --- | --- |
| Aortic endothelial cells (HAECs) | 0.12 µg/mL | 2.43 µg/mL |
| Venous endothelial cells (HUVECs) | 0.15 µg/mL | 4.99 µg/mL |
| Placental trophoblast cells (HVTs) | 0.07 µg/mL | 3.68 µg/mL |

Example 13—Measurement of Time to 100% FcRn-Occupancy

To determine the time taken by N027 to saturate FcRn and block IgG trafficking, confluent vascular endothelial cell (HUVEC) monolayers were incubated with or without a saturating concentration of N027 (16.6 µg/ml) in EBM-2 media for the indicated times at 37° C. (FIG. 10). Upon completion of incubation, cells were washed and harvested with cold HyQtase, followed by fixing and permeabilization. These cells were then incubated in permeabilization buffer+ 10% human serum and VivoTag645-labeled N027 (10 µg/mL) for 30 minutes at 4° C. in the dark. The cells were then washed with permeabilization buffer, resuspended in FACS buffer and cell-associated VivoTag645-N027 was measured by FACS. Values represent mean gMFI±SD (n=2). The results shown in FIG. 10 indicates that 100% FcRn-occupancy by N027 was achieved in about 30 minutes in this endothelial cell type.

Example 14—Human Vascular Endothelial Cells and Placental Trophoblasts Exhibit Similar FcRn Turnover Rates which are Unaltered by N027

Figure 11A:
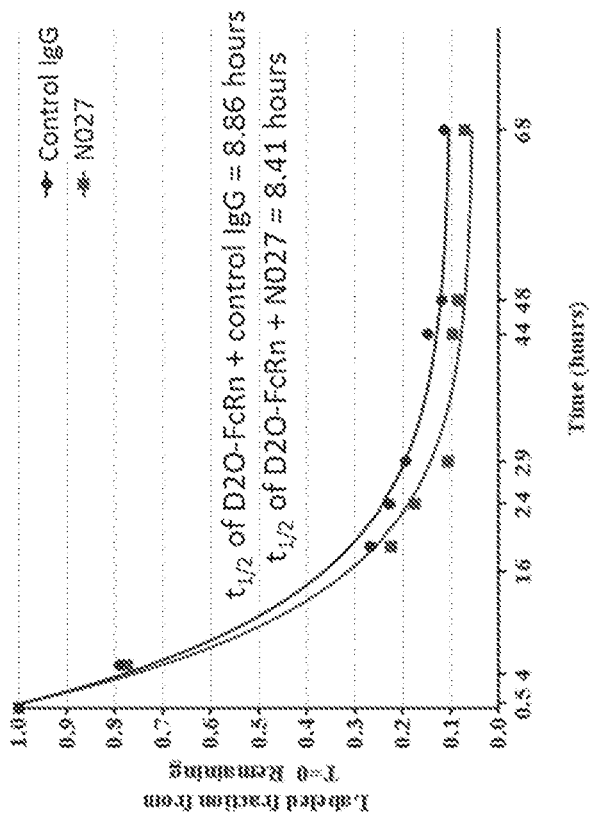
FIGS. 11A and 11B show graphs that show N027 treatment does not alter FcRn turnover rates in human endothelial and villous trophoblast cells, respectively.
Figure 11B:
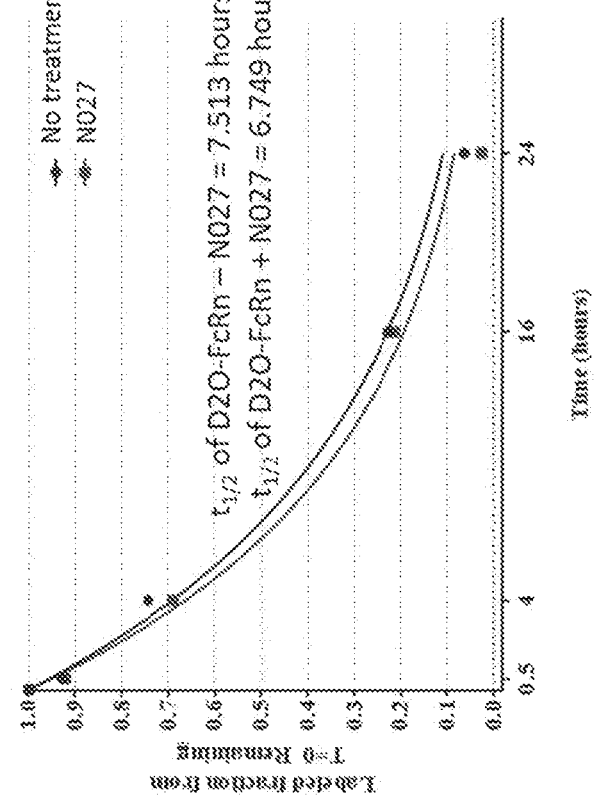

The FcRn turnover rates of human vascular endothelial cells (HUVECs) and placental trophoblasts (HVTs) were compared in the presence and absence of N027. Cells were cultured in 75 cm² flask in 25% D20 (Deuterium Oxide, from Aldrich) containing media for three days. After three days, the media was replaced with normal media containing N027 (100 µg/mL) or control IgG (100 µg/ml) or mock treatment. Cells were then harvested from the flasks at indicated times post media change (FIGS. 11A and 11B). The cell monolayers were washed; cells were harvested, pelleted, and individual pellets were lysed and digested separately. Shotgun proteomics and targeted proteomics were performed. Using Qual Browser, isotopic relative intensities were extracted and fractional abundances were calculated for each isotopomer by dividing each intensity by the total. Fractional abundance values were used to calculate the percentage of D20-labeled FcRn remaining in the system. FIGS. 11A and 11B show that FcRn turnover rates are similar between human vascular endothelial cells (HUVECs) and placental trophoblasts (HVTs). Furthermore, treatment with N027 did not change the FcRn turnover rates.

Example 15—FcRn Localization in Target Cells

Figure 12A:
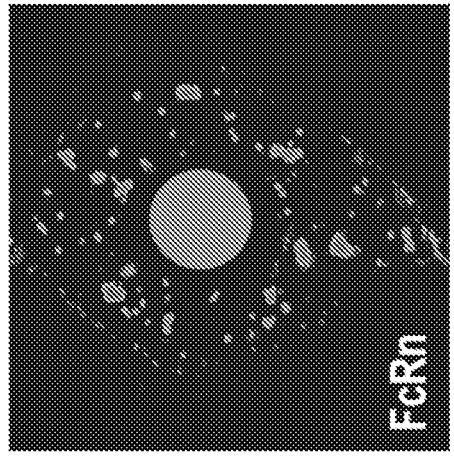
FIGS. 12A and 12B show images of FcRn localized in endosomes in human endothelial and villous trophoblast cells.
Figure 12B:
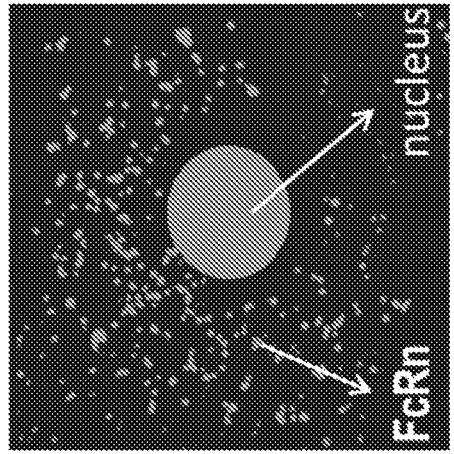

The localization of N027 was compared in human vascular endothelial cells (HUVECs) and placental trophoblasts (HVTs). Cells were grown on glass coverslips in EBM-2/ TM media. Live cells were incubated in media containing DyLight594-N027 (2 µg/mL) for 1 hour at 37° C. Cells were then washed and imaged live on fluorescence microscope in confocal mode with 60× dry objective using appropriate filters. Representative single cell images show similar localization pattern of N027 bound to the endocytic pool of FcRn in both cell types (FIGS. 12A and 12B). The circle in the center of the cell indicates the location of the nucleus.

Figures 13A, 13B:
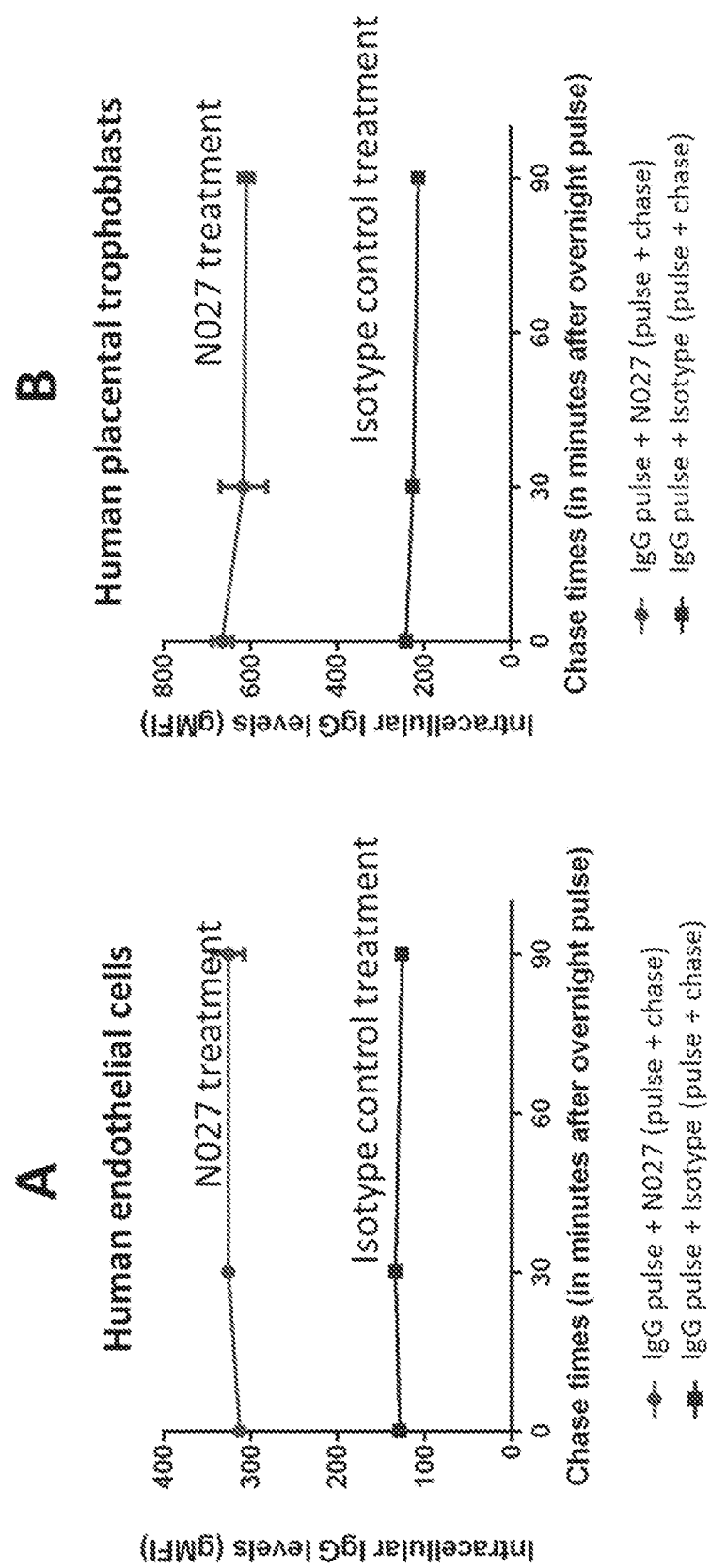
FIGS. 13A and 13B show graphs that show the effect of N027 treatment on dynamics of IgG trafficking in human endothelial cells and human placental trophoblasts, respectively.

Example 16—Effect of N027 Treatment on Dynamics of IgG Trafficking: Intracellular IgG Accumulation and Co-Localization with Lysosomes The effect of N027 treatment on dynamics of intracellular IgG accumulation was compared across FcRn expressing target cell types such as human vascular endothelial cells (HUVECs) and placental trophoblasts (HVTs). Cells were grown to confluency in EBM-2 media (Lonza, Waterville) or TM1 media (ScienCell). Confluent cell monolayers were then pulsed in 1 ml media containing either N027 (2 μg/ml)+VivoTag645-IgG (50 μg/mL) or isotype control IgG (2 μg/mL)+VivoTag645-IgG (50 μg/ml) for 20 hours at 37° C. Cell monolayers were then washed and then chased for 0 min, 30 min, and 90 min at 37° C. in chase media containing either N027 (2 μg/mL) or Isotype control (2 μg/ml). After each chase period, cells were washed, detached, and collected by HyQtase treatment. Cell-associated VivoTag645-N027 was measured by flow cytometry. Values represent geometric mean fluorescence intensity (gMFI)±SD (n=2). Cells treated with N027 showed higher levels of intracellular IgG. Further, the effect of N027 on the dynamics of intracellular IgG accumulation was similar between the two cells types tested as shown in FIGS. 13A and 13B.

Figure 13D:
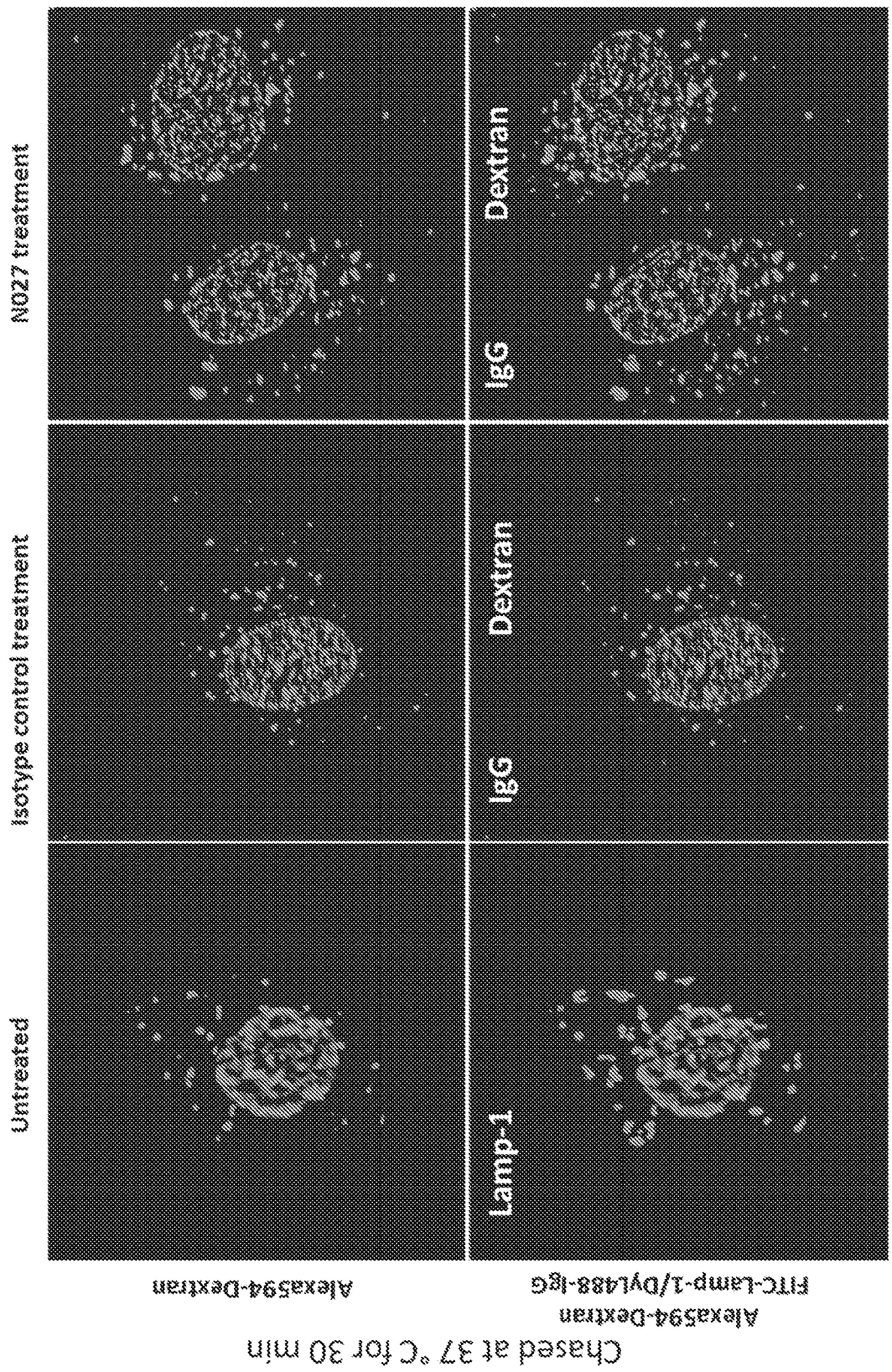

We also determined whether N027 increases intracellular IgG and co-localization of IgG with lysosomes in primary human umbilical vein endothelial cells (HUVECs). Cells were grown on glass coverslips and incubated in media containing 10 μg/ml Alexa Fluor 594 Dextran (10,000 MW, anionic, fixable) for 2 hours at 37° C. Following incubation cells were washed and pulsed at 37° C. for 20 hours in either N027 (2 μg/ml)+DyLight 488-IgG (50 μg/ml) containing media or Isotype control IgG (2 μg/ml)+DyLight 488-IgG (50 μg/ml) containing media; or in media without any IgG-treatments. The plates were washed in cold media and then chased for 0 min or 30 min at 37° C. The following chase conditions were used: the N027+DyLight 488-IgG pulsed set was chased in the presence of N027 (2 μg/mL); the Isotype+DyLight 488-IVIG pulsed set was chased in the presence of isotype control IgG (2 μg/mL) and the set without any IgG-treatments was chased in media only. Cells were washed, incubated in BD Cytofix/Cytoperm solution for 30 min at 4° C. in the dark, washed with perm wash buffer followed by incubation in perm wash buffer+10% normal mouse serum+5 μg/ml mouse anti-human Lamp1 antibody for overnight at 4° C. in the dark. Cells were then washed with perm wash buffer and PBS, and then mounted on glass slides. Cell imaging was done using confocal mode on Olympus fluorescence microscope with a 60× dry objective with 2× optical magnification. As presented in FIGS. 13C and 13D, it was shown that N027 treatment increases the accumulation of IgG in the lysosomal compartment as compared to isotype control IgG-treated cells.

Example 17—Suppression of Endogenous Maternal and Fetal IgG in Cynomolgus Monkeys by N027 and Lack of N027 Transfer to Fetal Circulation Pregnant female cynomolgus monkeys were dosed weekly from Gestation Day 45 (GD45) to C-section at GD100 (mid-gestation) or GD140 (late gestation). A cohort of animals was also included in the study that were allowed to deliver their infants (birth day [BD1]). The design study is depicted in Table 8.

TABLE 8

| | | | | | No. of Females for C-section[a] | | |
|---|---|---|---|---|---|---|---|
| Group No. | Test Material | Dose Level (mg/kg) | Dose Volume (mL/kg) | Dose Concentration (mg/mL) | GD100 ± 2 | GD140 ± 2 | Live Birth BD1 |
| 1 | Control | 0 | 10 | 0 | 4 | 4 | 3 |
| 2 | N027 | 100 | 10 | 10 | 4 | 4 | — |
| 3 | N027 | 300 | 10 | 30 | 4 | 4 | 3 |

[a]Twenty-four (24) pregnant females were initially enrolled on study (8 per group). Four pregnancies per group were assigned to the GD140 ± 2 C-section cohort, and the remaining 4 pregnancies per group were assigned to the GD100 ± 2 cohort.

IgG concentrations were measured in maternal and neonatal blood samples using a standard validated total IgG ELISA (Table 9). Briefly, polystyrene plates (96-well) were coated with commercially available anti-human IgG antigen. The coated plate(s) were washed to remove unbound sample and then blocked using with blocking buffer followed by a wash to remove the residual blocking buffer. Serum samples were diluted and added to the anti-human 193 coated wells and incubated at room temperature for 60±5 minutes. Each well was washed before addition of secondary (detection) antibody conjugated to horseradish peroxidase (HRP) and incubated at room temperature for 60±5 minutes. Tetramethylbenzidine (TMB) substrate was subsequently added to each well and incubated at room temperature for 20±5 minutes on a plate shaker, before addition of 2N $H_2SO4$ to stop the enzymatic reaction. The absorbance of each well was read at 450 nm using the SpectraMax® 190 microplate reader. Any commercially available or proprietary pair of anti-human IgG capture antibody and HRP conjugated anti-human IgG detection antibody that recognizes total IgG and is cross-reactive with cynomolgus monkey IgG can be used to measure total cynomolgus monkey IgG in an ELISA. The IgG detection antibody can be, for example, intact IgG, polyclonal serum antibody, monoclonal antibody, or a Fab (2) fragment.

TABLE 9

Methods

| Assay | Method |
|---|---|
| Total IgG ELISA | 1. Coat immunoassay plate with anti-human IgG.<br>2. Incubate with sample<br>3. Detect with HRP labeled and addition of TMB substrate |
| Receptor Occupancy by Fluorescence Activated Cell Sorting (FACS) | 1. Whole blood was treated with ammonium chloride to lyse RBC<br>2. Cells were spun, washed with PBS, stained with viability dye and incubated with Fc receptor blocking solution<br>3. Cells were washed with Perm/Wash buffer, suspended in buffer and incubated with fluor labeled N027 for 20 mins<br>4. Cells were then washed and resuspended in FACS buffer before analysis by FACS |

For all pregnant adult females assigned to study, blood was collected by venipuncture from the femoral vein (preferred) or cephalic/saphenous veins according to Table 10. For all fetuses obtained by C-section on GD100±2 or GD140±2, blood was collected from the umbilical cord according to Table 10. Samples (1 mL) were allowed to clot for at least 60 minutes; centrifuged and the resultant serum was separated, transferred to appropriately labeled (e.g., IgG) polypropylene tubes, and frozen immediately in a freezer set to maintain −80° C.

TABLE 10

Sample Collection Timepoints for Evaluation

| Gestation Day[b] | Time Points Relative to Dosing | Samples Collected |
|---|---|---|
| GD38 ± 1 (prestudy) | Prestudy | Adult female: IgG |
| GD44-46 (first dose) | Predose | Adult female: IgG |
| GD44-46 (first dose) | Postdose: 2 hr | Adult female: IgG |
| GD44-46 | Postdose: 4 hr | — |
| GD45-47 | GD45: 24 hr | Adult female: IgG |
| GD47-49 | GD45: 72 hr | Adult female: IgG |
| GD48-50 | GD45: 96 hr | Adult female: IgG |
| GD51-53 | GD52: Predose | Adult female: IgG |
| GD58-60 | GD59: Predose | Adult female: IgG |
| GD65-67 | GD66: Predose | Adult female: IgG |
| GD72-74 | GD73: Predose | Adult female: IgG |
| GD79-81 | GD80: Predose | Adult female: IgG |
| GD86-88 | GD87: Predose | Adult female: IgG |
| GD93-95 | GD94: Predose | Adult female: IgG |
| GD93-95[a] | GD94: 2 hr | Adult female: IgG |
| GD93-95[a] | GD94: 4 hr | — |
| GD94-96[a] | GD94: 24 hr | Adult female: IgG |
| GD96-98[a] | GD94: 72 hr | Adult female: IgG |
| GD97-99[a] | GD94: 96 hr | Adult female: IgG |
| GD100 ± 2 (1st C-section cohort) | NA | Adult female: IgG; Fetus: IgG |
| GD100-102 | GD101: Predose | Adult female: IgG |
| GD107-109 | GD108: Predose | Adult female: IgG |
| GD114-116 | GD115: Predose | Adult female: IgG |
| GD121-123 | GD122: Predose | Adult female: IgG |
| GD128-130 | GD129: Predose | Adult female: IgG |
| GD135-137 (last dose) | GD136: Predose | Adult female: IgG |
| GD135-137 | GD136: 2 hr | Adult female: IgG |
| GD135-137 | GD136: 4 hr | — |
| GD136-138 | GD136: 24 hr | Adult female: IgG |
| GD138-140 | GD136: 72 hr | Adult female: IgG |
| GD139-141 | GD136: 96 hr | Adult female: IgG |
| GD140 ± 2 | NA | Adult female: IgG |
| (2nd C-section cohort) Day of parturition (Maternal: PPD1) (Neonate: BD1) | NA | Fetus: IgG total Adult female: IgG Neonate: IgG |

[a]Time points were only collected from animals in the GD100 C-section cohorts.
[b]Collection ranges listed based on potential dose days of GD44 to 46. All time points were based off of the dose day.

Suppression of Endogenous Maternal IgG

Figure 16:
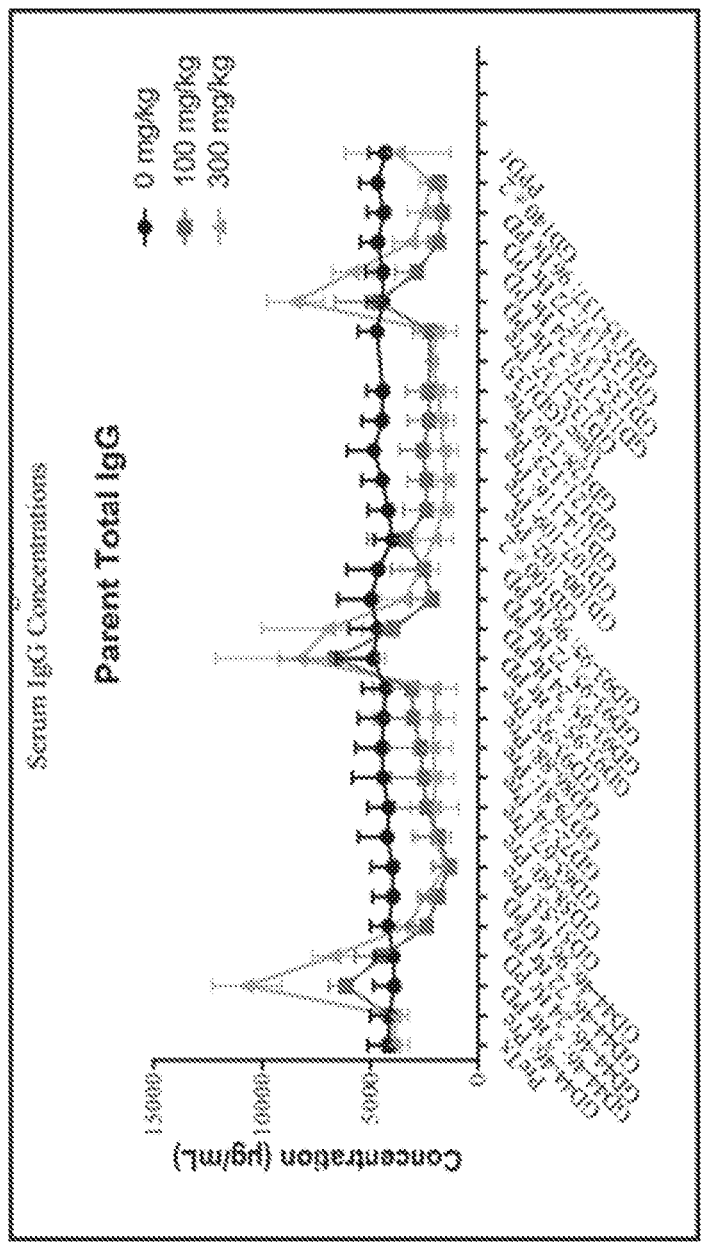
FIG. 16 is a graph showing maternal IgG concentrations after treatment with N027 during gestation.

N027 administration resulted in dose-independent reductions in serum IgG levels in adult females beginning 72 hours postdose, and the greatest reductions in serum IgG concentrations were observed for both the 100 and 300 mg/kg dosed animals at the GD51-53: predose time point (FIG. 16). The serum IgG values for Group 2 (100 mg/kg) trended toward predose levels in a dose-dependent manner, beginning at the GD65-67: predose time point and continuing until the next dose administrations on GD93-95 and GD135-137, after which, reductions of a similar magnitude were present within 72 hours of dosing. Group 3 animals (300 mg/kg) remained at a nadir IgG value at all pre-dose timepoints (as referred to in Table 10) throughout the dosing period. No change in IgG from baseline was observed in animals treated with vehicle (Group 1).

Figure 17:
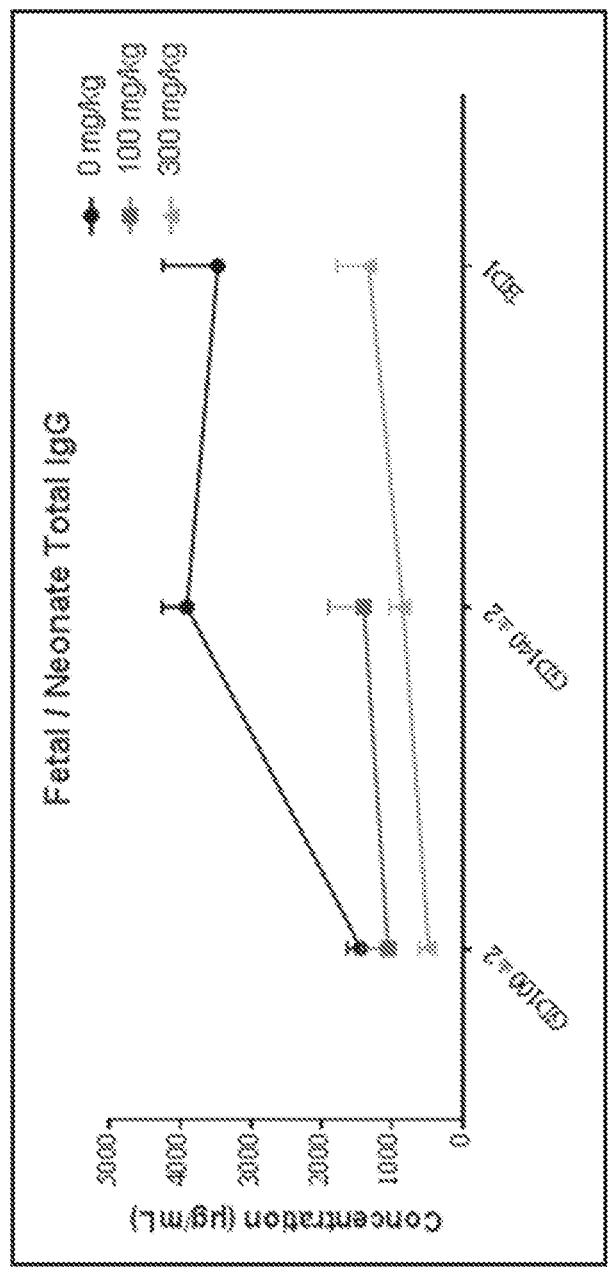
FIG. 17 is a graph showing fetal IgG levels after treatment of mothers with N027 during gestation.

Dose-dependent increases in serum IgG concentrations were present 2 hours after dose administration on GD44-46, GD93-95, and GD135-137. These increases were likely the result of the detection of N027 by the total IgG assay and were not considered to be related to the pharmacology of N027. Dose-dependent reductions in fetal serum IgG levels were present relative to control values at the GD100 and GD140, and in neonates at the BD1 time point (FIG. 17).

Lack of N027 Transfer from Maternal to Fetal Circulation

The transfer of N027 from maternal circulation to fetal circulation was evaluated by measuring the level of N027 FcRn occupancy in fetal circulating monocytes. N027 receptor occupancy was assessed on monocytes, granulocytes, B-lymphocytes, and T-lymphocytes using a flow cytometric (FACS) assay to measure the binding of fluorescent-labeled N027 to free/unbound FcRn in the presence and absence of saturating concentrations of N027. The unsaturated samples demonstrated the percentages of free or unbound FcRn receptor present on each leukocyte subset at each predose and postdose time point. The saturated samples were spiked with concentrations of unlabeled N027 that were determined to completely saturate any FcRn receptors that remained free/unbound at each postdose time point. N027 receptor occupancy was not detected in the whole blood of fetuses on day GD100 and GD140, or in neonates on BD1, in the context of the unsaturated sample analysis as described above.

Example 18—Evaluation of the Transplacental Transfer of N027

Human placenta obtained from uncomplicated term pregnancies were utilized in an ex-vivo dual perfusion single placental lobule method to evaluate the transplacental transfer of N027. Briefly, each placenta was examined for tears, and two chorionic vessels (one artery and vein) supplying a single intact peripheral cotyledon were cannulated with 3F and 5F umbilical catheters, respectively. The cotyledon was trimmed and placed in the perfusion chamber with the maternal surface upward. The intervillous space on the maternal side was perfused by two catheters piercing the basal plate. The flow rate of the perfusate medium in the fetal and maternal circuits was 3.0 and 12 mL/min, respectively. The maternal perfusate was equilibrated with a gas mixture made of 95% $O_2$ and 5% $CO_2$, and the fetal perfusate with a mixture of 95% $N_2$ and 5% $CO_2$. All experiments were carried out at a temperature of 37° C.

Each placental lobule was perfused for an initial control period of one hour to allow the tissue to stabilize to its new environment using an open-open configuration of the perfusion system. Perfusion was terminated if one of the following occurred during the control period: a volume loss in the fetal circuit in an excess of 3 mL/h, or a $pO_2$ difference between the fetal vein and the artery less than 60 mmHg, indicating inadequate perfusion overlap between the two circuits. The control period was followed by an experimental period of four hours using a closed-closed configuration (i.e., re-circulation of the medium) of the perfusion system. The latter was initiated by replacing the medium of the maternal and fetal reservoirs and the addition of 3 mg/ml of BSA.

Figure 14:
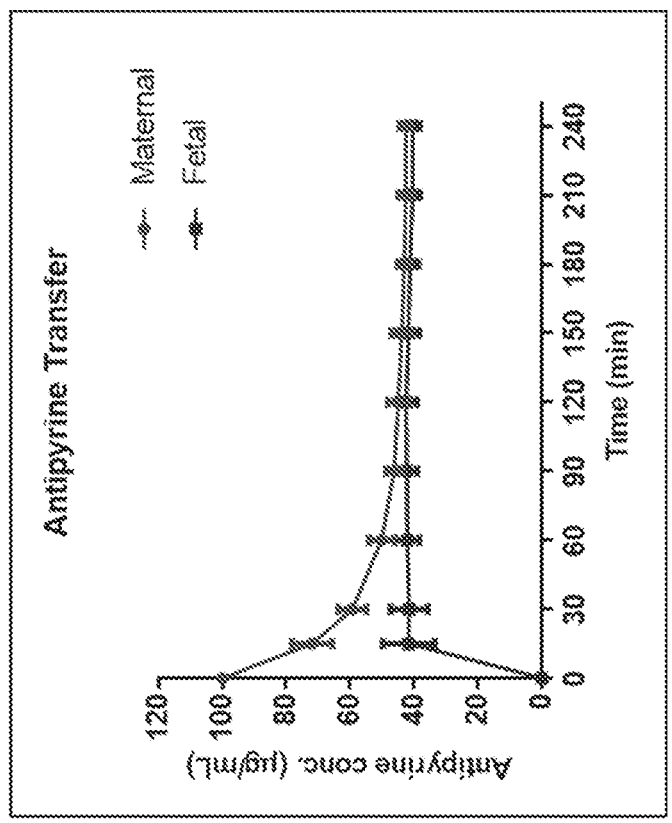
FIG. 14 is a graph that shows transplacental transfer of antipyrine over four hours of perfusion (n=14). The data represent antipyrine concentrations as mean±standard deviation (SD) in the fetal (squares) and maternal (circles) circulation after maternal administration of 100 µg/ml antipyrine at t=0.
Figure 15:
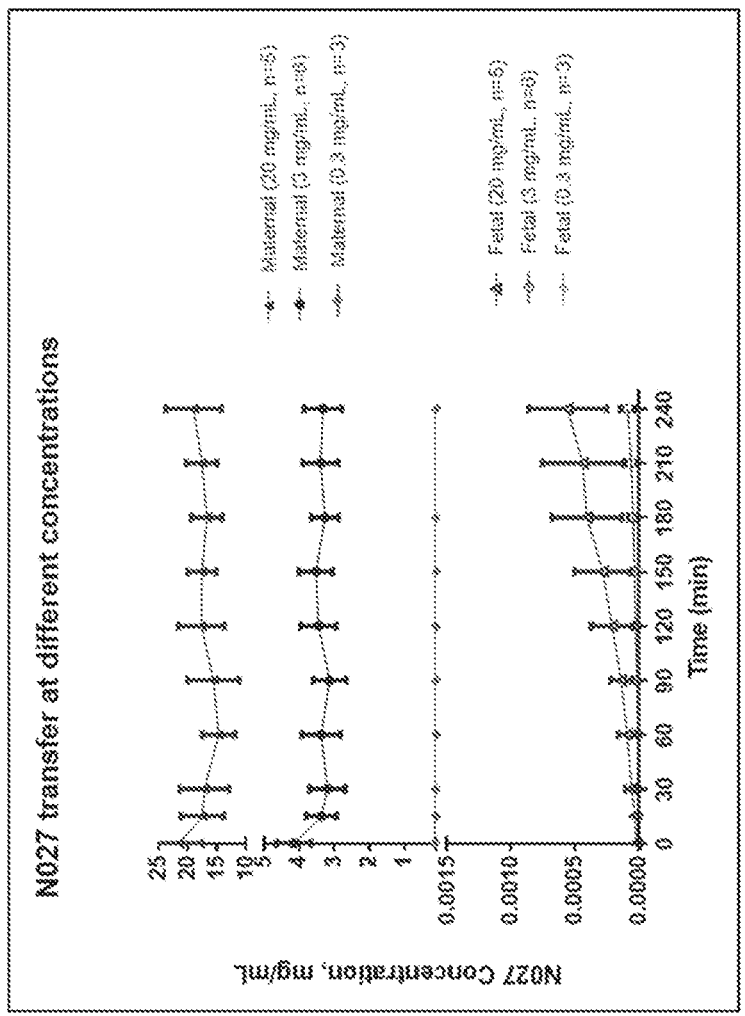
FIG. 15 is a graph that shows transplacental transfer of N027 over four hours of perfusion. The data represent N027 concentrations as mean±SD in the fetal and maternal circulation after maternal administration of the indicated concentration of N027 at t=0.

The transfer of N027 across the human placental lobule was tested for three different concentrations: 0.3 mg/ml, 3 mg/ml, and 30 mg/ml. Fourteen individual placentae were perfused for four hours with N027 being added to the maternal perfusate at 0.3 mg/ml, 3 mg/ml, and 30 mg/ml. Samples from the maternal artery and fetal vein, in 0.5 mL aliquots, were taken at 0, 15, 30, 60, 90, 120, 150, 180, 210 and 240 minutes during the experimental period. Antipyrine was employed as a positive control to validate the integrity of the circuits (FIGS. 14-15). Concentrations of N027 in maternal and fetal samples were determined using a sensitive meso scale discovery (MSD) immunoassay with a lower limit of quantification of 5 ng/ml. This assay involved a sandwich format using an anti-idiotypic antibody pair; wherein the MSD plate was coated with an anti-idiotypic Ab followed by incubation with sample and revealed with the second biotinylated anti-idiotypic Ab followed by detection with MSD tagged streptavidin and addition of read buffer. The concentration of antipyrine was determined using a HPLC assay with UV detection at 260 nm after a liquid-liquid extraction. The mean fetal transfer rate for antipyrine across fourteen experiments was 41±2.8%. The mean fetal transfer rate for N027 across fourteen experiments was 0.0027±0.0021% indicating very low levels of transfer. The results suggest that N027 could be used in methods of treating pregnant patients without causing fetal exposure.

Example 19—Pharmacokinetic and Pharmacodynamic Data for N027

A Phase 1, single-center, randomized, double-blind placebo-controlled SAD/MAD study in NHV was conducted to evaluate the safety, tolerability, PK, and PD of N027. In the SAD study, 5 cohorts received single IV infusions of placebo (n=2/cohort) or escalating doses of N027 at 0.3 (n=3), 3 (n=3), 10 (n=6), 30 (n=6), or 60 (n=6) mg/kg and were followed for safety, PK, and PD for 8 weeks (FIGS. 18 and 19).

In the MAD part of the study, subjects received up to 4 weekly IV infusions of N027 or placebo and were followed for safety. PK, and PD for 10 weeks postdose. Subjects in the first cohort received 30 mg/kg N027 or placebo. The results indicated that complete FcRn RO was achieved and maintained at 30 mg/kg (FIG. 20A). A second cohort of subjects was enrolled to receive 15 mg/kg N027 (or placebo) and it was determined complete RO was not maintained 15 mg/kg (FIG. 20B).

Figure 18:
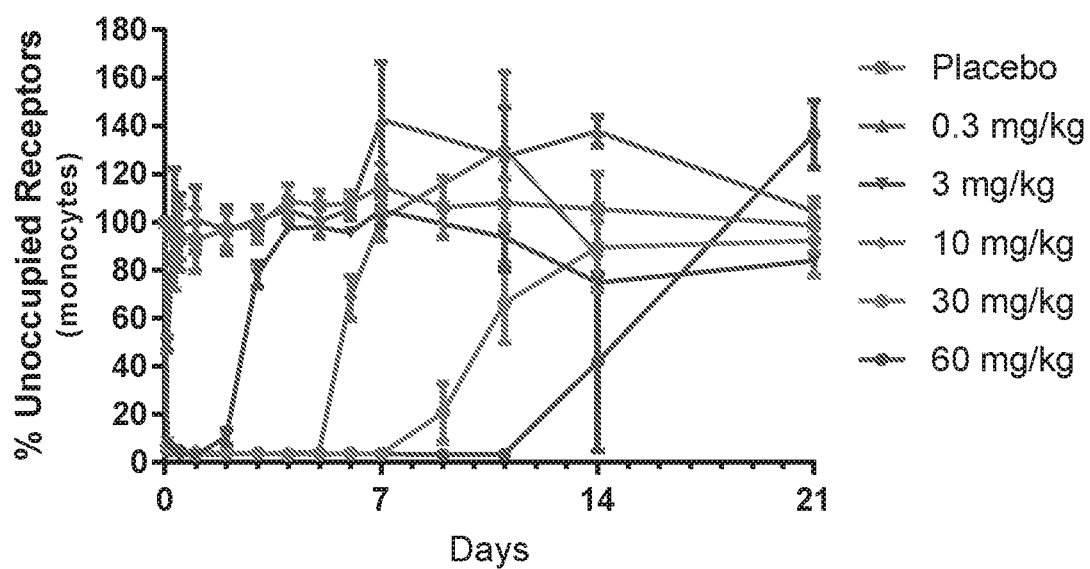
FIG. 18 is a graph showing mean (SD) FcRn receptor occupancy in circulating monocytes following single doses of 0.3, 3, 10, 30 and 60 mg/kg of N027.
Figure 19:
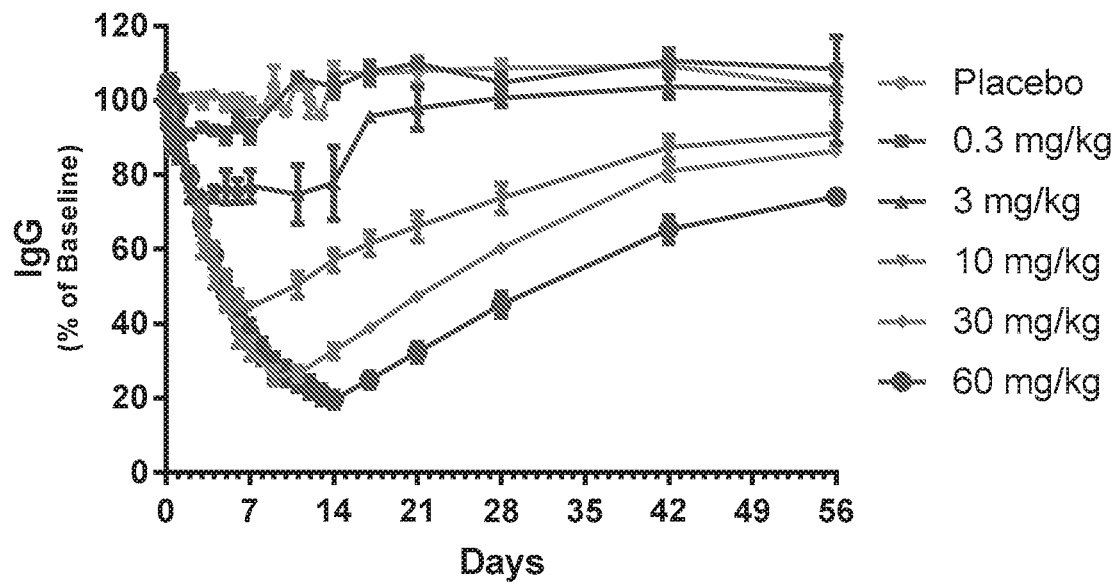
FIG. 19 is a graph showing mean (SD) serum IgG levels Following Single Doses of 0.3, 3, 10, 30 and 60 mg/kg N027.

Mean serum N027 concentration data (Day 1 Cmax and trough) for subjects in the 30 and 15 mg/kg cohorts are summarized graphically in FIG. 18. At 30 mg/kg N027, the 2-hour (Cmax) values following the first dose were within the expected range (based on SAD data) of 500-700 µg/mL and trough values on Days 7, 14, and 21 ranged from 40-140 µg/mL. With repeat dosing, group variability reduced as a steady state was established between 100-200 ug/mL. At 15 mg/kg N027, the 2-hour (Cmax) values following the first dose were between 200-400 ug/mL, and considerable variability in trough concentrations was observed, with the majority of the data falling below 10 µg/mL, providing a potential explanation for the inability to maintain complete RO was not maintained 15 mg/kg.

At both dose levels, serum IgG was suppressed was to a similar degree during the period of dosing (FIGS. 21A and 21B).

Both the 15 mg/kg dose and the 30 mg/kg dose were safe and well-tolerated in this Phase I study.

Example 20—Impact of M281 (N027) and IVIg on Placental Transfer of a IgG1 Monoclonal Antibody In this example, the average maternal to fetal transfer of a representative IgG1 monoclonal antibody, Humira®, known to transfer across the placenta was studied, and the potential of M281 (i.e., M281), to inhibit this transplacental transfer of Humira® was evaluated. The effect of M281 on the transfer of IgG was evaluated at concentrations selected to range across active serum concentrations expected at therapeutic doses ranging from 10 µg/ml, which is near the threshold for increased M281 clearance due to target-mediated disposition and related in M281 pharmacokinetics to the timeframe when the loss of full occupancy of FcRn receptors occurs; to 3000 µg/ml, concentration which is 2 to 3-fold above the Cmax at 60 mg/kg M281, the highest dose evaluated in the first in human healthy volunteer study. Furthermore, this blockade of IgG transfer was also assessed using a positive control IVIg (polyclonal IgG mixture), which is a known competitive inhibitor of FcRn for IgG transfer.

Placental Perfusion

Placentas from normal healthy term (38-40 weeks) pregnancies were collected immediately following Cesarean-sectioned abdominal deliveries according to the approved study protocol. Placentas with any evidence of maternal infection, systemic disease, and drug or alcohol abuse during pregnancy were excluded from this study.

The technique of Dual Perfusion of human Placental Lobule (DPPL) was used according to established protocol as described (Nanovskaya T, Deshmukh S, Brooks M, Ahmed M S. Transplacental transfer and metabolism of buprenorphine. J *Pharmacol Exp Ther.* 2002; 300(1):26-33). Briefly, each placenta was examined for tears, and 2 chorionic vessels (one artery and vein) supplying a single intact peripheral cotyledon were cannulated with 3F and 5F umbilical catheters, respectively. The cotyledon was trimmed and placed in the perfusion chamber with the maternal surface upward. The intervillous space on the maternal side was perfused by 2 catheters piercing the basal plate. A large venous drain was connected to a peristaltic pump, which continuously removed the fluid from the chamber and either returned it to the maternal reservoir (closed circuit) or to a separate container (open circuit). The flow rate of the perfusate medium in the fetal and maternal circuits was 3.0 and 12 mL/min, respectively. The maternal perfusate was equilibrated with a gas mixture made of 95% $O_2$, 5% $CO_2$, and the fetal perfusate with a mixture of 95% $N_2$, 5% $CO_2$. All experiments were carried out at a temperature of 37° C.

Each placental lobule was perfused for an initial control period of one hour to allow the tissue to stabilize to its new environment using open-open configuration of perfusion system. Perfusion was terminated if one of the following quality criteria was not met during the control period: i) volume loss in fetal circuit in excess of 3 mL/h; or ii) $O_2$ pressure difference between fetal vein and artery less than 60 mmHg, indicating inadequate perfusion overlap between the two circuits.

At the end of the control period 10 ml outflow from maternal and 10 ml outflow from fetal vein were collected to determine baseline levels of endogenous IgG. On termination of the control period, the perfusion system was converted to a closed-closed configuration (re-circulation of the medium). The media was replaced in both the maternal and fetal reservoirs followed by addition of 3 mg/ml of BSA in both reservoirs. The test substance (Humira® or Humira®+M281 or Humira®+IVIg or Humira®+IVIg+M281) was then added to the maternal reservoir, and the experimental period initiated after an aliquot (1 mL) was withdrawn and stored as T=0. The test substance was co-transfused with a positive control, antipyrine (AP) at 100 µg/ml. Samples from the maternal artery and fetal vein, in 0.5 mL aliquots, were taken at 0, 30, 60, 120, 180, 240, 270, 300, 330 and 360 minutes during experimental period. At the end of experiment, the perfused area was dissected from the adjoining placental tissue, weighed and pieces of perfused lobule were placed in 4% PFA for IHC analysis.

Humira® concentrations in all the maternal and fetal sample aliquots were determined using the sandwich ELISA with a lower limit of quantitation (LLOQ) of ~1 ng/ml. The transfer of Humira® from maternal to fetal reservoir was determined by the fetal transfer rate (FTR) which was calculated as below:

$$\text{FTR for Humira} = \frac{\text{Conc. of Humira in the fetal perfusate at end of experiment}}{\text{Conc. of Humira in the maternal perfusate at start of experiment } (t=0)} \times 100$$

M281 concentrations in all the maternal and fetal sample aliquots were determined. The transfer of M281 from maternal to fetal reservoir was determined by the fetal transfer rate (FTR) which was calculated as below:

$$\text{FTR for } M281 = \frac{\text{Conc. of } M281 \text{ in the fetal perfusate at end of experiment}}{\text{Conc. of } M281 \text{ in the maternal perfusate at start of experiment } (t=0)} \times 100$$

TABLE 11

Composition of the maternal and fetal compartments

| Maternal Circuit Perfusion Media | Fetal Circuit Perfusion Media |
|---|---|
| 150 mL M199 media | 90 mL M199 media |
| 7.5 g/L Dextran 40 | 30 g/L Dextran 40 |
| 40 mg/L Gentamicin Sulfate | 40 mg/L Gentamicin Sulfate |
| Sulfamethoxazole (80 mg/L)/ | Sulfamethoxazole (80 mg/L)/ |
| Trimethoprim (16 mg/L) | Trimethoprim (16 mg/L) |
| 25 IU/ml Heparin | 25 IU/ml Heparin |
| 7.5% Sodium bicarbonate to pH 7.4 | 7.5% Na bicarbonate to pH 7.35 |
| 3 mg/ml Bovine Serum Albumin | 3 mg/ml Bovine Serum Albumin |
| 100 µg/mL Antipyrine | |

Antipyrine Analysis

Antipyrine (AP) is a small molecule (188 Da), non-ionizable at pH 7.4 (pKa 1.4) and consequently transfers freely across the placenta via passive diffusion. Furthermore, AP is preferentially distributed into the aqueous maternal and fetal circuits with minimal retention in the tissue due to its low octanol/water partition coefficient, 0.33, as well as its minimal binding to plasma proteins and serum albumin. It has been extensively used in perfusion models as an internal permeability positive control to account for interplacental variations across different experiments.

Antipyrine concentrations were measured in samples using a modified HPLC method as described in previous reports (Merck T. J., Sorda G., Bechi N., Rasmussen B. S., Nielsen J. B., Ietta F., Rytting E., Mathiesen L., Paulesu L, Knudsen L. E. Placental transport and in vitro effects of Bisphenol A. Reproductive Toxicol. 2010; 30: 131-137). The transfer of antipyrine from maternal to fetal reservoir was determined by the fetal transfer rate (FTR) which was calculated as below:

$$\text{FTR for } AP = \frac{\text{Conc. of } AP \text{ in the fetal perfusate at end of experiment}}{\text{Conc. of } AP \text{ in the maternal perfusate at start of experiment } (t=0)} \times 100$$

A FTR of antipyrine between 35-45% considered as high degree of perfusion overlap was used to validate and compare each experiment. Furthermore, fetal to maternal (FTM) ratios for the transfer of AP was calculated at each time point to ascertain equilibrium between the maternal and fetal side. The FTM ratio was ideally expected to be greater than 0.75 around 60-120 min; thus confirming placental integrity.

Briefly, the protein was precipitated by 200 μl ice-cold acetonitrile containing 10 μl/ml of internal standard phenacetin to each 200 μl sample. The samples were centrifuged for 25 min at 8000 rpm, and the supernatants were analyzed by HPLC. Briefly, Antipyrine and phenacetin were analyzed using an Agilent 1200 HPLC system equipped with a UV detector. The stationary phase used was a reverse phase C18 based column (Waters Atlantis T3, Atlantis T3 Column, 100 Å, 3 μm, 3 mm×150 mm). The column was also equipped with a guard cartridge (Waters T3, 3 μm, 2.1 mm×150 mm) which was changed prior to start of each samples set. The column and sample temperatures were maintained at 25° C. and 4° C. respectively. The samples were run with a linear gradient ranging from 25-95% Methanol-Water over 14 min at a flow rate of 0.3 mL/min; the injection volume was 10 μL and detection was carried out using absorbance at 260 nm.

Transfer of Humira®

Placental transfer of Humira® was studied at a fixed concentration of 270 μg/ml. A total of 8 experiments which maintained the placental integrity over experiment duration and met the quality criteria for successful perfusions such as antipyrine FTM ratio above 0.75 and volume loss from fetal reservoir no more than 3 ml/h; are reported in Table 12. Oxygen transfer levels and consumption were also monitored for these experiments as markers for perfusion overlap and tissue viability, respectively.

TABLE 12

Placental Transfer of Humira ®

| Exp. ID | Test Article | Run Time (h) | Wt. of cotyledon (g) | Antipyrine FTR[1] (%)[2] | Humira ® FTR[1] (%) |
|---|---|---|---|---|---|
| 39 | Humira ® | 6 | 38.7 | 41.6 | 0.65 |
| 41 | Humira ® | 6 | 34.3 | 39.3 | 0.11 |
| 45 | Humira ® | 6 | 32.3 | 39.9 | 0.22 |
| 60 | Humira ® | 6 | 29.5 | 42.0 | 0.42 |
| 72 | Humira ® | 6 | 37.5 | 39.8 | 0.21 |
| 73 | Humira ® | 6 | 39.7 | 39.6 | 0.03 |
| 74 | Humira ® | 6 | 32.7 | 47.2 | 0.05 |
| 80 | Humira ® | 6 | 28.1 | 43.9 | 0.15 |

[1]Ratio of fetal to maternal perfusate concentration x 100%
[2]Antipyrine transfer range between 35-45%

Figure 22:
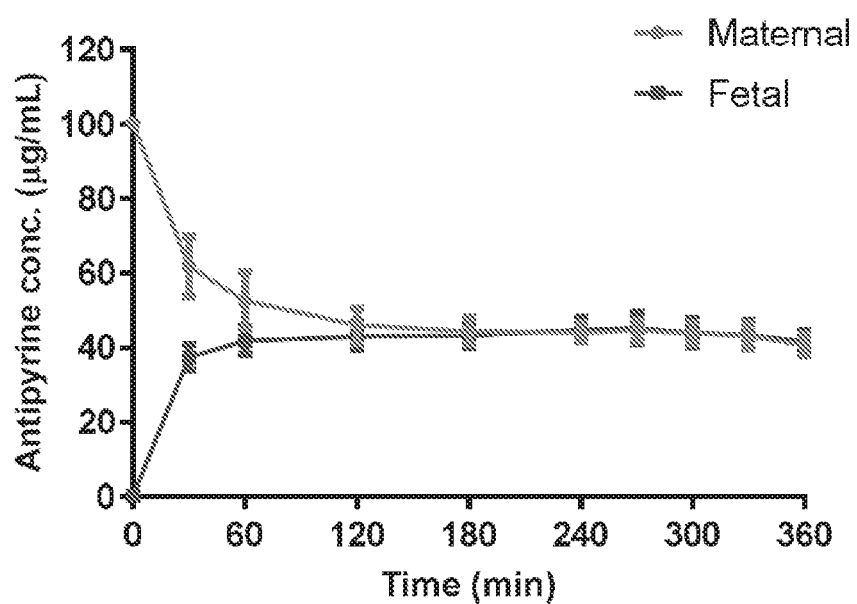
FIG. 22 is a graph showing transplacental transfer of antipyrine (Humira® in the maternal reservoir; n=8). Data represents antipyrine concentrations as Mean±SD in the fetal (filled squares) and maternal (filled circles) circulation after maternal administration of 100 µg/ml antipyrine at t=0.

Placental transfer of antipyrine over the course of these experiments is shown in FIG. 22 and the fetal to maternal (FTM) concentration ratio was calculated for each experiment at each time point as well as terminal endpoint. All experiments were observed to attain equilibrium (FTM ratio of 0.9-1.0) within 60-180 min; and the mean±SD fetal to maternal FTM ratio at the terminal end point over 8 experiments was calculated to be 1.03±0.11; indicating appropriate placental integrity over experiment duration. The maternal to fetal transfer levels of antipyrine were observed to >35% in all experiments, indicating a high degree of perfusion overlap for the reported experiments.

Figure 23:
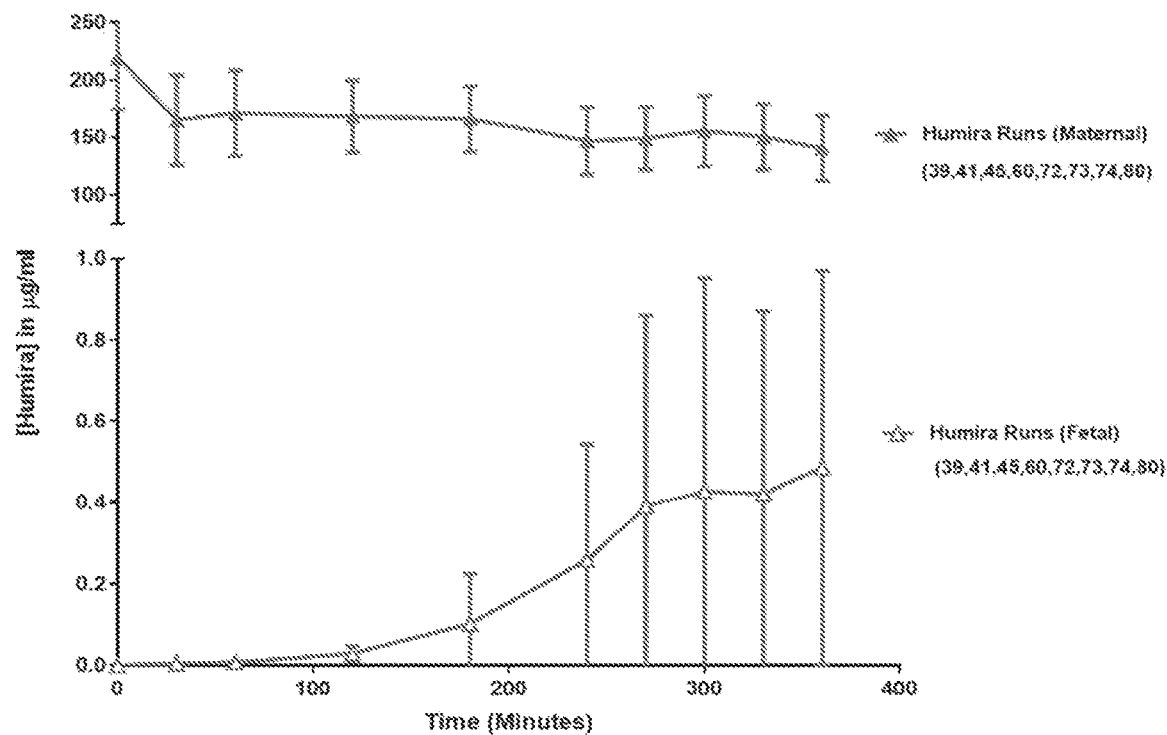
FIG. 23 is a graph showing placental transfer of Humira® over 6 hours of perfusion (n=8). The data represents Humira® concentrations as Mean±SD in the fetal and maternal circulation after maternal administration of 270 µg/ml Humira® at t=0.

Placental transfer of Humira® over eight experiments is shown in FIG. 23. As shown in Table 12, the mean±SD fetal transfer rate was calculated to average around 0.23±0.21% while the average mean±SD fetal concentration at the end of experiment ranged between 0.49±0.49 μg/mL.

Transfer of Humira® in the Presence of M281

Placental transfer of Humira® in the presence of M281 was studied keeping the Humira® concentration constant at 270 μg/ml but varying the concentration of M281 in the maternal reservoir. All experiments maintained the placental integrity over experiment duration and met the quality criteria for successful perfusions such as antipyrine fetal to maternal (FTM) ratio above 0.75 and volume loss from fetal reservoir no more than 3 ml/h. A summary of studies and results is shown in Table 13. Oxygen transfer levels were also monitored for these experiments as markers for tissue viability, as previously mentioned (Note: Experiment PP 75 was carried out in the absence of antipyrine but other parameters such as fetal volumes and oxygen transfer were measured and were in accordance with the quality criteria for good perfusions).

TABLE 13

Placental Transfer of Humira ® in the presence of M281

| Exp. ID | Test Article | [M281] (μg/mL) | Run Time (h) | Wt. of cotyledon (g) | Antipyrine FTR[1] (%) | M281 FTR[1] (%) | Humira ® FTR[1] (%) |
|---|---|---|---|---|---|---|---|
| 46 | Humira ® | 3000 | 6 | 24.8 | 39.7 | 0.001 | 0.06 |
| 48 | Humira ® | 300 | 6 | 30.3 | 45.8 | 0.002 | 0.08 |
| 70 | Humira ® | 300 | 6 | 38.0 | 39.1 | 0.003 | 0.05 |
| 71 | Humira ® | 300 | 6 | 28.1 | 42.7 | 0.003 | 0.05 |
| 75 | Humira ® | 300 | 6 | 35.3 | — | 0.021 | 0.07 |
| 76 | Humira ® | 300 | 6 | 30.8 | 43.9 | 0.001 | 0.07 |
| 77 | Humira ® | 10 | 6 | 26.5 | 41.8 | 0.000 | 0.06 |
| 78 | Humira ® | 10 | 6 | 29.5 | 52.3 | 0.000 | 0.08 |
| 79 | Humira ® | 10 | 6 | 41.2 | 44.8 | 0.000 | 0.07 |

[1]Ratio of fetal to maternal perfusate concentration x 100%

Figure 24:
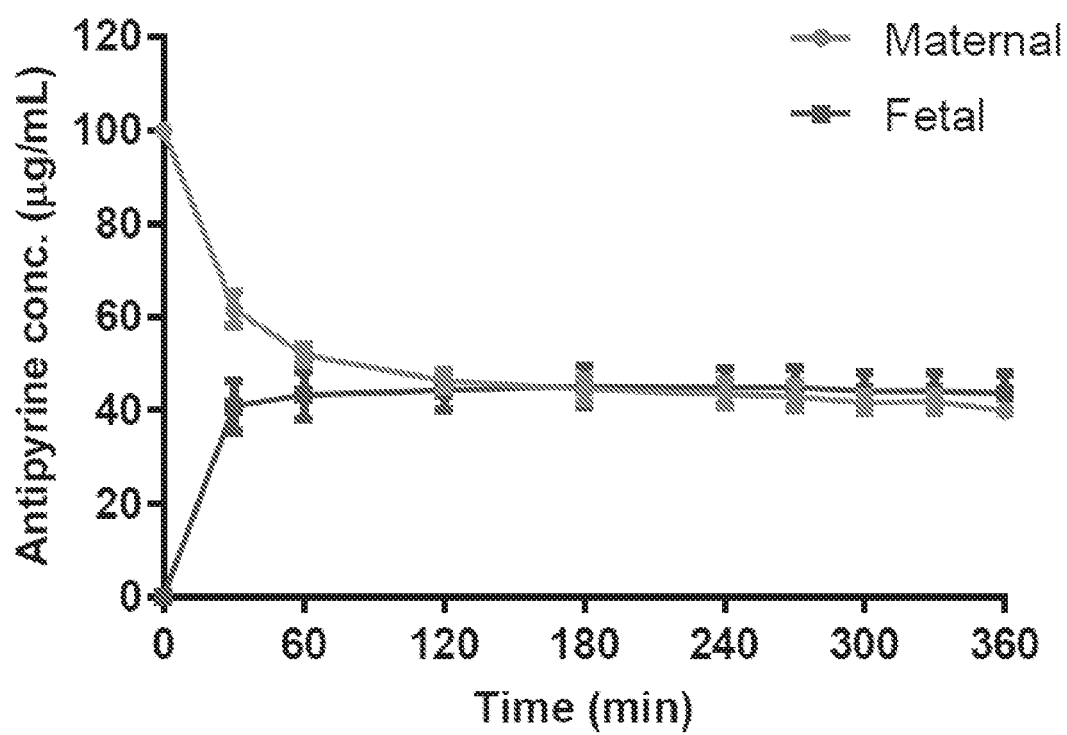
FIG. 24 is a graph showing transplacental transfer of antipyrine (Humira®+N027 in the maternal reservoir; n=9). The data represents antipyrine concentrations as Mean±SD in the fetal (filled squares) and maternal (filled circles) circulation after maternal administration of 100 µg/ml antipyrine at t=0.

Placental transfer of antipyrine over the course of these experiments is shown in FIG. 24 and the fetal to maternal (FTM) transfer ratio was calculated for each experiment at each of the time points as well as the terminal end point. The mean±SD FTM ratio at the terminal end point over 8 experiments with antipyrine was calculated to be 1.1±0.11 (equilibrium attained in maternal and fetal circuits) indicating appropriate placental integrity over experiment duration. The maternal to fetal transfer levels of antipyrine were observed to >35%, indicating a high degree of perfusion overlap for the reported experiments.

Figure 25:
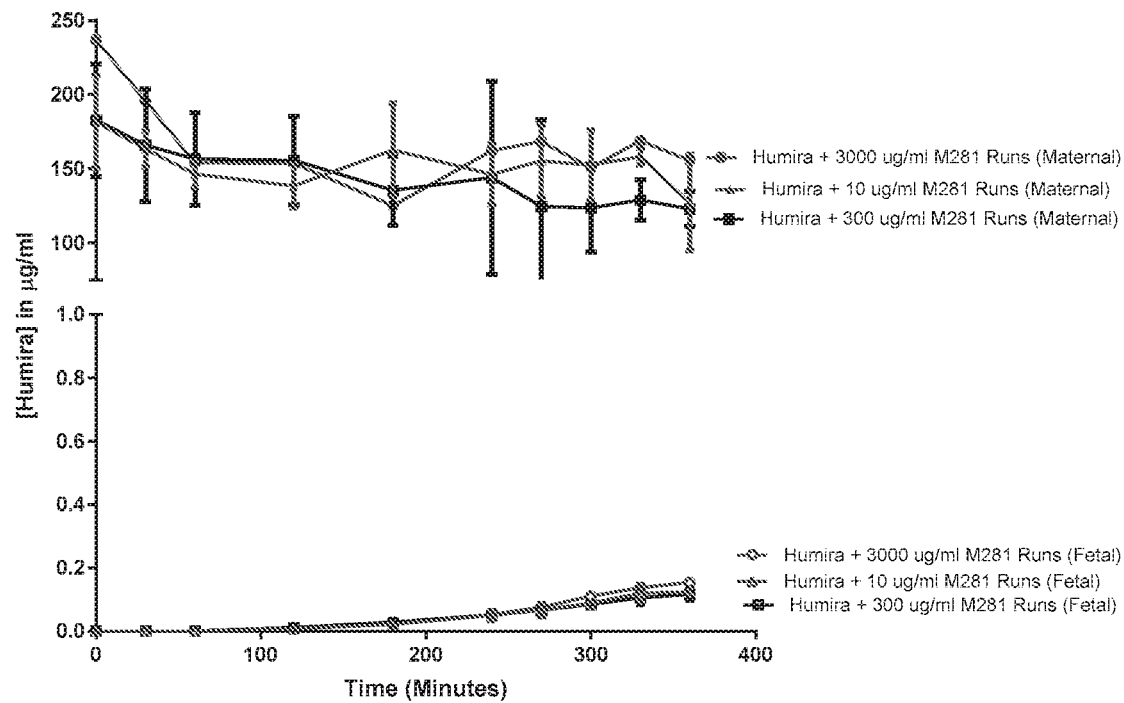
FIG. 25 is a graph showing placental transfer of Humira® in the presence of varying concentrations of N027. The data represents Humira® concentrations as Mean±SD in the fetal and maternal circulation after maternal administration of 270 µg/ml Humira®+N027 at t=0.

Placental transfer of Humira® in the presence of M281 over nine experiments is shown in FIG. 25. The fetal transfer rate (mean±SD) for Humira® in the presence of 300 μg/ml M281 was calculated to be 0.06±0.01% (n=5) while the experiments with Humira® in the presence of 10 μg/mL M281 (n=3) exhibited a mean fetal transfer rate of 0.07±0.01% (mean±SD). Similarly, the fetal transfer rate for Humira® in the presence of 3000 μg/ml M281 was 0.06 (n=1). Taken collectively, the fetal transfer rate of Humira® over all 9 experiments reported in Table 13 was calculated to average around 0.07±0.01% while the average terminal fetal concentrations ranged between 0.12±0.02 μg/mL.

The collective mean fetal transfer rate of M281 over 9 experiments was calculated to be 0.003±0.007%. As reported in Table 13, for experiments PP77-79, the levels of M281 in the fetal side were below the limit of detection while the average fetal transfer rate for the experiments with 300 μg/ml M281 (n=5) was calculated to be 0.006±0.009%. These observed minimal transplacental transfer rates of M281 are consistent with previous experiments (data not shown).

Transfer of Humira® in the Presence of IVIg

Placental transfer of Humira® (maternal concentration kept constant at 270 μg/ml) was studied in the presence of IVIg (6.7 mg/ml) over 5 experiments. All experiments maintained the placental integrity over experiment duration and met the quality criteria for successful perfusions such as antipyrine FTM ratio above 0.75 and volume loss from fetal reservoir no more than 3 ml/h. Oxygen transfer levels were also monitored for these experiments as markers for tissue viability, as previously described. A summary of studies and results is shown in

TABLE 14

Placental Transfer of Humira ® in the presence of IVIg

| Exp. ID | Test Article | [IVIg] (mg/mL) | Run Time (h) | Wt. of cotyledon (g) | Antipyrine FTR[1] (%) | Humira ® FTR[1] (%) |
|---|---|---|---|---|---|---|
| 34 | Humira ® | 6.7 | 6 | 27 | 48.2 | 0.11 |
| 38 | Humira ® | 6.7 | 5.5 | 31 | 40.4 | 0.06 |
| 52 | Humira ® | 6.7 | 6 | 16.5 | 48.4 | 0.07 |
| 54 | Humira ® | 6.7 | 6 | 25.2 | 34.9 | 0.06 |
| 55 | Humira ® | 6.7 | 6 | 15 | 41.6 | 0.03 |

[1]Ratio of fetal to maternal perfusate concentration × 100%

Figure 26:
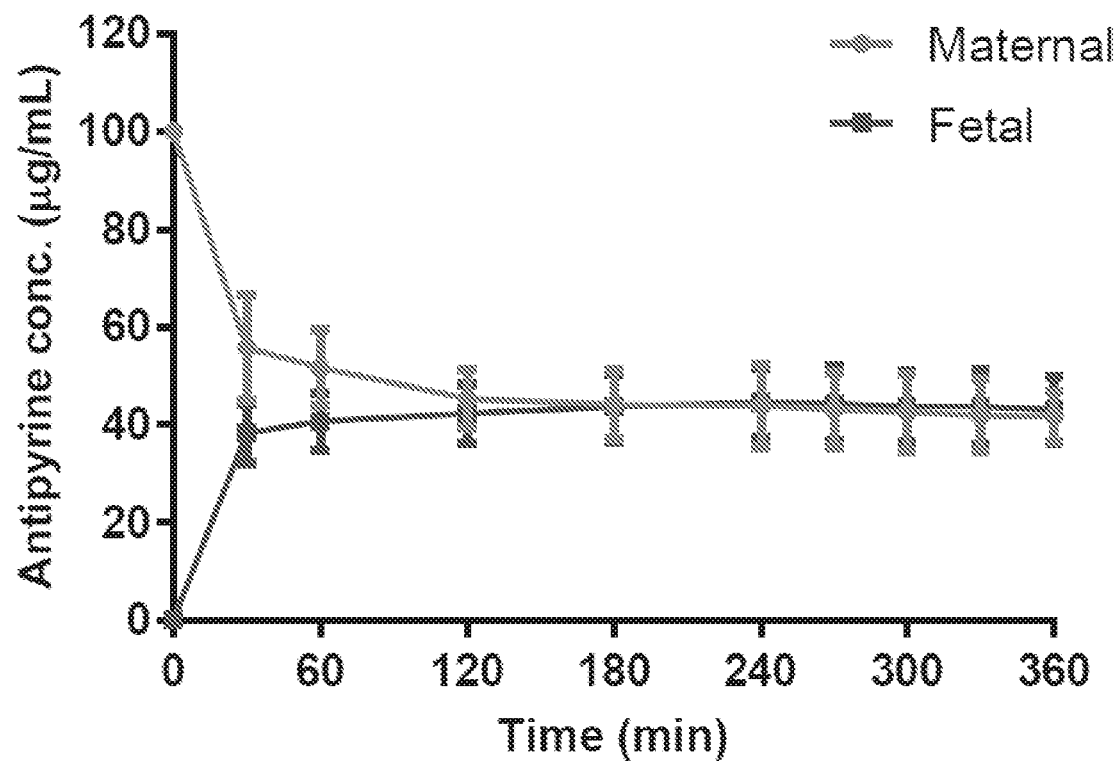
FIG. 26 is a graph showing Transplacental transfer of antipyrine (Humira®+IVIg in the maternal reservoir; n=5). The data represents antipyrine concentrations as Mean±SD in the fetal (filled squares) and maternal (filled circles) circulation after maternal administration of 100 µg/ml antipyrine at t=0.

Placental transfer of antipyrine over the course of these experiments is shown in FIG. 26 and the FTR was calculated for each experiment at the terminal end point. It is to be noted that PP38 was terminated at 5.5 hrs and hence the FTR was calculated after 5.5 hours as compared to 6h for the other experiments. The mean±SD fetal to maternal (FTM) concentration ratio at the terminal end point over 5 experiments was calculated to be 1.04±0.04 (equilibrium attained in maternal and fetal circuits) indicating appropriate placental integrity over experiment duration. The maternal to fetal transfer levels of antipyrine were observed to 35%, indicating a high degree of perfusion overlap for the reported experiments.

Figure 27:
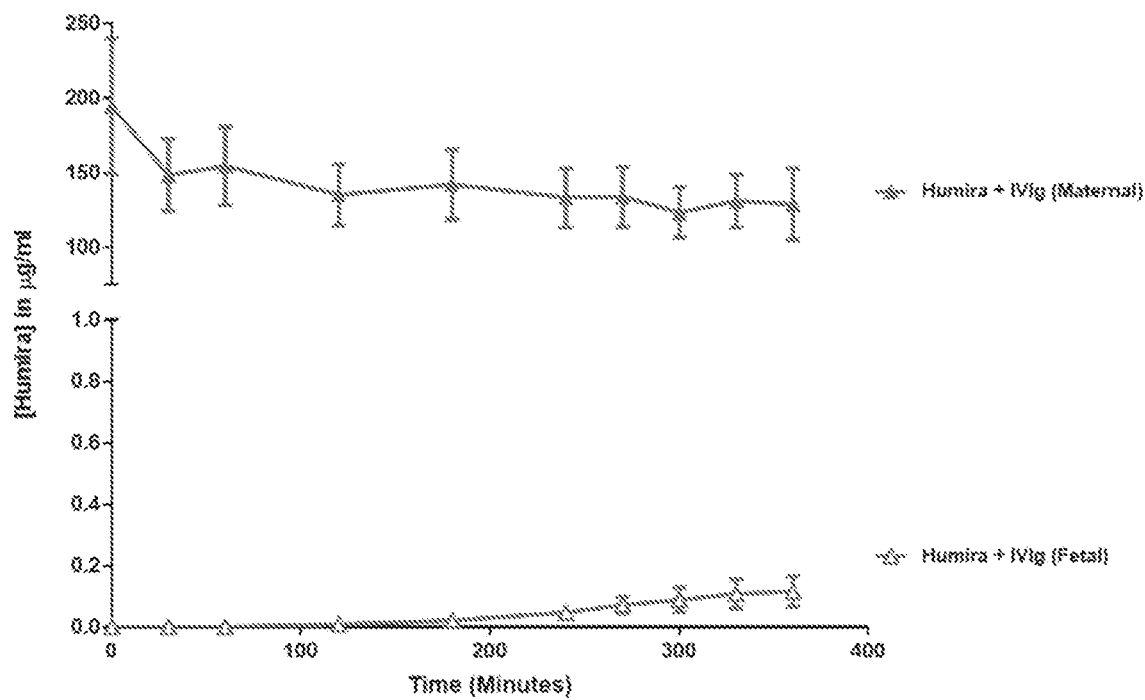
FIG. 27 is a graph showing placental transfer of Humira® in the presence of IVIg. The data represents Humira® concentrations as Mean±SD in the fetal (filled squares) and maternal (filled circles) circulation after maternal administration of 270 µg/ml Humira®+N027 at t=0.

Placental transfer of Humira® in the presence of IVIg over five experiments is shown in FIG. 27. The fetal transfer rate of Humira® in the presence of IVIg was calculated to average around 0.07±0.03% (n=5) while the average terminal fetal concentrations of Humira® ranged between 0.12±0.06 µg/ml.

Transfer of Humira® in the Presence of IVIg+M281

Placental transfer of Humira® in the presence of IVIg+M281 was studied over 4 experiments keeping the Humira® concentration at 270 µg/ml, IVIg at 6.7 mg/mL and M281 at 300 µg/mL in the maternal reservoir. All experiments maintained placental integrity over experiment duration and met the quality criteria for successful perfusions such as antipyrine fetal to maternal (FTM) ratio above 0.75 and volume loss from fetal reservoir no more than 3 ml/h. A summary of the experiments is shown in Table 15. Oxygen transfer levels were also monitored for these experiments as markers for tissue viability, as previously mentioned.

TABLE 15

Placental Transfer of Humira ® in the presence of IVIg + M281

| Exp. ID | Test Article | IVIg (mg/mL) | [M281] (µg/mL) | Run Time (h) | Wt. of cotyledon (g) | Antipyrine FTR[1] (%) | Humira ® FTR[1] (%) |
|---|---|---|---|---|---|---|---|
| 49 | Humira ® | 6.7 | 300 | 6 | 19.9 | 48.1 | 0.02 |
| 50 | Humira ® | 6.7 | 300 | 6 | 22.5 | 40.5 | 0.01 |
| 53 | Humira ® | 6.7 | 300 | 6 | 31.4 | 40.6 | 0.11 |
| 56 | Humira ® | 6.7 | 300 | 6 | 30.5 | 40.4 | 0.01 |

[1]Ratio of fetal to maternal perfusate concentration × 100%

Figure 28:
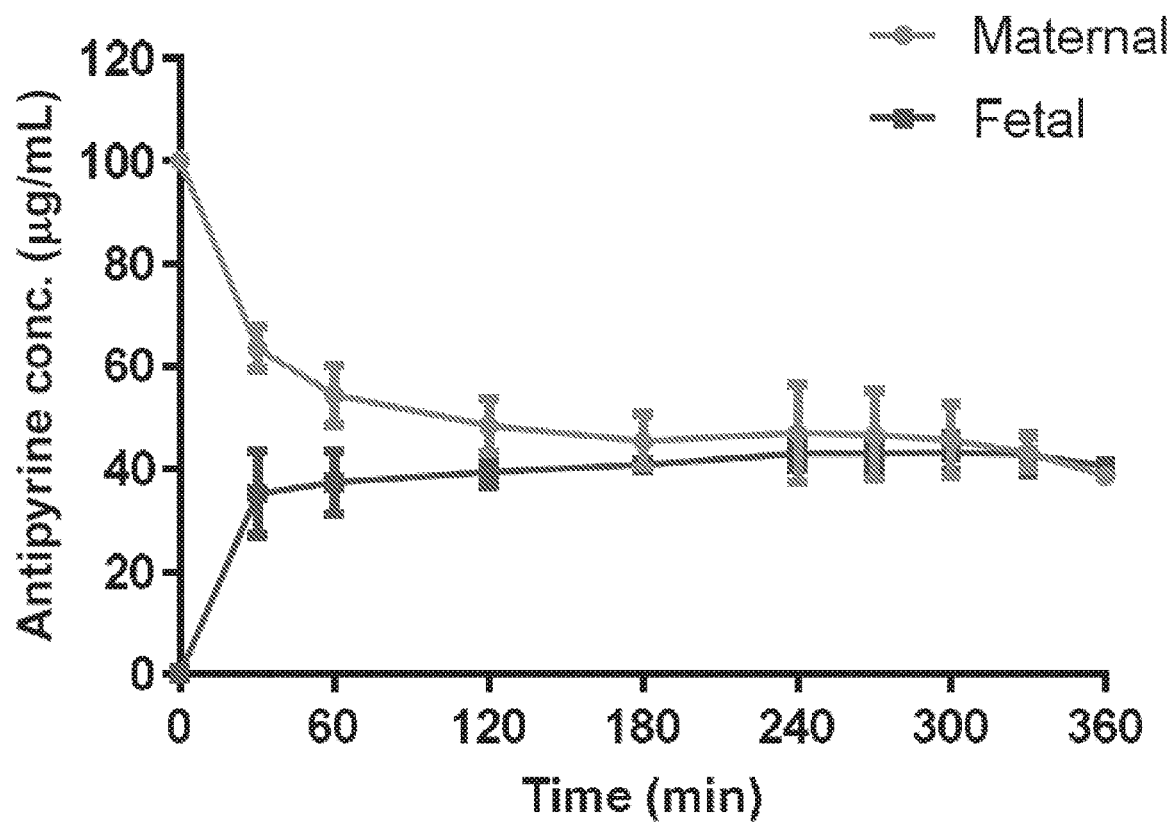
FIG. 28 is a graph showing transplacental transfer of antipyrine (Humira®+IVIg+N027 in the maternal reservoir; n=4). Data represents antipyrine concentrations as Mean±SD in the fetal (filled squares) and maternal (filled circles) circulation after maternal administration of 100 µg/ml antipyrine at t=0.

Placental transfer of antipyrine for the experiments is shown in FIG. 28 and the FTM was calculated for each experiment at the all the individual time points as well as at terminal end point. The mean±SD FTM for antipyrine over 4 experiments shown in Table 15 was calculated to be 1.04±0.03 (equilibrium attained in maternal and fetal circuits) indicating appropriate placental integrity over experiment duration. The maternal to fetal transfer levels of antipyrine were observed to be >35%, indicating a high degree of perfusion overlap for the reported experiments.

Figure 29:
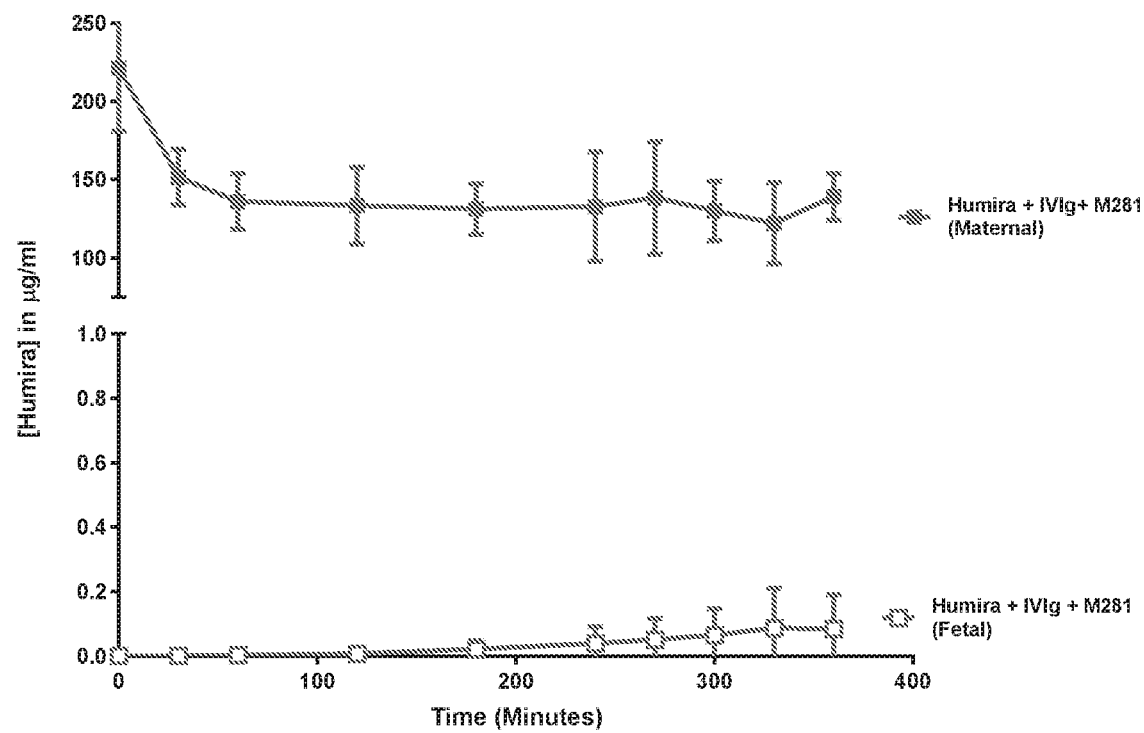
FIG. 29 is a graph showing placental transfer of Humira® in the presence of IVIg+N027. Data represents Humira® concentrations as Mean±SD in the fetal (filled squares) and maternal (filled circles) circulation after maternal administration of 270 µg/ml Humira®+IVIg+N027 at t=0.

Placental transfer of Humira® in the presence of IVIg and M281 over four experiments is shown in FIG. 29. As shown in Table 15, the fetal transfer rate was calculated to average around 0.04±0.05% (n=4) while the average terminal fetal concentrations ranged between 0.07±0.09 µg/mL. M281 transfer was not measured in this series of experiments.

Statistical Analyses

All the experimental data were subjected to statistical analyses. A linear mixed effects (LME) model was used for analysis of all of the experimental data with random terms for both slope and intercept for each donor ID to account for the correlation among measurements from the same donor/PP experiment. All fetal concentrations were divided by the maternal concentration at corresponding time points and then log transformed. The sensitivity of the results to possible outliers was also assessed and determined to be robust. P-values were adjusted for multiple comparisons.

TABLE 16

Summary of transplacental transfer of Humira ® in the presence/absence of M281/IVIg

| Exp. ID/ PP# | Test Article | M281 Conc. (µg/mL) | Average Antipyrine FTR[1] (%) | Average M281 FTR[1] (%) | Average Humira ® FTR[1] (%) | P value* as compared to Humira ® |
|---|---|---|---|---|---|---|
| 39, 41, 45, 60, 72, 73, 74, 80 | Humira ® | — | 41.7 ± 2.7 | NA | 0.23 ± 0.21 | NA |
| 46 | Humira ® + M281 | 3000 | 43.8 ± 4.2 | 0.003 ± 0.007 | 0.06 | NA |
| 48, 70, 71, 75, 76 | Humira ® + M281 | 300 | | | 0.06 ± 0.01 | <0.001 |
| 77, 78, 79 | Humira ® + M281 | 10 | | | 0.07 ± 0.01 | <0.001 |

TABLE 16-continued

Summary of transplacental transfer of Humira ® in the presence/absence of M281/IVIg

| Exp. ID/ PP# | Test Article | M281 Conc. (μg/mL) | Average Antipyrine FTR[1] (%) | Average M281 FTR[1] (%) | Average Humira ® FTR[1] (%) | P value* as compared to Humira ® |
|---|---|---|---|---|---|---|
| 34, 38, 52, 54, 55 | Humira ® + IVIg | — | 42.5 ± 6.1 | NA | 0.07 ± 0.03 | <0.001 |
| 49, 50, 53, 56 | Humira ® + IVIg + M281 | 300 | 42.4 ± 3.8 | ND | 0.04 ± 0.05 | <0.001 |

ND: Not determined
NA: Not applicable
*Calculated using a linear mixed effects model with random slope and intercept Example 21—Impact of M281 (N027) on Albumin Levels Administration of M281 (N027) was associated with a reduction in serum albumin levels in subjects. For example, a reduction to a maximum of about 20-25% below baseline was observed with a single 60 mg/kg dose and when multiple weekly 15 and 30 mg/kg doses were administered. The hypoalbuminemia was asymptomatic. It was not associated with proteinuria, edema or other adverse events.

Figure 30:
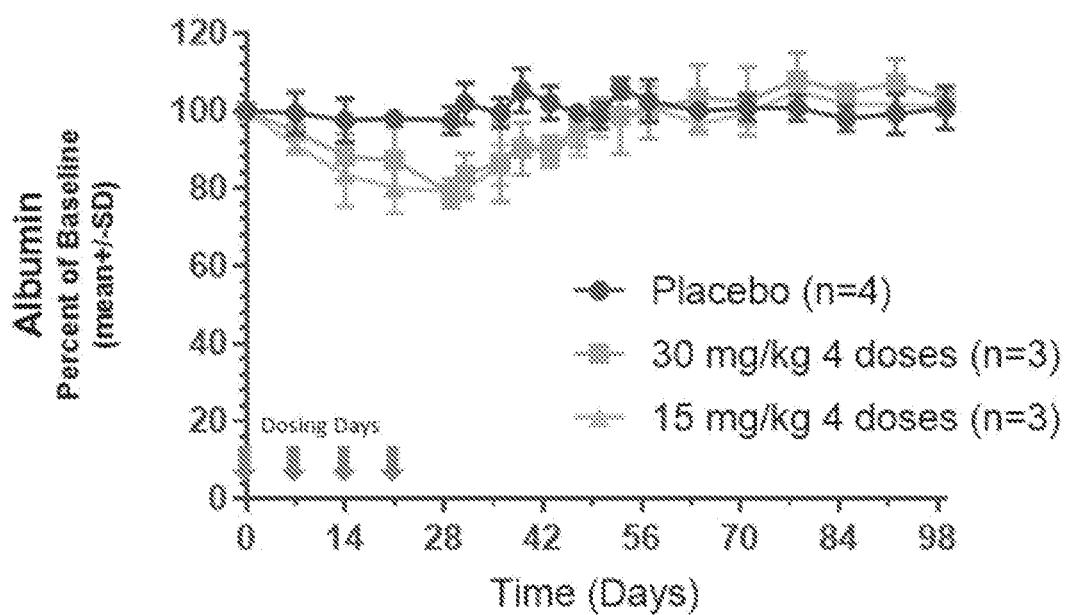
FIG. 30 is a graph showing impact on serum albumin in subjects treated with 3 doses of N027 at 15 mg/kg or 30 mg/kg.
Figure 31:
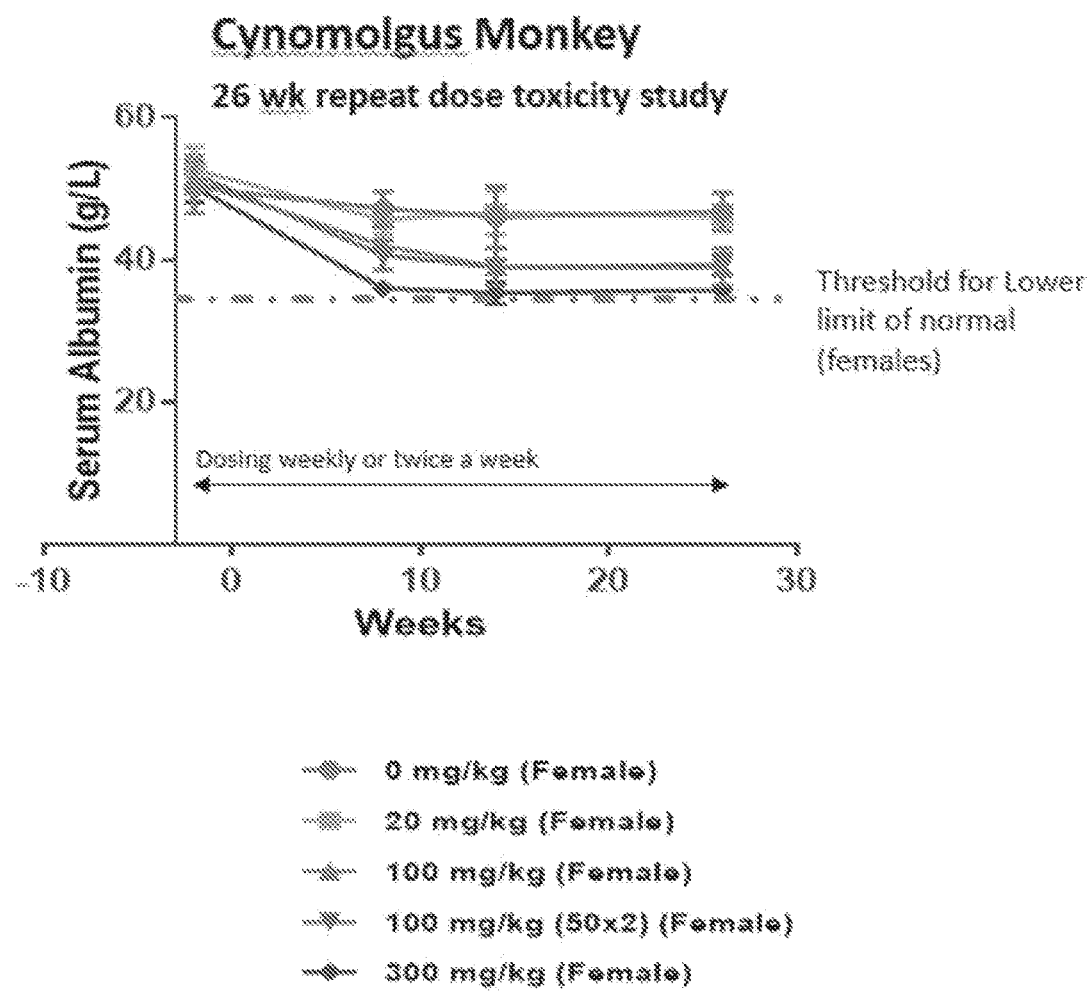
FIG. 31 is a graph showing impact on serum albumin in cynomolgus monkeys treated with N027 in a 26 week repeat dose toxicity study.

The results of analysis of the impact of M281 on albumin are presented in FIGS. 30-32. All subjects dosed with a single dose at 60 mg/kg of M281 had a decrease in serum albumin to below the normal range (normal range=34-50 g/L), and albumin levels recovered within one week of reaching their nadir. The mean nadir was 23±9% below baseline (range 8.6-33%) at approximately day 14. Recovery to baseline occurred with 3 to 4 weeks of nadir and began at the time when FcRn receptor occupancy was lost. Albumin levels in subjects treated at 15 or 30 mg/kg weekly reached a mean nadir 21-25% below baseline. Recovery to baseline occurred within 3 to 4 weeks of nadir. In general, lower baseline albumin levels were associated with a greater degree of hypoalbuminemia. Subjects treated with placebo or a lower dose of M281 exhibited similar immediate declines in albumin of about 10%, recovering after 7 days. Reductions in albumin greater than that observed with placebo was observed at M281 single doses of 30 mg/kg or greater.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent or patent application was specifically and individually indicated to be incorporated by reference in its entirety.

Other embodiments are within the following claims.

What is claimed is:

1. A method for treating or reducing the risk of developing a fetal and neonatal alloimmune and/or autoimmune disorder comprising administering to a pregnant woman a composition comprising an antibody comprising a light chain having the amino acid sequence of SEQ ID NO:19 and a heavy chain having the amino acid sequence of SEQ ID NO:24, wherein the composition is administered to the pregnant woman from about gestational week 13 to about gestational week 35.

2. The method of claim 1, wherein the antibody is administered at a dose per administration and is based on the weight of the pregnant woman at first dosing and is not adjusted upward based on weight gain by the pregnant woman.

3. The method of claim 1, wherein the antibody is administered at a dose per administration and is based on the weight of the pregnant woman at first dosing and is adjusted upward based on weight gain by the pregnant woman.

4. The method of claim 1, wherein the composition is administered at least every other week.

5. The method of claim 1, wherein the composition is administered every other week.

6. The method of claim 1, wherein the composition is administered at least every week.

7. The method of claim 1, wherein IVIG is administered to the pregnant woman after cessation of administration of the antibody and prior to birth.

8. The method of claim 7, wherein IVIG is administered to the pregnant woman 40-100 hrs prior to birth.

9. The method of claim 7, wherein the IVIG is administered at a dose of 200 mg/kg-1000 mg/kg based on the weight of the pregnant woman.

10. The method of claim 1, wherein the composition is administered from gestational week 13 to gestational week 35.

11. The method of claim 1, wherein the composition is administered from gestational week 14 to gestational week 35.

12. The method of claim 1, wherein the composition is administered from gestational week 15 to gestational week 35.

13. The method of claim 1, wherein the composition is administered from gestational week 16 to gestational week 35.

* * * * *